(12) United States Patent
Atkinson et al.

(10) Patent No.: US 11,273,146 B2
(45) Date of Patent: *Mar. 15, 2022

(54) BENZOFURAN DERIVATIVES AND THEIR USE AS BROMODOMAIN INHIBITORS

(71) Applicant: GLAXOSMITHKLINE INTELLECTUAL PROPERTY (NO. 2) LIMITED, Brentford (GB)

(72) Inventors: Stephen John Atkinson, Stevenage (GB); Emmanuel Hubert Demont, Stevenage (GB); Lee Andrew Harrison, Stevenage (GB); Simon Christopher Cranko Lucas, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GlaxoSmithKline Intellectual Property (No.2) Limited, Brentford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/753,544

(22) PCT Filed: Oct. 4, 2018

(86) PCT No.: PCT/EP2018/076940
§ 371 (c)(1),
(2) Date: Apr. 3, 2020

(87) PCT Pub. No.: WO2019/068783
PCT Pub. Date: Apr. 11, 2019

(65) Prior Publication Data
US 2020/0289464 A1 Sep. 17, 2020

(30) Foreign Application Priority Data
Oct. 6, 2017 (GB) .................................... 1716369

(51) Int. Cl.
| | | |
|---|---|---|
| A61K 31/4025 | (2006.01) |
| A61K 31/343 | (2006.01) |
| A61K 31/351 | (2006.01) |
| A61K 31/397 | (2006.01) |
| A61K 31/4155 | (2006.01) |
| A61K 31/4192 | (2006.01) |
| A61K 31/4196 | (2006.01) |
| A61K 31/443 | (2006.01) |
| A61K 31/4525 | (2006.01) |
| A61K 31/501 | (2006.01) |
| A61K 31/506 | (2006.01) |
| A61K 45/06 | (2006.01) |
| C07D 307/79 | (2006.01) |
| C07D 405/10 | (2006.01) |
| C07D 405/12 | (2006.01) |
| C07D 405/14 | (2006.01) |
| C07D 407/12 | (2006.01) |
| C07D 407/14 | (2006.01) |
| C07D 413/12 | (2006.01) |
| C07D 471/04 | (2006.01) |

(52) U.S. Cl.
CPC ........ A61K 31/4025 (2013.01); A61K 31/343 (2013.01); A61K 31/351 (2013.01); A61K 31/397 (2013.01); A61K 31/4155 (2013.01); A61K 31/4192 (2013.01); A61K 31/4196 (2013.01); A61K 31/443 (2013.01); A61K 31/4525 (2013.01); A61K 31/501 (2013.01); A61K 31/506 (2013.01); A61K 45/06 (2013.01); C07D 307/79 (2013.01); C07D 405/10 (2013.01); C07D 405/12 (2013.01); C07D 405/14 (2013.01); C07D 407/12 (2013.01); C07D 407/14 (2013.01); C07D 413/12 (2013.01); C07D 471/04 (2013.01)

(58) Field of Classification Search
CPC .......................... C07D 307/79; A61K 31/4025
See application file for complete search history.

(56) References Cited

U.S. PATENT DOCUMENTS 10,583,112 B2 * 3/2020 Atkinson ............. A61K 31/343

FOREIGN PATENT DOCUMENTS

| WO | WO 2014/140077 A1 | 9/2014 |
| WO | WO 2017/050714 A1 | 3/2017 |
| WO | WO 2017/174620 A1 | 10/2017 |

* cited by examiner

*Primary Examiner* — Golam M Shameem
(74) *Attorney, Agent, or Firm* — James K. Leonard

(57) ABSTRACT

The present invention relates to compounds of formula (I) and salts thereof, pharmaceutical compositions containing such compounds and to their use in therapy.

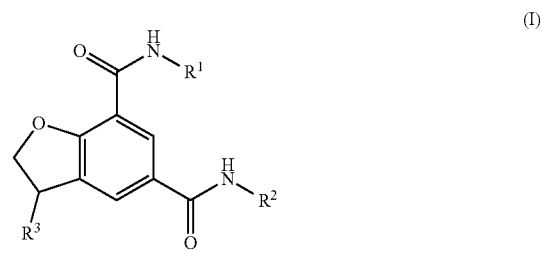

(I)

21 Claims, No Drawings

BENZOFURAN DERIVATIVES AND THEIR USE AS BROMODOMAIN INHIBITORS

This application is a § 371 of International Application No. PCT/EP2018/076940, filed 4 Oct. 2018, which claims the priority of GB 1716369.2, filed 6 Oct. 2017.

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (-110 amino acid) distinct domains within proteins that bind to acetylated lysine residues commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838).

Chan et al. report that BET bromodomain inhibition suppresses transcriptional responses to cytokine-Jak-STAT signalling in a gene-specific maner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

PCT patent application PCT/EP2017/058049 discloses a series dibenzofuran derivatives as BET family bromodomain inhibitors.

SUMMARY OF THE INVENTION

The invention is directed to compounds of formula (I)

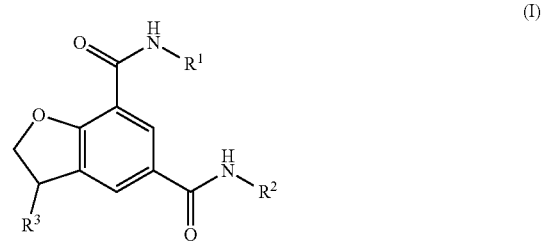

(I)

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different;
$R^2$ is —$C_{0-4}$alkyl-heterocyclyl or —$(CH_2)_p$O-heterocyclyl wherein each heterocyclyl is optionally substituted by one or two $R^9$ groups which may be the same or different;
or
$R^2$ is H, —$CH_3$, —$C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl —$(CH_2)_mNHC(O)C_{1-4}$alkyl or —$(CH_2)_n$heteroaryl wherein heteroaryl is optionally substituted by one or two $R^7$ groups which may be the same or different;
$R^3$ is phenyl optionally substituted with one, two or three $R^7$ groups which may be the same or different; or
$R^3$ is heteroaryl optionally substituted with one, two or three $R^7$ groups which may be the same or different; or
$R^3$ is heterocyclyl optionally substituted with one, two or three $R^9$ groups which may be the same or different;
each $R^5$ is independently halo, —$C_{0-6}$alkyl-$R^8$, —O—$C_{2-6}$alkyl-$R^8$, —CN or —$SO_2C_{1-3}$alkyl;
$R^6$ is —H or $C_{1-3}$alkyl;
each $R^7$ is independently -halo, —$C_{1-4}$alkyl, —$C_{0-3}$alkyl-OR$^{10}$, —$C_{0-3}$alkyl-NR$^{15}$R$^{16}$, —$C_{0-3}$alkyl-CONR$^{15}$R$^{16}$, —$CO_2C_{1-3}$alkyl, CN or —$SO_2R^{17}$;
$R^8$ is —H, —OR$^{10a}$, —NR$^{18}$R$^{19}$ or heteroaryl;
each $R^9$ is idependently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}$R$^{12}$, —NHCH$_2$CH$_2$OR$^{13}$, —NHCO$_2$R$^{13}$, oxo, —C(O)R$^{13}$, —C(O)OR$^{13}$ or —C(O)NR$^{11}$R$^{12}$;

R$^{10a}$ is —H, —C$_{1-3}$alkyl, —C$_{2-3}$alkylNR$^{11}$R$^{12}$ or —C$_{2-3}$alkylOH;

R$^{10}$ is —H, —C$_{1-3}$alkyl, —C$_{2-3}$alkylNR$^{15}$R$^{16}$ or —C$_{2-3}$alkylOH;

R$^{11}$ and R$^{12}$ are each independently selected from —H and —C$_{1-3}$alkyl; or R$^{11}$ and R$^{12}$ may join together with the nitrogen to which they are attached, to form a 4 to 7-membered heterocyclyl group optionally substituted by one or two substituents independently selected from —C$_{1-3}$alkyl, —OH and F;

R$^{13}$ is —H or —C$_{1-4}$alkyl;

R$^{15}$ and R$^{16}$ are each independently selected from —H and —C$_{1-3}$alkyl;

R$^{17}$ is —C$_{1-3}$alkyl or —NR$^{15}$R$^{16}$;

R$^{18}$ and R$^{19}$ are each independently selected from —H, —C(O)OC(CH$_3$)$_3$, —C$_{1-6}$alkyl, cycloalkyl, heterocyclyl, —C$_{2-3}$alkylNR$^{13}$COC$_{1-3}$alkyl, —C$_{2-3}$alkylNR$^{15}$R$^{16}$ and —C$_{2-3}$alkyl-O—C$_{1-3}$alkyl wherein the —C$_{1-6}$alkyl and cycloalkyl may be optionally substituted by one, two or three fluoro; or R$^{18}$ and R$^{19}$ may join together with the nitrogen to which they are attached, to form a 4 to 7-membered heterocyclyl group optionally substituted by one or two substituents independently selected from —C$_{1-3}$alkyl, —OH and F;

m is an integer selected from 2, 3 and 4;

p is an integer selected from 2, 3 and 4; and n is an integer selected from 0, 1, 2, 3 and 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "C$_{1-6}$alkyl" as used herein refers to a straight or branched alkyl group having from 1 to 6 carbon atoms, for example 1 to 3 carbon atoms. For example the term "C$_{0-3}$alkyl" refers to a straight or branched alkyl group having from 0 (i.e. is absent) to 3 carbon atoms, for example 0 to 2 carbon atoms. Representative branched alkyl groups have one, two or three branches. An alkyl group may form part of a chain, for example, —C$_{0-4}$alkyl-heterocyclyl refers to a straight or branched alkyl chain having from 0 (i.e. absent) to 4 carbon atoms linked to a heterocyclyl. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon mono or bicyclic ring or a saturated spiro-linked bicyclic hydrocarbon ring, having 3, 4, 5, 6 or 7 member atoms in the ring. Examples of cycloalkyl groups include, but are not limited to, cyclopropyl, cyclobutyl, cyclopentyl, cyclohexyl, cycloheptanyl and spiro[3.3]heptanyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a monocyclic or bicyclic group having 5, 6, 8, 9, 10 or 11 member atoms, including 1, 2 3 or 4 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, benzazepinyl, 2,3,4,5-tetrahydro-1H-benzo[d]azepinyl, indolizinyl, indolyl, indolinyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, pyrrolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

"C$_{5-6}$heteroaryl" refers to a monocyclic aromatic group having 5 or 6 member atoms, including 1, 2, 3 or 4 heteroatoms independently selected from nitrogen, sulphur and oxygen. The point of attachment to the rest of the molecule may be by any suitable carbon or nitrogen atom. Examples of "C$_{5-6}$heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl, 1,5,9-triazacyclododecyl, 3-oxabicyclo[3.1.0]hexanyl, 3-azabicyclo[3.1.0]hexanyl, (1r,5s)-3-oxabicyclo[3.1.0]hexanyl and (1r,5s)-3-azabicyclo[3.1.0]hexanyl. "4 to 7-membered heterocyclyl" refers to a non-aromatic heterocyclic monocyclic or bicyclic ring system containing 4, 5, 6 or 7 ring member atoms, including one heteroatom and optionally containing a further heteroatom selected from nitrogen, oxygen or sulphur.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I).

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where the absolute stereochemistry is known and the compound is a single enantiomer, the bold or hashed wedges symbols ( ▬ / ''''') are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, funnarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

The present invention also includes isotopically-labeled compounds or a pharmaceutically acceptable salt thereof, which are identical to those recited in Formula (I) above, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Statement of the Invention

In a first aspect there are provided compounds of formula (I):

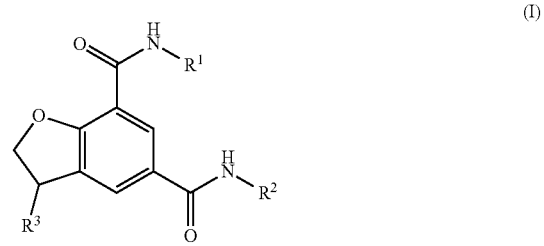

or a salt thereof
wherein:

$R^1$ is —$C_{1-3}$alkyl or cyclopropyl;

$R^2$ is —$C_{0-3}$alkyl-cycloalkyl, wherein the cycloalkyl group is optionally substituted with one, two or three $R^5$ groups which may be the same or different; or $R^2$ is —$C_{0-4}$alkyl-heterocyclyl or —$(CH_2)_pO$-heterocyclyl wherein each heterocyclyl is optionally substituted by one or two $R^9$ groups which may be the same or different; or $R^2$ is H, —$CH_3$, $C_{2-6}$alkyl optionally substituted by up to five fluoro, —$C_{2-6}$alkylOR$^{13}$, —$C_{2-6}$alkylNR$^{11}R^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl —$(CH_2)_mNHC(O)C_{1-4}$alkyl or —$(CH_2)_n$heteroaryl wherein heteroaryl is optionally substituted by one or two $R^7$ groups which may be the same or different;

$R^3$ is phenyl optionally substituted with one, two or three $R^7$ groups which may be the same or different; or $R^3$ is heteroaryl optionally substituted with one, two or three $R^7$ groups which may be the same or different; or $R^3$ is heterocyclyl optionally substituted with one, two or three $R^9$ groups which may be the same or different;

each $R^5$ is independently halo, —$C_{0-6}$alkyl-$R^8$, —O—$C_{2-6}$alkyl-$R^8$, —CN or —$SO_2C_{1-3}$alkyl;

R⁶ is —H or —C₁₋₃alkyl;

each R⁷ is independently -halo, —C₁₋₄alkyl, —C₀₋₃alkyl-OR¹⁰, —C₀₋₃alkyl-NR¹⁵R¹⁶, —C₀₋₃alkyl-CONR¹⁵R¹⁶, —CO₂C₁₋₃alkyl, CN or —SO₂R¹⁷;

R⁸ is —H, —OR¹⁰ᵃ, —NR¹⁸R¹⁹ or heteroaryl;

each R⁹ is independently halo, —C₁₋₄alkyl, cyclopropyl, cyclobutyl, —CH₂CF₃, —CH₂CHF₂, —CH₂CH₂F, —OCH₂CH₂OR¹³, —C₀₋₃alkylOR¹³, —C₀₋₃alkylNR¹¹R¹², —NHCH₂CH₂OR¹³, —NHCO₂R¹³, oxo, —C(O)R¹³, —C(O)OR¹³ or —C(O)NR¹¹R¹²;

R¹⁰ᵃ is —H, —C₁₋₃alkyl, —C₂₋₃alkylNR¹¹R¹² or —C₂₋₃alkylOH;

R¹⁰ is —H, —C₁₋₃alkyl, —C₂₋₃alkylNR¹⁵R¹⁶ or —C₂₋₃alkylOH;

R¹¹ and R¹² are each independently selected from —H and —C₁₋₃alkyl; or R¹¹ and R¹² may join together with the nitrogen to which they are attached, to form a 4 to 7-membered heterocyclyl group optionally substituted by one or two substituents independently selected from —C₁₋₃alkyl, —OH and F;

R¹³ is —H or C₁₋₄alkyl;

R¹⁵ and R¹⁶ are each independently selected from —H and —C₁₋₃alkyl;

R¹⁷ is —C₁₋₃alkyl or —NR¹⁵R¹⁶;

R¹⁸ and R¹⁹ are each independently selected from —H, —C(O)OC(CH₃)₃, —C₁₋₆alkyl, cycloalkyl, heterocyclyl, —C₂₋₃alkylNR¹³COC₁₋₃alkyl, —C₂₋₃alkylNR¹⁵R¹⁶ and —C₂₋₃alkyl-O—C₁₋₃alkyl wherein the —C₁₋₆alkyl and cycloalkyl may be optionally substituted by one, two or three fluoro; or R¹⁸ and R¹⁹ may join together with the nitrogen to which they are attached, to form a 4 to 7-membered heterocyclyl group optionally substituted by one or two substituents independently selected from —C₁₋₃alkyl, —OH and F;

m is an integer selected from 2, 3 and 4;
p is an integer selected from 2, 3 and 4; and
n is an integer selected from 0, 1, 2, 3 and 4.

In one embodiment R¹ is methyl, ethyl, propyl, iso-propyl or cyclopropyl. In another embodiment R¹ is methyl.

In one embodiment R² is —C₀₋₃alkyl-C₃₋₇cycloalkyl, wherein the C₃₋₇cycloalkyl group is optionally substituted with one, two or three R⁵ groups which may be the same or different. In another embodiment R² is —C₀₋₃alkyl-C₃₋₇cycloalkyl, wherein the C₃₋₇cycloalkyl group is cyclopropyl, cyclobutyl or cyclohexyl optionally substituted with one, two or three R⁵ groups which may be the same or different. In another embodiment R² is cyclopropyl, cyclobutyl or cyclohexyl optionally substituted with one, two or three R⁵ groups which may be the same or different. In a further embodiment R² is selected from:

In one embodiment R⁵ is —C₀₋₆alkyl-R⁸. In another embodiment R⁵ is methyl, —CH₂OH, —CH₂CH₂OH, —OH, —OMe and —CH₂CH₂morpholinyl.

In one embodiment R⁸ is OH, methyl or morpholinyl.

In one embodiment R² is —C₀₋₄alkyl-heterocyclyl or —(CH₂)ₚO-heterocyclyl wherein each heterocyclyl is optionally substituted by one or two R⁹ groups which may be the same or different. In another embodiment R² is —C₀₋₄alkyl-heterocyclyl wherein the heterocyclyl is optionally substituted by one or two R⁹ groups which may be the same or different. In another embodiment R² is —C₀₋₄alkyl-heterocyclyl which is -heterocyclyl, —CH₂CH₂-heterocyclyl or —CH₂CH₂CH₂-heterocyclyl. In another embodiment R² is —C₀₋₄alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two R⁹ groups which may be the same or different. In another embodiment R² is —C₀₋₄alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two R⁹ groups selected from methyl —C(O)CH₃ and fluoro. In a further embodiment R² is —C₀₋₄alkyl-heterocyclyl wherein heterocyclyl, optionally substituted by one or two R⁹ groups, is selected from:

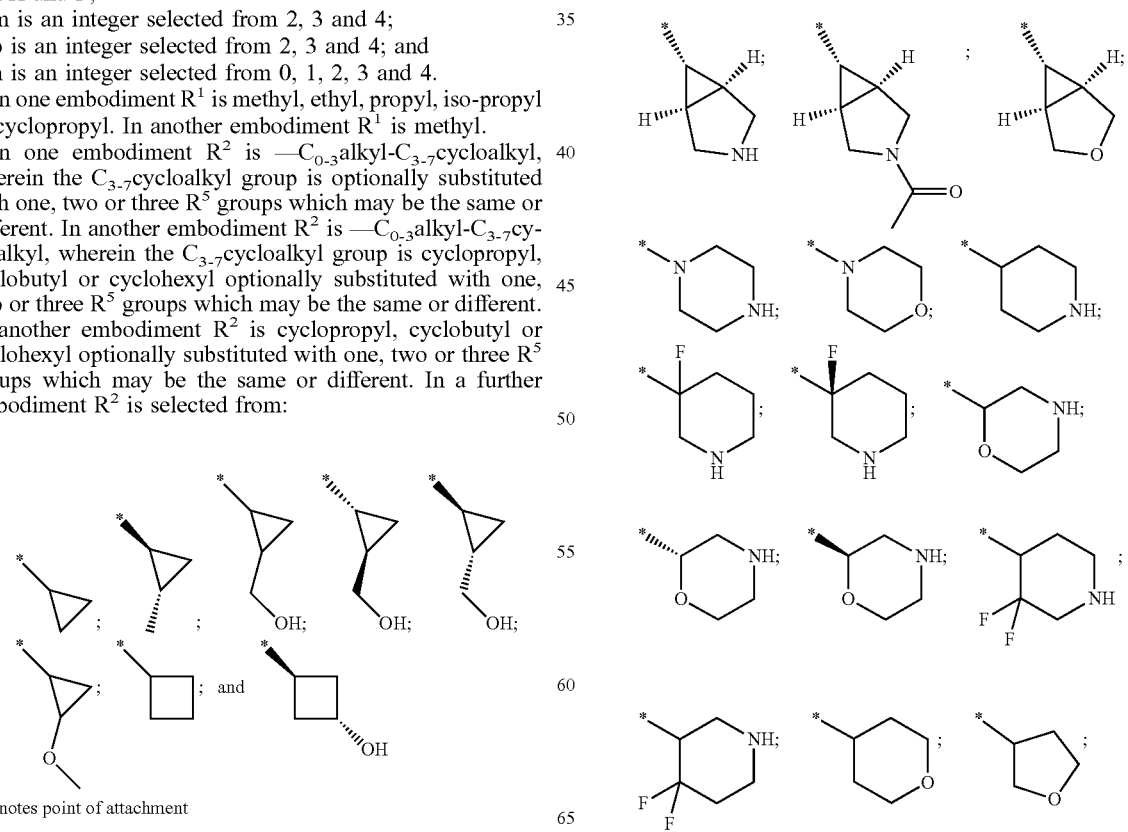

* denotes point of attachment

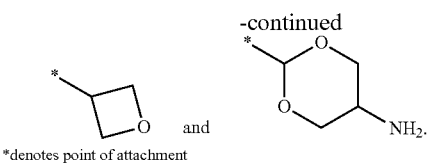

*denotes point of attachment

In one embodiment p is 2 or 3.

In one embodiment $R^2$ is —H, —$CH_3$, $C_{2-6}$alkyl optionally substituted by up to five fluoro, —$C_{2-6}$alkyl$OR^{13}$, —$C_{2-6}$alkyl$NR^{11}R^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C(CH_3)_3$ or —$(CH_2)_n$heteroaryl wherein heteroaryl is optionally substituted by one or two $R^7$ groups which may be the same or different. In another embodiment $R^2$ is —H, —$CH_3$, $C_{2-6}$alkyl, —$C_{2-6}$alkyl$OR^{13}$, —$C_{2-6}$alkyl$NR^{11}R^{12}$ or —$(CH_2)_n$heteroaryl. In a further embodiment $R^2$ is —H, methyl, ethyl, propyl, —$CH_2CH_2OH$, —$CH_2CH_2CH_2OH$, —$CH_2CH(CH_3)OH$, —$CH_2CH_2OCH_3$, —$CH_2CH_2CH_2OCH_3$, —$CH_2CH_2N(CH_3)_2$, —$CH_2CH_2CH_2N(CH_3)_2$, —$CH_2CHF_2$ or —$CH_2CH_2$pyridinyl.

In another embodiment $R^2$ is —$(CH_2)_n$heteroaryl wherein heteroaryl is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl said groups being optionally substituted by one or two $R^7$ groups which may be the same or different. In another embodiment there is provided compounds of formula (I) in which $R^2$ is —$(CH_2)_n$heteroaryl wherein the heteroaryl is pyrazolyl optionally substituted by $C_{1-4}$alkyl.

In one embodiment n is 0, 2 or 3. In one embodiment n is 0. In another embodiment n is 2.

In one embodiment $R^3$ is phenyl optionally substituted with one, two or three $R^7$ groups which may be the same or different. In one embodiment $R^3$ is phenyl optionally substituted by one -halo (e.g. F), —$CH_3$, —$OCH_3$ or CN. In another embodiment $R^3$ is phenyl.

In one embodiment $R^3$ is heteroaryl optionally substituted with one, two or three $R^7$ groups which may be the same or different. In one embodiment $R^3$ is pyridyl optionally substituted with one $R^7$ group. In one embodiment $R^3$ is indolyl optionally substituted with one or two $R^7$ groups which may be the same or different. In another embodiment $R^3$ is indolyl (such as indol-4-yl).

In one embodiment $R^3$ is heterocyclyl optionally substituted with one, two or three $R^9$ groups which may be the same or different. In one embodiment $R^3$ is tetrahydropyranyl optionally substituted with one or two $R^9$ groups which may be the same or different. In another embodiment $R^3$ is tetrahydropyranyl (such as tetrahydropyran-3-yl or tetrahydropyran-4-yl).

It is to be understood that the present invention covers all combinations of substituent groups described hereinabove.

Compounds of the invention include the compounds of Examples 1 to 123 and salts thereof.

In one embodiment the compound of formula (I) is selected from:
$N^5$-cyclopropyl-3-(1H-indol-4-yl)-$N^7$-methyl-2,3-dihydrobenzofuran-5,7-dicarboxamide;
(+/−)—$N^5$-((1R,5S,6r)-3-Oxabicyclo[3.1.0]hexan-6-yl)-3-(1H-indol-4-yl)-$N^7$-methyl-2,3-dihydrobenzofuran-5,7-dicarboxamide;
$N^5$-(2-(1H-pyrazol-5-yl)ethyl)-$N^7$-methyl-3-phenyl-2,3-dihydrobenzofuran-5,7-dicarboxamide;
$N^5$-(2-(3,3-difluoropiperidin-4-yl)ethyl)-$N^7$-methyl-3-phenyl-2,3-dihydrobenzofuran-5,7-dicarboxamide;
3-(4-fluorophenyl)-$N^7$-methyl-$N^5$-(2-(1-methyl-1H-pyrazol-4-yl)ethyl)-2,3-dihydrobenzofuran-5,7-dicarboxamide;
$N^7$-methyl-3-phenyl-$N^5$-(pyridin-4-yl)-2,3-dihydrobenzofuran-5,7-dicarboxamide;
$N^5$-(1-(2-hydroxyethyl)-1H-pyrazol-4-yl)-$N^7$-methyl-3-phenyl-2,3-dihydrobenzofuran-5,7-dicarboxamide;
$N^7$-methyl-3-phenyl-$N^5$-(2-(pyridin-4-yl)ethyl)-2,3-dihydrobenzofuran-5,7-dicarboxamide;
$N^5$-(2-methoxycyclopropyl)-$N^7$-methyl-3-phenyl-2,3-dihydrobenzofuran-5,7-dicarboxamide;
$N^7$-methyl-$N^5$-(1-methyl-1H-1,2,3-triazol-4-yl)-3-phenyl-2,3-dihydrobenzofuran-5,7-dicarboxamide;
$N^7$-methyl-3-phenyl-$N^5$-(pyrimidin-5-yl)-2,3-dihydrobenzofuran-5,7-dicarboxamide;
$N^7$-methyl-3-phenyl-$N^5$-(pyridin-3-yl)-2,3-dihydrobenzofuran-5,7-dicarboxamide;
$N^7$-methyl-$N^5$-((1S,2S)-2-methylcyclopropyl)-3-phenyl-2,3-dihydrobenzofuran-5,7-dicarboxamide;
$N^5$-((1R,5S,6r)-3-oxabicyclo[3.1.0]hexan-6-yl)-$N^7$-methyl-3-phenyl-2,3-dihydrobenzofuran-5,7-dicarboxamide;
$N^5$-(3-(3,3-difluoropiperidin-4-yl)propyl)-$N^7$-methyl-3-phenyl-2,3-dihydrobenzofuran-5,7-dicarboxamide;
(+/−)—$N^7$-methyl-$N^5$-(1-methyl-1H-pyrazol-4-yl)-3-phenyl-2,3-dihydrobenzofuran-5,7-dicarboxamide;
(S*)-$N^7$-methyl-$N^5$-(2-methyl-2H-1,2,3-triazol-4-yl)-3-phenyl-2,3-dihydrobenzofuran-5,7-dicarboxamide;
(S*)-$N^7$-methyl-$N^5$-(1-methyl-1H-pyrazol-4-yl)-3-phenyl-2,3-dihydrobenzofuran-5,7-dicarboxamide;
(S*)-$N^5$-(1-(2-hydroxyethyl)-1H-pyrazol-4-yl)-$N^7$-methyl-3-phenyl-2,3-dihydrobenzofuran-5,7-dicarboxamide;
(+/−)-$N^5$-cyclopropyl-$N^7$-methyl-3-phenyl-2,3-dihydrobenzofuran-5,7-dicarboxamide;
(+/−)-$N^7$-methyl-3-phenyl-$N^5$-(pyrimidin-4-yl)-2,3-dihydrobenzofuran-5,7-dicarboxamide;
(+/−)-$N^7$-methyl-3-phenyl-$N^5$-(pyridazin-4-yl)-2,3-dihydrobenzofuran-5,7-dicarboxamide;
(+/−)-$N^7$-methyl-3-phenyl-$N^5$-(pyridazin-3-yl)-2,3-dihydrobenzofuran-5,7-dicarboxamide;
(+/−)-$N^7$-methyl-3-phenyl-$N^5$-(tetrahydrofuran-3-yl)-2,3-dihydrobenzofuran-5,7-dicarboxamide;
(+/−)-$N^5$-((1R,5S,6r)-3,3-difluorobicyclo[3.1.0]hexan-6-yl)-$N^7$-methyl-3-phenyl-2,3-dihydrobenzofuran-5,7-dicarboxamide;
(S*)-$N^7$-methyl-$N^5$-(2-(1-methyl-1H-pyrazol-4-yl)ethyl)-3-phenyl-2,3-dihydrobenzofuran-5,7-dicarboxamide;
(S*)-$N^5$-ethyl-$N^7$-methyl-3-phenyl-2,3-dihydrobenzofuran-5,7-dicarboxamide;
(+/−)$N^7$-methyl-3-phenyl-$N^5$-(2-(pyridin-3-yl)ethyl)-2,3-dihydrobenzofuran-5,7-dicarboxamide;
(+/−)$N^7$-methyl-$N^5$-(1-(methylsulfonyl)azetidin-3-yl)-3-phenyl-2,3-dihydrobenzofuran-5,7-dicarboxamide;
(+/−)$N^5$-(2-(1H-imidazol-4-yl)ethyl)-$N^7$-methyl-3-phenyl-2,3-dihydrobenzofuran-5,7-dicarboxamide;
(+/−)$N^7$-methyl-3-phenyl-$N^5$-((tetrahydrofuran-3-yl)methyl)-2,3-dihydrobenzofuran-5,7-dicarboxamide;
(+/−)$N^7$-methyl-$N^5$-((1-methyl-1H-pyrazol-4-yl)methyl)-3-phenyl-2,3-dihydrobenzofuran-5,7-dicarboxamide;
(+/−)$N^5$-(3-methoxypropyl)-$N^7$-methyl-3-phenyl-2,3-dihydrobenzofuran-5,7-dicarboxamide;
(+/−)$N^7$-methyl-3-phenyl-$N^5$-(tetrahydro-2H-pyran-4-yl)-2,3-dihydrobenzofuran-5,7-dicarboxamide;

(+/−)N⁵-(2-methoxyethyl)-N⁷-methyl-3-phenyl-2,3-dihydrobenzofuran-5,7-dicarboxamide;
(+/−)N⁷-methyl-N⁵-(3-methyl-1H-pyrazol-4-yl)-3-phenyl-2,3-dihydrobenzofuran-5,7-dicarboxamide;
(+/−)N⁷-methyl-N⁵-(1-methyl-1H-1,2,4-triazol-3-yl)-3-phenyl-2,3-dihydrobenzofuran-5,7-dicarboxamide;
(+/−)3-(4-Fluorophenyl)-N⁷-methyl-N⁵-(1-methyl-1H-pyrazol-4-yl)-2,3-dihydrobenzofuran-5,7-dicarboxamide;
(+/−)-N⁷-Methyl-N⁵-(oxetan-3-yl)-3-phenyl-2,3-dihydrobenzofuran-5,7-dicarboxamide;
(+/−)-N⁵-Ethyl-N⁷-methyl-3-phenyl-2,3-dihydrobenzofuran-5,7-dicarboxamide;
(+/−)-N⁵-((trans)-2-(2-Hydroxyethyl)cyclopropyl)-N⁷-methyl-3-phenyl-2,3-dihydrobenzofuran-5,7-dicarboxamide;
(+/−)-N(+/−)-N⁷-Methyl-N⁵-(2-(1-methyl-1H-pyrazol-4-yl)ethyl)-3-phenyl-2,3-dihydrobenzofuran-5,7-dicarboxamide;
⁷-Methyl-N⁵-(2-methyl-2H-1,2,3-triazol-4-yl)-3-phenyl-2,3-dihydrobenzofuran-5,7-dicarboxamide;
(S)-N⁷-methyl-3-phenyl-N⁵-(pyrimidin-5-yl)-2,3-dihydrobenzofuran-5,7-dicarboxamide;
(S*)-3-(4-fluorophenyl)-N⁷-methyl-N⁵-(2-(1-methyl-1H-pyrazol-4-yl)ethyl)-2,3-dihydrobenzofuran-5,7-dicarboxamide;
(S*)-3-(1H-indol-4-yl)-N⁷-methyl-N⁵-(2-(1-methyl-1H-pyrazol-4-yl)ethyl)-2,3-dihydrobenzofuran-5,7-dicarboxamide;
(S*)-N⁵-cyclopropyl-3-(4-fluorophenyl)-N⁷-methyl-2,3-dihydrobenzofuran-5,7-dicarboxamide;
(R*)-N⁵-((1R,5S,6r)-3-oxabicyclo[3.1.0]hexan-6-yl)-N⁷-methyl-3-(o-tolyl)-2,3-dihydrobenzofuran-5,7-dicarboxamide;
(S*)-N⁷-methyl-N⁵-((1S,2S)-2-methylcyclopropyl)-3-phenyl-2,3-dihydrobenzofuran-5,7-dicarboxamide;
(S*)-N⁵-((1R,5S,6r)-3-oxabicyclo[3.1.0]hexan-6-yl)-N⁷-methyl-3-phenyl-2,3-dihydrobenzofuran-5,7-dicarboxamide;
(S*)-N⁵-cyclopropyl-N⁷-methyl-3-phenyl-2,3-dihydrobenzofuran-5,7-dicarboxamide;
(S*)-3-(4-(2-aminoethoxy)phenyl)-N⁵-((1R,5S,6r)-3-oxabicyclo[3.1.0]hexan-6-yl)-N⁷-methyl-2,3-dihydrobenzofuran-5,7-dicarboxamide;
(S*)-N⁵-((1R,5S,6r)-3-oxabicyclo[3.1.0]hexan-6-yl)-N⁷-methyl-3-phenyl-2,3-dihydrobenzofuran-5,7-dicarboxamide;
(S*)-N⁵-cyclopropyl-3-(3-fluorophenyl)-N⁷-methyl-2,3-dihydrobenzofuran-5,7-dicarboxamide;
(S*)-N⁵-((1R,5S,6r)-3-oxabicyclo[3.1.0]hexan-6-yl)-N⁷-methyl-3-(tetrahydro-2H-pyran-4-yl)-2,3-dihydrobenzofuran-5,7-dicarboxamide;
(S*)-N⁵-cyclopropyl-N⁷methyl-3-(tetrahydro-2H-pyran-4-yl)-2,3-dihydrobenzofuran-5,7-dicarboxamide;
(S*)-N⁷-methyl-N⁵-((1S,2S)-2-methylcyclopropyl)-3-(tetrahydro-2H-pyran-4-yl)-2,3-dihydrobenzofuran-5,7-dicarboxamide;
(S*)-3-(4-fluorophenyl)-N⁷-methyl-N⁵-(1-methyl-1H-pyrazol-4-yl)-2,3-dihydrobenzofuran-5,7-dicarboxamide;
(R*)-N⁵-Cyclopropyl-(1H-indol-4-yl)-N⁷-methyl-2,3-dihydrobenzofuran-5,7-dicarboxamide;
(R*)-N⁵-((1R,5S,6r)-3-Oxabicyclo[3.1.0]hexan-6-yl)-3-(1H-indol-4-yl)-N⁷-methyl-2,3-dihydrobenzofuran-5,7-dicarboxamide;
(R*)-3-(1H-Indol-4-yl)-N⁷-methyl-N⁵-((1S,2S)-2-methylcyclopropyl)-2,3-dihydrobenzofuran-5,7-dicarboxamide;
(S*)-3-(1H-Indol-4-yl)-N⁷-methyl-N⁵-((1S,2S)-2-methylcyclopropyl)-2,3-dihydrobenzofuran-5,7-dicarboxamide;
(R*)-N⁵-((1R,5S,6s)-3-Azabicyclo[3.1.0]hexan-6-yl)-N⁷-methyl-3-phenyl-2,3-dihydrobenzofuran-5,7-dicarboxamide;
(R*)-N⁵-((1R,5S,6r)-3-Oxabicyclo[3.1.0]hexan-6-yl)-3-(4-fluorophenyl)-N⁷-methyl-2,3-dihydrobenzofuran-5,7-dicarboxamide;
N⁵-cyclopropyl-N⁷-methyl-3-(1-methyl-1H-indol-4-yl)-2,3-dihydrobenzofuran-5,7-dicarboxamide;
N⁵-cyclopropyl-3-(4-fluorophenyl)-N⁷-methyl-2,3-dihydrobenzofuran-5,7-dicarboxamide;
N⁵-((1R,5S,6r)-3-oxabicyclo[3.1.0]hexan-6-yl)-3-(3-methoxyphenyl)-N⁷-methyl-2,3-dihydrobenzofuran-5,7-dicarboxamide;
3-(4-cyanophenyl)-N⁵-cyclopropyl-N⁷-methyl-2,3-dihydrobenzofuran-5,7-dicarboxamide;
(+/−)N⁵-cyclopropyl-3-(3-methoxyphenyl)-N⁷-methyl-2,3-dihydrobenzofuran-5,7-dicarboxamide;
(+/−)N⁵-((1R,5S,6r)-3-oxabicyclo[3.1.0]hexan-6-yl)-N⁷-methyl-3-(p-tolyl)-2,3-dihydrobenzofuran-5,7-dicarboxamide;
(+/−)N⁵-((1R,5S,6r)-3-oxabicyclo[3.1.0]hexan-6-yl)-3-(3-cyanophenyl)-N⁷-methyl-2,3-dihydrobenzofuran-5,7-dicarboxamide;
(+/−)N⁵-((1R,5S,6r)-3-oxabicyclo[3.1.0]hexan-6-yl)-N⁷-methyl-3-(tetrahydro-2H-pyran-4-yl)-2,3-dihydrobenzofuran-5,7-dicarboxamide;
(+/−)-N⁵-((1R,5S,6r)-3-Oxabicyclo[3.1.0]hexan-6-yl)-N⁷-methyl-3-(pyridin-2-yl)-2,3-dihydrobenzofuran-5,7-dicarboxamide;
(+/−)-N⁵-((1R,5S,6r)-3-Oxabicyclo[3.1.0]hexan-6-yl)-N⁷-methyl-3-(pyridin-3-yl)-2,3-dihydrobenzofuran-5,7-dicarboxamide;
(+/−)-N⁵-Cyclopropyl-N⁷-methyl-3-(pyridin-3-yl)-2,3-dihydrobenzofuran-5,7-dicarboxamide;
(+/−)-N⁵-((1R,5S,6r)-3-Oxabicyclo[3.1.0]hexan-6-yl)-N⁷-methyl-3-(pyridin-4-yl)-2,3-dihydrobenzofuran-5,7-dicarboxamide;
(+/−)-N⁵-cyclopropyl-3-(3-fluorophenyl)-N⁷-methyl-2,3-dihydrobenzofuran-5,7-dicarboxamide;
(+/−)-N⁵-((1R,5S,6r)-3-Oxabicyclo[3.1.0]hexan-6-yl)-3-(3-fluorophenyl)-N⁷-methyl-2,3-dihydrobenzofuran-5,7-dicarboxamide;
(+/−)-N⁵-((1R,5S,6r)-3-Oxabicyclo[3.1.0]hexan-6-yl)-3-(4-fluorophenyl)-N⁷-methyl-2,3-dihydrobenzofuran-5,7-dicarboxamide;
rac-N⁵-((1R,5S)-3-oxabicyclo[3.1.0]hexan-6-yl)-N⁷-methyl-3-(1-methyl-1H-indol-4-yl)-2,3-dihydrobenzofuran-5,7-dicarboxamide;
N⁵-((1R,5S,6r)-3-oxabicyclo[3.1.0]hexan-6-yl)-3-(4-hydroxyphenyl)-N⁷-methyl-2,3-dihydrobenzofuran-5,7-dicarboxamide;
(+/−)-N⁵-((1R,5S,6r)-3-oxabicyclo[3.1.0]hexan-6-yl)-N⁷-methyl-3-phenyl-2,3-dihydrobenzofuran-5,7-dicarboxamide;
(+/−)-N⁵-((1R,5S,6r)-3-Oxabicyclo[3.1.0]hexan-6-yl)-N⁷-methyl-3-(1H-pyrrolo[2,3-b]pyridin-4-yl)-2,3-dihydrobenzofuran-5,7-dicarboxamide;
N⁵-cyclopropyl-3-(1-(2-hydroxyethyl)-1H-indol-4-yl)-N⁷-methyl-2,3-dihydrobenzofuran-5,7-dicarboxamide;
N⁵-((1R,5S,6s)-3-azabicyclo[3.1.0]hexan-6-yl)-N⁷-methyl-3-phenyl-2,3-dihydrobenzofuran-5,7-dicarboxamide;
(S)-N⁵-(3-((2s,5R)-5-amino-1,3-dioxan-2-yl)propyl)-N⁷-methyl-3-phenyl-2,3-dihydrobenzofuran-5,7-dicarboxamide;
(+/−)-3-(4-(2-aminoethoxy)phenyl)-N⁵-((1R,5S,6r)-3-oxabicyclo[3.1.0]hexan-6-yl)-N⁷-methyl-2,3-dihydrobenzofuran-5,7-dicarboxamide;

(+/−)-N⁵-((1R,5S,6s)-3-acetyl-3-azabicyclo[3.1.0]hexan-6-yl)-N⁷-methyl-3-phenyl-2,3-dihydrobenzofuran-5,7-dicarboxamide;

(+/−)N⁵-((1R,5S,6r)-3-oxabicyclo[3.1.0]hexan-6-yl)-3-(1H-indol-3-yl)-N⁷-methyl-2,3-dihydrobenzofuran-5,7-dicarboxamide;

(+/−)-N⁵-((1R,5S,6r)-3-Oxabicyclo[3.1.0]hexan-6-yl)-3-(3-(2-hydroxyethoxy)phenyl)-N⁷-methyl-2,3-dihydrobenzofuran-5,7-dicarboxamide;

(S)-N⁷-Methyl-3-phenyl-N⁵-((1R,5S,6s)-3-propionyl-3-azabicyclo[3.1.0]hexan-6-yl)-2,3-dihydrobenzofuran-5,7-dicarboxamide;

(+/−)-N⁵-((1R,5S,6r)-3-Oxabicyclo[3.1.0]hexan-6-yl)-3-(1-(2-hydroxyethyl)-1H-indol-4-yl)-N⁷-methyl-2,3-dihydrobenzofuran-5,7-dicarboxamide;

(S)-N⁵-(2-((2r,5S)-5-amino-1,3-dioxan-2-yl)ethyl)-N⁷-methyl-3-phenyl-2,3-dihydrobenzofuran-5,7-dicarboxamide; and (+/−)N⁷-methyl-N⁵-(2-((R)-morpholin-2-yl)ethyl)-3-phenyl-2,3-dihydrobenzofuran-5,7-dicarboxamide or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolennia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukaemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), ora pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situgellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in Internation Patent Application WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other theraputically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in Schemes 1-3 below:

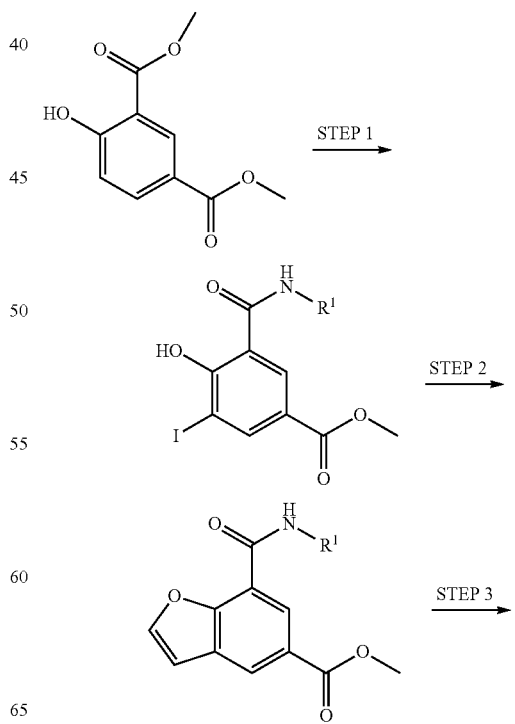

Scheme 1

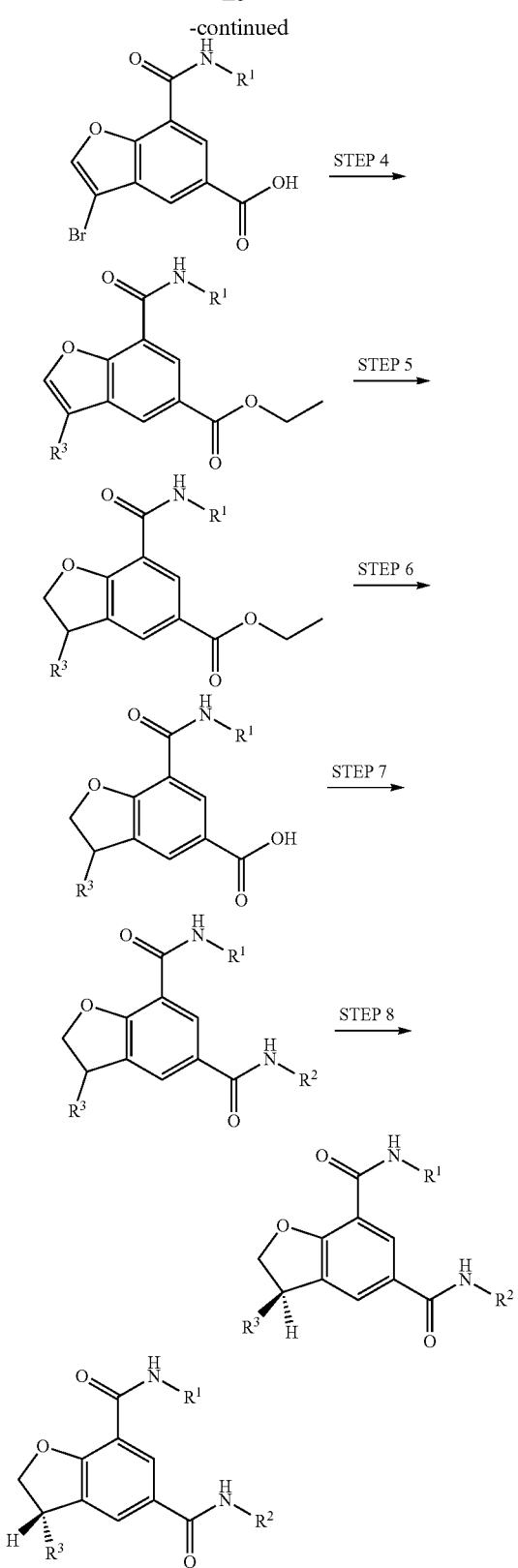

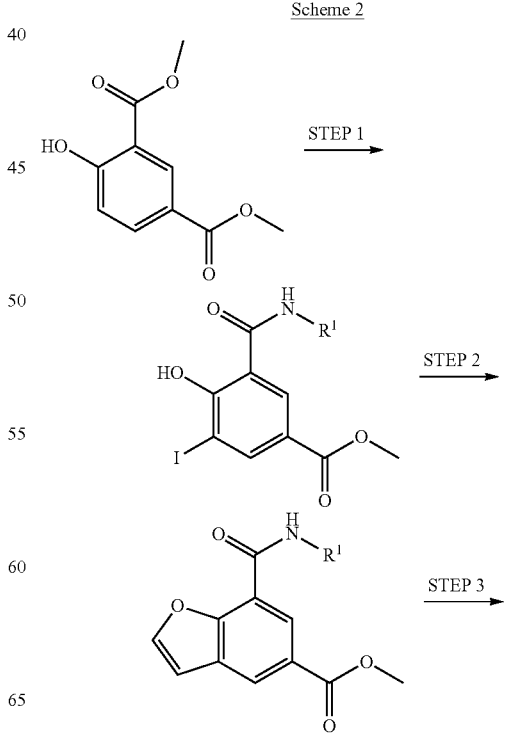

Step 2: is a cyclisation and can be carried out using an appropriate palladium catalyst, in the presence of a base.

Step 3: is a bromination which can be carried out using a suitable brominating agent such as bromine or NBS, in a suitable solvent such as dichloromethane, at a suitable temperature such as room temperature.

Step 4: is a Suzuki coupling reaction using a suitable boronic acid in the presence of a suitable palladium catalyst.

Step 5: is a hydrogenation reaction using a suitable catalyst such as Pd/C catalyst in a suitable solvent such as ethanol.

Step 6: is a saponification and can be carried out using an appropriate hydroxide salt such as sodium hydroxide, in an adequate solvent such as a mixture of THF, methanol and water, at an appropriate temperature such as room temperature.

Step 7: is an amide formation reaction which can be carried out using an appropriate activating agent such as HATU, in the presence of an adequate base, such as a trialkylamine (for example triethylamine or diisopropylethylamine) or pyridine, and using the appropriate primary amine $R^2NH_2$, in an appropriate solvent such as dichloromethane or DMF, at an adequate temperature such as room temperature.

Step 8: is a an optional separation of isomers, which can be carried out using the appropriate chomatographic system (solid or liquid phase). This step can be performed as the last step of the synthesis of compounds of Formula (I) but can also be performed at earlier stages in the process. It should be understood as well that the products from such separation steps can be obtained by methods known to one skilled in the art, such as purification by chromatography on chiral column, into single enantiomers.

Scheme 2

In respect of the steps shown in Scheme 1 above the following reaction conditions may be utilised to access Compounds of Formula (I) wherein $R^4$ is methyl:

Step 1: is an amide formation reaction followed by iodoination.

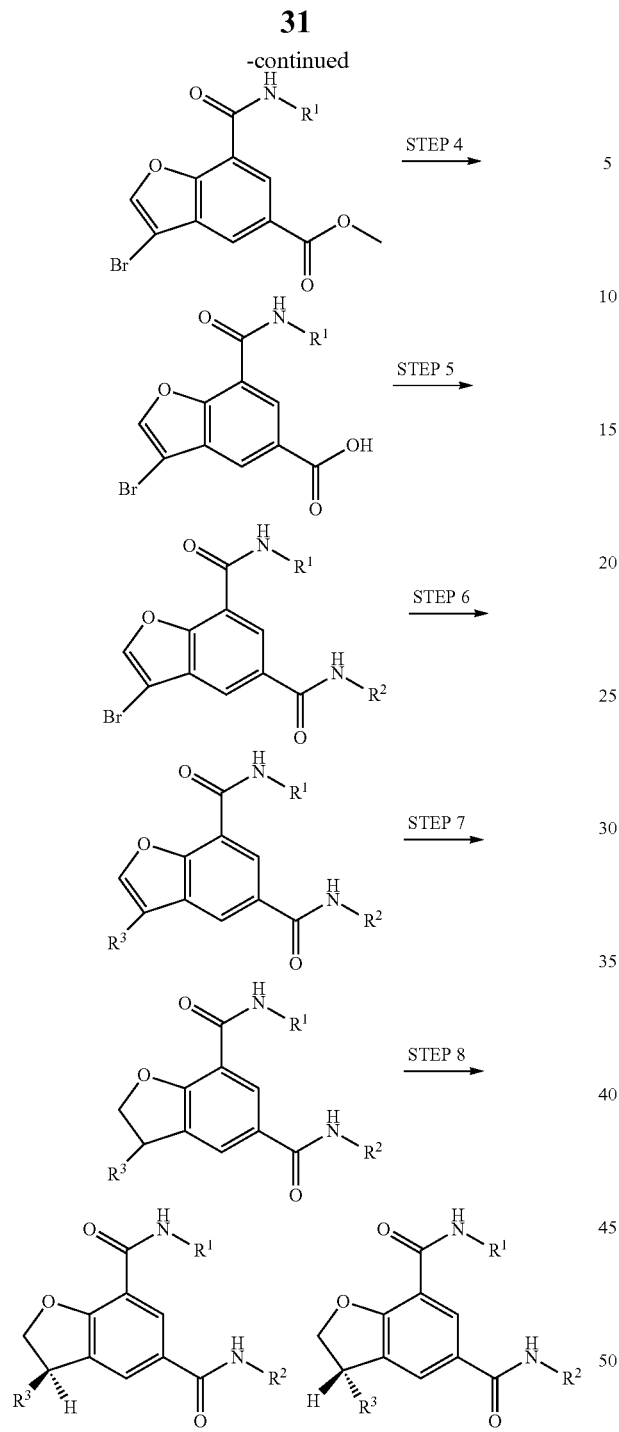

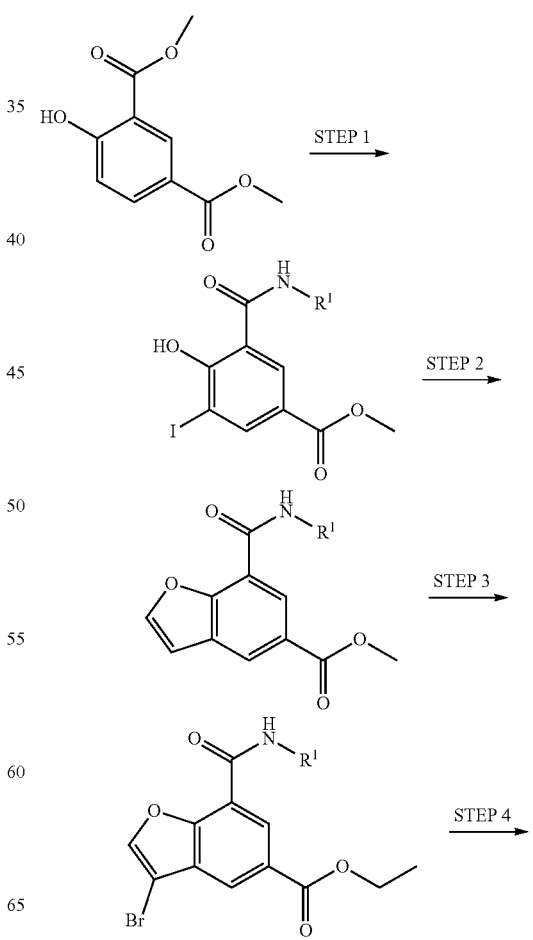

adequate solvent such as a mixture of THF, methanol and water, at an appropriate temperature such as room temperature.

Step 5: is an amide formation reaction which can be carried out using an appropriate activating agent such as HATU, in the presence of an adequate base, such as a trialkylamine (for example triethylamine or diisopropylethylamine) or pyridine, and using the appropriate primary amine $R^2NH_2$, in an appropriate solvent such as dichloromethane or DMF, at an adequate temperature such as room temperature.

Step 6: is a Suzuki coupling reaction using a suitable boronic acid in the presence of a suitable palladium catalyst.

Step 7: is a hydrogenation reaction using a suitable catalyst such as Pd/C catalyst in a suitable solvent such as ethanol.

Step 8: is a an optional separation of isomers, which can be carried out using the appropriate chomatographic system (solid or liquid phase). This step can be performed as the last step of the synthesis of compounds of Formula (I) but can also be performed at earlier stages in the process. It should be understood as well that the products from such separation steps can be obtained by methods known to one skilled in the art, such as purification by chromatography on chiral column, into single enantiomers.

Scheme 3

In respect of the steps shown in Scheme 2 above the following reaction conditions may be utilised to access Compounds of Formula (I) wherein $R^4$ is methyl:

Step 1: is an amide formation reaction followed by iodoination.

Step 2: is a cyclisation and can be carried out using an appropriate palladium catalyst, in the presence of a base.

Step 3: is a bromination which can be carried out using a suitable brominating agent such as bromine or NBS, in a suitable solvent such as dichloromethane, at a suitable temperature such as room temperature.

Step 4: is a saponification and can be carried out using an appropriate hydroxide salt such as sodium hydroxide, in an

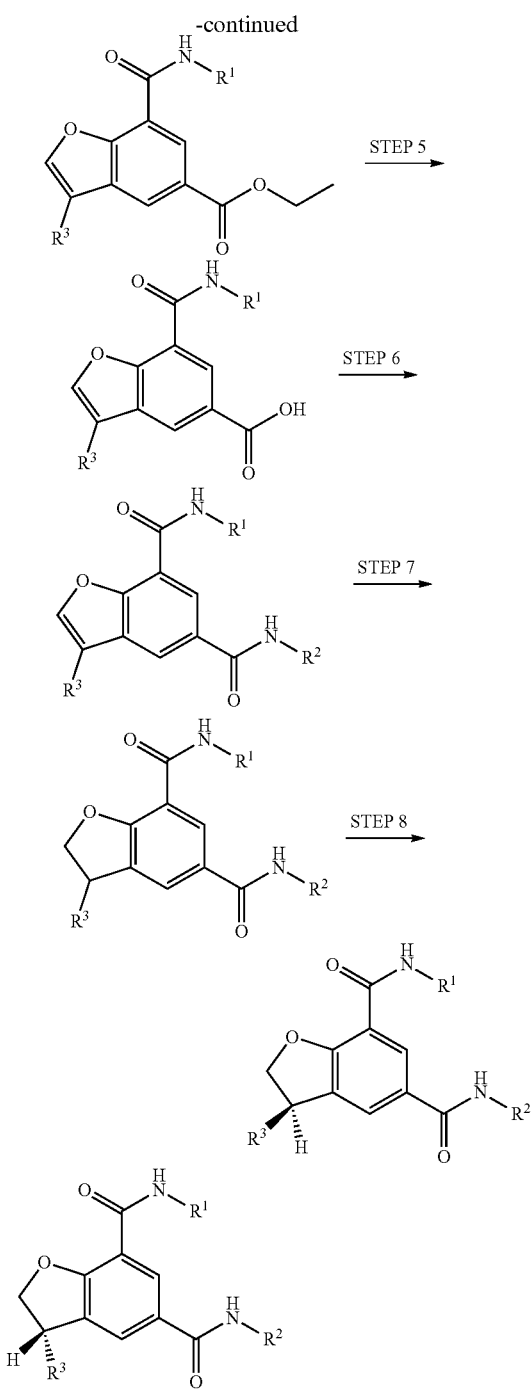

In respect of the steps shown in Scheme 3 above the following reaction conditions may be utilised to access Compounds of Formula (I) wherein $R^4$ is methyl:

Step 1: is an amide formation reaction followed by iodoination.

Step 2: is a cyclisation and can be carried out using an appropriate palladium catalyst, in the presence of a base.

Step 3: is a bromination followed by a transesterification which can be carried out using a suitable brominating agent such as bromine or NBS, in a suitable solvent such as dichloromethane, at a suitable temperature such as room temperature, followed by treatment with a suitable base in ethanol.

Step 4: is a Suzuki coupling reaction using a suitable boronic acid in the presence of a suitable palladium catalyst.

Step 5: is a saponification and can be carried out using an appropriate hydroxide salt such as sodium hydroxide, in an adequate solvent such as a mixture of THF, methanol and water, at an appropriate temperature such as room temperature.

Step 6: is an amide formation reaction which can be carried out using an appropriate activating agent such as HATU, in the presence of an adequate base, such as a trialkylamine (for example triethylamine or diisopropylethylamine) or pyridine, and using the appropriate primary amine $R^2NH_2$, in an appropriate solvent such as dichloromethane or DMF, at an adequate temperature such as room temperature.

Step 7: is a hydrogenation reaction using a suitable catalyst such as Pd/C catalyst in a suitable solvent such as ethanol.

Step 8: is a an optional separation of isomers, which can be carried out using the appropriate chomatographic system (solid or liquid phase). This step can be performed as the last step of the synthesis of compounds of Formula (I) but can also be performed at earlier stages in the process. It should be understood as well that the products from such separation steps can be obtained by methods known to one skilled in the art, such as purification by chromatography on chiral column, into single enantiomers.

EXAMPLES

General Methods
General Experimental Details
All temperatures referred to are in ° C.
As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations
AcOH acetic acid
BOC/Boc tert-butyloxycarbonyl
Boc$_2$O di-tert-butyl dicarbonate
CHCl$_3$ chloroform
Cobalt carbonyl dicobalt octacarbonyl
CV column volume
DMSO-d$_6$ deuterated dimethylsulfoxide
DCM dichloromethane
DIAD diisopropyl azodicarboxylate
DIPEA diisopropylethylamine
DMAP 4-dimethylaminopyridine
DMF dimethylformamide
DMSO dimethylsulfoxide
DMSO-d$_6$ deuterated dimethylsulfoxide
Et$_3$N triethylamine
Et$_2$O diethyl ether
EtOAc ethyl acetate
EtOH ethanol
h hour(s)
HATU O-(7-azabenzotriazol-1-yl)-N,N,N',N'-tetramethyluronium hexafluorophosphate
HCl hydrochloric acid
IPA isopropyl alcohol
Isolera Biotage Flash purification system
KCN potassium cyanide K₂CO₃ potassium carbonate
KI potassium iodide
KOH potassium hydroxide
LCMS liquid chromatography-mass spectrometry
LiBH₄ lithium borohydride
LiOH lithium hydroxide
M molar (concentration)
mCPBA meta-chloroperoxybenzoic acid
MDAP mass directed autoprep
MeCN acetonitrile
MeOH methanol
2-MeTHF 2-methyl tetrahydrofuran
min minute(s)
MsCl methanesulfonyl chloride
MTBE methyl tert-butyl ether
N normal (concentration)
N₂ nitrogen
Na₂CO₃ sodium carbonate
NaH sodium hydride
NaOH sodium hydroxide
Na₂SO₄ sodium sulphate
NBS N-bromosuccinimide
NEt₃ triethylamine
NIS iodosuccinamide
NMP N-methyl-2-pyrrolidone
NUT nuclear protein in testis
Pd/C palladium on carbon
PEPPSI 1,3-Bis(2,6-Diisopropylphenyl)imidazol-2-ylidene](3-chloropyridyl)palladium(II) dichloride
PPh₃ triphenylphosphine
Rt retention time
rt room temperature
sat saturated
SCX Isolute strong cation exchange sorbent SPE
SiO₂ silicon dioxide
SNAP Biotage (silica) flash chromatography cartridge
SP4 Biotage Flash purification system
SPE solid phase extraction
TBME tert-butyl methyl ether
TFA trifluoroacetic acid
THF tetrahydrofuran
TMSCl/TMS-Cl trimethylsilyl chloride
TLC Thin layer chromatography
Ts tosyl
UPLC ultra performance liquid chromatograpy The names of the following compounds have been obtained using the compound naming programme "ACD Name Pro 6.02" or using the naming functionality of ChemDraw Ultra 12.0.

LCMS Methodology
  Formic Method
  LC Conditions
The UPLC analysis was conducted on an Acquity UPLC CSH C18 column (50 mm×2.1 mm, i.d. 1.7 μm packing diameter) at 40° C.
  The solvents employed were:
  A=0.1% v/v solution of formic acid in water
  B=0.1% v/v solution of formic acid in acetonitrile
  The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
  MS Conditions
  MS: Waters ZQ
  Ionisation mode: Alternate-scan positive and negative electrospray
  Scan range: 100 to 1000 AMU
  Scan time: 0.27 sec
  Inter scan delay: 0.10 sec
High pH Method
  LC Conditions
The UPLC analysis was conducted on an Acquity UPLC CSH C18 column (50 mm×2.1 mm, i.d. 1.7 μm packing diameter) at 40° C.
  The solvents employed were:
  A=10 mM ammonium hydrogen carbonate in water adjusted to pH10 with ammonia solution
  B=acetonitrile
  The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
  MS Conditions
  MS: Waters ZQ
  Ionisation mode: Alternate-scan positive and negative electrospray
  Scan range: 100 to 1000 AMU
  Scan time: 0.27 sec
  Inter scan delay: 0.10 sec
TFA Method
  LC Conditions
The UPLC analysis was conducted on an Acquity UPLC CSH C18 column (50 mm×2.1 mm, i.d. 1.7 μm packing diameter) at 40° C.
  The solvents employed were:
  A=0.1% v/v solution of trifluoroacetic acid in water
  B=0.1% v/v solution of trifluoroacetic acid in acetonitrile
  The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.
  MS Conditions
  MS: Waters ZQ Ionisation mode: Alternate-scan positive and negative electrospray Scan range: 100 to 1000 AMU Scan time: 0.27 sec Inter scan delay: 0.10 sec General MDAP Purification Methods Listed below are examples of mass-directed autopreparative chromatography (MDAP) methods that have been used or may be used in compound purification.

MDAP (High pH). The HPLC analysis was conducted on an Xselect CSH C18 column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic). The HPLC analysis was conducted on an Xselect CSH C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA). The HPLC analysis was conducted on an Xselect CSH C18 column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at 302 K. GLOBAL gradient for chromatography are as follows (solvent B polar component, CV=column volume): 10% GLOBAL: 3% B for 2 CV, 3 to 13% B over 10 CV then 13% B for 5 CV; 20% GLOBAL: 5% B for 2 CV, 5 to 20% B over 10 CV then 20% B for 5 CV; 30% GLOBAL: 8% B for 2 CV, 8 to 38% B over 10 CV then 38% B for 5 CV; 40% GLOBAL: 10% B for 2 CV, 10 to 50% B over 10 CV then 50% B for 5 CV; 50% GLOBAL: 13% B for 2 CV, 13 to 63% B over 10 CV then 63% B for 5 CV. 100% GLOBAL: 25% B for 2 CV, 25 to 100% B over 10 CV then 100% B for 10 CV.

Intermediate 1: Dimethyl 4-hydroxyisophthalate

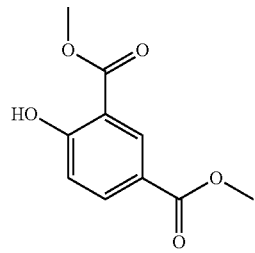

Thionyl chloride (15 mL, 206 mmol) was added dropwise to a solution of 4-hydroxyisophthalic acid (5 g, 27.5 mmol, commercially available from, for example, Sigma Aldrich) in MeOH (50 mL) at 0° C. under nitrogen. The resulting solution was stirred at rt for 30 min before heating gently to reflux for 6 h. The reaction was allowed to cool. Upon cooling, a precipitate formed which was collected by filtration to afford dimethyl 4-hydroxyisophthalate (5.32 g, 25.3 mmol, 92% yield) as a white solid.

LCMS (Formic): Retention time 1.02, poor ionisation $^1$H NMR (DMSO-$d_6$, 400 MHz): δ (ppm) 11.01 (s, 1H), 8.36 (d, J=2.4 Hz, 1H), 8.04 (dd, J=8.6, 2.4 Hz, 1H), 7.10 (d, J=8.6 Hz, 1H), 3.91 (s, 3H), 3.83 (s, 3H)

Intermediate 2: Methyl 4-hydroxy-3-(methylcarbamoyl)benzoate

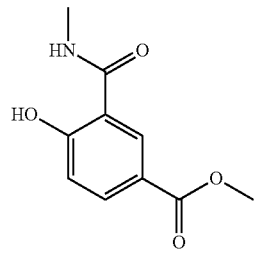

Methylamine (40% w/w in water, 20.6 mL, 238 mmol) was added to dimethyl 4-hydroxyisophthalate (For a preparation see Intermediate 1, 10 g, 47.6 mmol) in THF (100 mL) at rt. A precipitate formed and the resulting suspension was stirred at rt overnight. After this time the precipitate had dissolved. The reaction was quenched with sat. aq. NaHCO$_3$ and extracted with EtOAc and CH$_2$Cl$_2$. The combined organics were passed through a hydrophobic frit and concentrated in vacuo to afford methyl 4-hydroxy-3-(methylcarbamoyl)benzoate (9.8 g, 46.8 mmol, 98% yield) as a pink solid.

LCMS (Formic): Retention time 0.80, [MH]$^+$=210.1

$^1$H NMR (DMSO-$d_6$, 400 MHz): δ (ppm) 11.55 (d, J=4.6 Hz, 1H), 8.35 (d, J=2.8 Hz, 1H), 7.44 (dd, J=8.9, 2.8 Hz, 1H), 6.21 (d, J=8.9 Hz, 1H), 3.67 (s, 3H), 2.75 (d, J=4.6 Hz, 3H)

Intermediate 3: Methyl 4-hydroxy-3-iodo-5-(methylcarbamoyl)benzoate

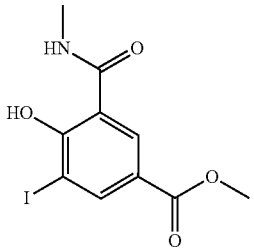 [SMILES: CNC(=O)c1cc(C(=O)OC)cc(I)c1O]

NIS (3.36 g, 14.9 mmol) was added to methyl 4-hydroxy-3-(methylcarbamoyl)benzoate (For a preparation see Intermediate 2, 2.6 g, 12.43 mmol) in CH$_2$Cl$_2$ (15 mL) at rt. The resulting solution was stirred at rt overnight. The reaction was diluted with water before sodium hydrosulfite was added until the reaction was almost colourless. The solution was extracted with CH$_2$Cl$_2$ and the combined organics were passed through a hydrophobic frit and concentrated in vacuo to afford methyl 4-hydroxy-3-iodo-5-(methylcarbamoyl)benzoate (3.62 g, 10.8 mmol, 87% yield) as a cream solid.

LCMS (Formic): Retention time 1.11, [MH]$^+$=336.0

$^1$H NMR (CDCl$_3$-d, 400 MHz): δ (ppm) 8.50 (d, J=2.0 Hz, 1H), 8.18 (d, J=2.0 Hz, 1H), 7.09 (br. s., 1H), 3.89 (s, 3H), 3.04 (d, J=4.9 Hz, 3H)

Intermediate 4: Methyl 4-hydroxy-3-(methylcarbamoyl)-5-(1-phenylvinyl)benzoate

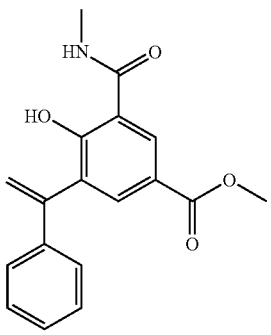 [SMILES: C=C(c1ccccc1)c1cc(C(=O)OC)cc(C(=O)NC)c1O]

(1-Phenylvinyl)boronic acid (1.06 g, 7.16 mmol), methyl 4-hydroxy-3-iodo-5-(methylcarbamoyl)benzoate (For a preparation see Intermediate 3, 2.00 g, 5.97 mmol), K$_3$PO$_4$ (3.80 g, 17.9 mmol) and PEPPSI-iPr (0.406 g, 0.597 mmol) were dissolved in 1,4-dioxane (21 mL) and water (9 mL) at rt and degassed under nitrogen. The resulting solution was stirred at 70° C. for 2 h. The reaction was allowed to cool to rt and diluted with water, extracting with CH$_2$Cl$_2$. The combined organics were passed through a hydrophobic frit and concentrated in vacuo to afford the crude product which was purifed by silica chromatography eluting with 0-30% EtOAc:cyclohexane to afford methyl 4-hydroxy-3-(methylcarbamoyl)-5-(1-phenylvinyl)benzoate (1.21 g, 3.89 mmol, 65% yield) as a cream gum.

LCMS (Formic): Retention time 1.23, [MH]$^+$=312.3

$^1$H NMR (MeOD-d$_4$, 400 MHz): δ (ppm) 8.45 (d, J=2.2 Hz, 1H), 7.96 (d, J=2.2 Hz, 1H), 7.22-7.34 (m, 5H), 5.78 (d, J=1.2 Hz, 1H), 5.38 (d, J=1.2 Hz, 1H), 3.90 (s, 3H), 2.93 (s, 3H)

Intermediate 5: (+/−)-Methyl 4-hydroxy-3-(2-hydroxy-1-phenylethyl)-5-(methylcarbamoyl)benzoate

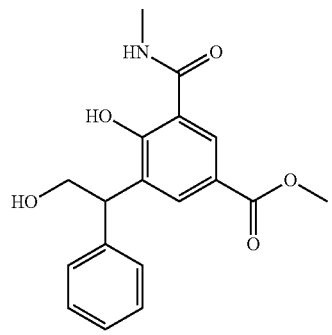 [SMILES: CNC(=O)c1cc(C(=O)OC)cc(C(CO)c2ccccc2)c1O]

A 25 mL round-bottomed flask equipped with a stirrer bar was dried under vacuum and then cooled using a stream of nitrogen. After cooling to 0° C. the reaction flask was charged with Borane-THF complex (1 M in THF, 8 mL, 8 mmol). 2,3-Dimethylbut-2-ene (2 M in THF, 4 mL, 8 mmol) was added dropwise and the resulting solution was stirred at rt for 3 h to after which a solution of thexylborane in THF (0.66 M in THF) had formed. Thexylborane (0.66 M in THF, 9.74 mL, 6.43 mmol) was then added to methyl 4-hydroxy-3-(methylcarbamoyl)-5-(1-phenylvinyl)benzoate (For a preparation see Intermediate 4, 1.3 g, 2.92 mmol) at rt under nitrogen. The resulting solution was stirred at rt overnight. Water (10 mL) was added, followed by 2M NaOH (10 mL, 20 mmol) and hydrogen peroxide (35% w/v in water, 10 mL, 114 mmol). The resulting solution was stirred at rt for 2 h. The reaction was acidified using 1M HCl and extracted with EtOAc and CH$_2$Cl$_2$. The combined organics were passed through a hydrophobic frit and concentrated in vacuo to afford (+/−)methyl 4-hydroxy-3-(2-hydroxy-1-phenylethyl)-5-(methylcarbamoyl)benzoate (600 mg, 1.82 mmol, 62% yield) as a cream solid.

LCMS (Formic): Retention time 0.96, [MH]$^+$=330.3

$^1$H NMR (MeOD-d$_4$, 400 MHz): δ (ppm) 8.33 (d, J=2.2 Hz, 1H), 8.03 (d, J=2.2 Hz, 1H), 7.26-7.33 (m, 4H), 7.15-7.23 (m, 1H), 4.66 (t, J=7.3 Hz, 1H), 4.05-4.19 (m, 2H), 3.89 (s, 3H), 2.92 (s, 3H)

Intermediate 6: (+/−)-Methyl 7-(methylcarbamoyl)-3-phenyl-2,3-dihydrobenzofuran-5-carboxylate

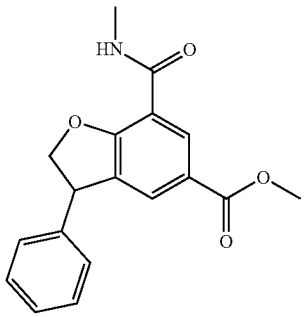 [SMILES: CNC(=O)c1cc(C(=O)OC)cc2c1OCC2c1ccccc1]

DIAD (0.149 mL, 0.765 mmol) was added dropwise to triphenylphosphine (0.201 g, 0.765 mmol) and (+/−) methyl 4-hydroxy-3-(2-hydroxy-1-phenylethyl)-5-(methylcarbamoyl)benzoate (For a preparation see Intermediate 5, 0.210 g, 0.638 mmol) in THF (10 mL) at rt. The resulting solution was stirred at rt overnight. The reaction was quenched with sat. aq. NaHCO$_3$ and extracted with CH$_2$Cl$_2$. The combined organics were passed through a hydrophobic frit and concentrated in vacuo to afford the crude product which was purified by silica chromatography, eluting with 0-80% EtOAc/cyclohexane to afford methyl (+/−)7-(methylcarbamoyl)-3-phenyl-2,3-dihydrobenzofuran-5-carboxylate (160 mg, 0.514 mmol, 81% yield) as a white solid.

LCMS (Formic): Retention time 1.04, [MH]$^+$=312.1

$^1$H NMR (CDCl$_3$-d, 400 MHz): δ (ppm) 8.74 (d, J=1.2 Hz, 1H), 7.77-7.85 (m, 1H), 7.44-7.53 (m, 1H), 7.29-7.40 (m, 3H), 7.15-7.22 (m, 2H), 5.16 (t, J=8.8 Hz, 1H), 4.64-4.78 (m, 2H), 3.86 (s, 3H), 3.06 (d, J=4.6 Hz, 3H)

Intermediate 7: (+/−)-7-(Methylcarbamoyl)-3-phenyl-2,3-dihydrobenzofuran-5-carboxylic acid

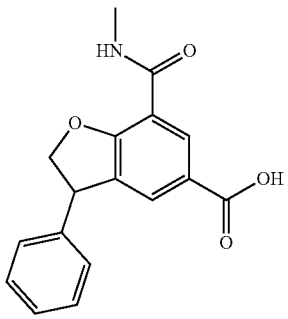 [SMILES: CNC(=O)c1cc(C(=O)O)cc2c1OCC2c1ccccc1]

LiOH (15.4 mg, 0.642 mmol) was added to (+/−)7-(methylcarbamoyl)-3-phenyl-2,3-dihydrobenzofuran-5-carboxylate (For a preparation see Intermediate 6, 100 mg, 0.321 mmol) in THF (2 mL) and water (2 mL) at rt. The resulting solution was stirred at 50° C. for 2 h. The reaction was allowed to cool, acidified with 1 M HCl and extracted with EtOAc. The combined organics were passed through a hydrophobic frit and concentrated in vacuo to afford (+/−)-7-(methylcarbamoyl)-3-phenyl-2,3-dihydrobenzofuran-5-carboxylic acid (95 mg, 0.32 mmol, 99% yield) as a colourless gum.

LCMS (Formic): Retention time 0.89, [MH]$^+$=298.2

$^1$H NMR (DMSO-d$_6$, 400 MHz): δ (ppm) 12.78 (br. s., 1H), 8.29 (d, J=1.5 Hz, 1H), 7.93 (d, J=4.6 Hz, 1H), 7.61 (dd, J=1.8, 1.1 Hz, 1H), 7.34-7.41 (m, 2H), 7.24-7.33 (m, 3H), 5.19 (t, J=9.3 Hz, 1H), 4.82-4.91 (m, 1H), 4.71 (dd, J=9.0, 6.8 Hz, 1H), 2.85 (d, J=4.9 Hz, 3H)

Intermediate 8: Methyl 7-(methylcarbamoyl)benzofuran-5-carboxylate

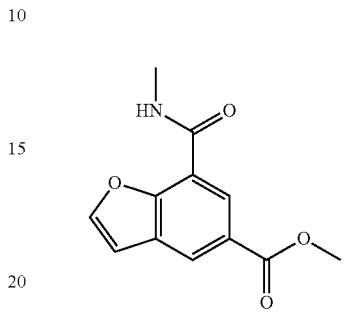

Methyl 4-hydroxy-3-iodo-5-(methylcarbamoyl)benzoate (For a preparation see Intermediate 3, 2.96 g, 8.83 mmol), ethynyltrimethylsilane (2.77 mL, 19.4 mmol), copper(I) iodide (0.168 g, 0.883 mmol), TEA (3.69 mL, 26.5 mmol), and bis(triphenylphosphine)palladium(II) chloride (0.310 g, 0.442 mmol), were dissolved in DMF (20 mL). The resulting solution was stirred at 80° C. for 18 h. The reaction was cooled, diluted with water (100 mL) and extracted with CH$_2$Cl$_2$ (3×50 mL). The combined organics were passed through a hydrophobic frit and concentrated in vacuo to afford the crude intermediate. TBAF (1M in THF) (17.67 mL, 17.67 mmol) was added to the crude intermediate and the resulting solution stirred for 2 h. The reaction was quenched with Na$_2$CO$_3$ and extracted with CH$_2$Cl$_2$. The combined organics were washed with sat. aq. LiCl, passed through a hydrophobic frit and concentrated in vacuo to afford the crude product. The crude product was taken up in CH$_2$Cl$_2$, upon which precipitate formed. The precipitate was filtered off and dried under high vacuum to afford methyl 7-(methylcarbamoyl)benzofuran-5-carboxylate (1.5 g, 6.4 mmol, 73% yield) as a pink solid.

LCMS (Formic): Retention time 0.75, [MH]$^+$=234.2

$^1$H NMR (DMSO-d$_6$, 400 MHz): δ (ppm) 8.44 (d, J=1.7 Hz, 1H), 8.35 (d, J=4.6 Hz, 1H), 8.29 (d, J=1.7 Hz, 1H), 8.22 (d, J=2.2 Hz, 1H), 7.20 (d, J=2.2 Hz, 1H), 3.91 (s, 3H), 2.89 (d, J=4.6 Hz, 3H)

Intermediate 9: 3-Bromo-7-(methylcarbamoyl)benzofuran-5-carboxylic acid

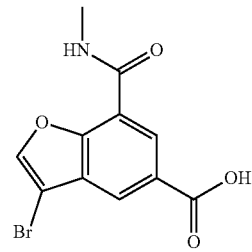 [SMILES: CNC(=O)c1cc(C(=O)O)cc2c(Br)coc12]

Bromine (1.65 mL, 32.2 mmol) was added to methyl 7-(methylcarbamoyl)benzofuran-5-carboxylate (For a preparation see Intermediate 8, 1.1 g, 4.7 mmol) in $CH_2Cl_2$ (50 mL). The resulting solution was stirred at rt for 2 h. The reaction was concentrated in vacuo to afford an orange gum. KOH (2.65 g, 47.2 mmol) was dissolved in EtOH (50 mL) then added to the crude product, and the resulting solution was stirred at rt overnight. Water (10.0 mL) was added, then the reaction was warmed to 40° C. and stirred for a further 6 h. The reaction was quenched with 10% aq. sodium metabisulfate and acidified with 2 M HCl. A white precipitate formed with was filtered off and dried under vacuum to afford 3-bromo-7-(methylcarbamoyl)benzofuran-5-carboxylic acid (6.0 g, 20.1 mmol, 94% yield) as a white solid.

LCMS (Formic): Retention time 0.77, $[MH]^+=298.0$, 300.0

$^1$H NMR (DMSO-$d_6$, 400 MHz): δ (ppm) 8.35 (m, 2H), 8.28 (d, J=4.4 Hz, 1H), 8.13 (d, J=1.2 Hz, 1H), 2.85 (d, J=4.6 Hz, 3H), acid $CO_2H$ peak not observed;

Intermediate 10: Ethyl 3-bromo-7-(methylcarbamoyl)benzofuran-5-carboxylate

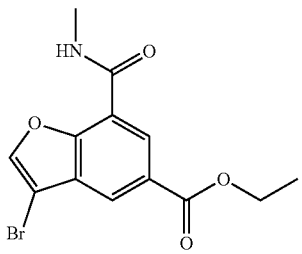 [SMILES: CCOC(=O)c1cc(C(=O)NC)c2occ(Br)c2c1]

Bromine (0.330 mL, 6.43 mmol) was added to methyl 7-(methylcarbamoyl)benzofuran-5-carboxylate (1.0 g, 4.3 mmol) in $CH_2Cl_2$ (10 mL) at rt. The resulting solution was stirred at 40° C. for 1 h, after which it was concentrated in vacuo to afford an orange gum. KOH (0.481 g, 8.58 mmol) was dissolved in Ethanol (10.0 mL) and poured onto the orange gum, the resulting solution was stirred for 5 mins until a cream precipitate formed. The precipitate was filtered off to afford ethyl 3-bromo-7-(methylcarbamoyl)benzofuran-5-carboxylate (821 mg, 2.52 mmol, 59% yield) as a cream solid.

LCMS (formic): Retention time 1.03, $[MH]^+=326.0$, 328.0

$^1$H NMR (DMSO-$d_6$, 400 MHz): δ (ppm) 8.56 (s, 1H), 8.44 (d, J=4.2 Hz, 1H), 8.34 (d, J=1.7 Hz, 1H), 8.19 (d, J=1.7 Hz, 1H), 4.39 (q, J=7.1 Hz, 2H), 1.37 (t, J=7.1 Hz, 3H)

Intermediate 11: Ethyl 7-(methylcarbamoyl)-3-phenylbenzofuran-5-carboxylate

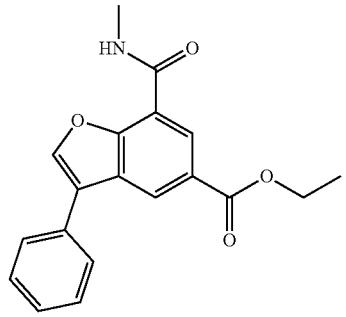 [SMILES: CCOC(=O)c1cc(C(=O)NC)c2occ(-c3ccccc3)c2c1]

Ethyl 3-bromo-7-(methylcarbamoyl)benzofuran-5-carboxylate (For a preparation see Intermediate 10, 4 g, 12.26 mmol), phenylboronic acid (1.944 g, 15.94 mmol), potassium carbonate (5.09 g, 36.8 mmol) and PEPPSI (0.167 g, 0.245 mmol) were dissolved in 1,4-dioxane (100 mL) and Water (20.0 mL) and degassed under nitrogen for 20 mins. The reaction was left to stir at 50° C. overnight. The reaction was concentrated in vacuo and the residue was taken up in DCM and washed with water. The organic phase was dried over sodium sulphate, filtered through a hydrophobic frit and concentrated in vacuo to afford ethyl 7-(methylcarbamoyl)-3-phenylbenzofuran-5-carboxylate (3.68 g, 11.38 mmol, 93% yield).

LCMS (HPH): Retention time 1.17, $[MH]^+=324.3$ $^1$H NMR (CHLOROFORM-d, 400 MHz): δ (ppm) 8.87 (d, J=1.7 Hz, 1H), 8.67 (d, J=1.7 Hz, 1H), 7.91 (s, 1H), 7.62-7.69 (m, 2H), 7.54 (t, J=7.5 Hz, 2H), 7.43-7.47 (m, 1H), 4.44 (q, J=7.1 Hz, 2H), 3.17 (d, J=4.6 Hz, 3H), 1.43 (t, J=7.1 Hz, 3H)

Intermediate 12: 7-(Methylcarbamoyl)-3-phenylbenzofuran-5-carboxylic acid

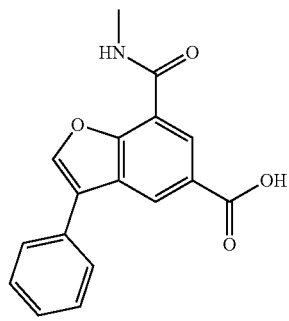 [SMILES: CNC(=O)c1cc(C(=O)O)cc2c(-c3ccccc3)coc12]

LiOH (74.1 mg, 3.09 mmol) was added to ethyl 7-(methylcarbamoyl)-3-phenylbenzofuran-5-carboxylate (For a preparation see Intermediate 11, 500 mg, 1.546 mmol) in THF (10 mL) and Water (10 mL) at rt. The resulting solution was stirred at 50° C. for 2 h after which the reaction was allowed to cool, acidified with 1M HCl (20 mL) and extracted with EtOAc (3×30 mL). The combined organics were passed through a hydrophobic frit and concentrated in vacuo to afford 7-(methylcarbamoyl)-3-phenylbenzofuran-5-carboxylic acid (452 mg, 1.53 mmol, 99% yield) as a colourless gum.

LCMS (Formic): Retention time 0.92, [MH]$^+$=296.2

$^1$H NMR (DMSO-d$_6$, 400 MHz): δ (ppm) 8.57 (s, 1H), 8.52 (d, J=1.7 Hz, 1H), 8.42 (d, J=4.6 Hz, 1H), 8.35 (d, J=1.5 Hz, 1H), 7.70-7.80 (m, 2H), 7.57 (t, J=7.6 Hz, 2H), 7.39-7.49 (m, 1H), 2.91 (d, J=4.6 Hz, 3H);

Intermediate 13: (+/−)-Ethyl 7-(methylcarbamoyl)-3-phenyl-2,3-dihydrobenzofuran-5-carboxylate

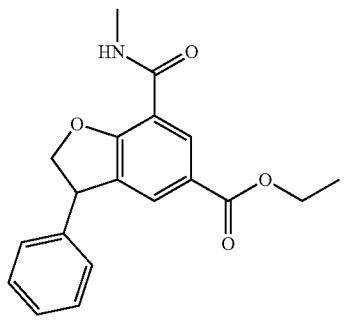 [SMILES: CCOC(=O)c1cc(C(=O)NC)c2c(c1)C(c1ccccc1)CO2]

Ethyl 7-(methylcarbamoyl)-3-phenylbenzofuran-5-carboxylate (For a preparation see Intermediate 11, 3.68 g, 11.4 mmol) was hydrogenated in EtOH (250 mL) and ethyl acetate (25 mL) using a 5% w/w Pd/C (350 mg, 3.29 mmol) catalyst. The reaction was filtered through celite before being concentrated in vacuo. The crude product was purified by silica chromatography, eluting with 5-50% EtOAc/cyclohexane to afford (+/−)ethyl 7-(methylcarbamoyl)-3-phenyl-2,3-dihydrobenzofuran-5-carboxylate (3.5 g, 10.76 mmol, 95% yield).

LCMS (HPH): Retention time 1.11, [MH]$^+$=326.3

$^1$H NMR (DMSO-d$_6$, 400 MHz): δ (ppm) 8.31 (d, J=1.7 Hz, 1H), 7.91-7.96 (m, 1H), 7.62 (s, 1H), 7.36 (d, J=7.6 Hz, 2H), 7.23-7.32 (m, 3H), 5.19 (s, 1H), 4.83-4.92 (m, 1H), 4.67-4.75 (m, 1H), 4.25 (dd, J=7.0, 5.5 Hz, 2H), 2.85 (d, J=4.6 Hz, 3H), 1.27 (t, J=7.1 Hz, 3H)

Intermediate 14 and Intermediate 15: (S*)-Ethyl-7-(methylcarbamoyl)-3-phenyl-2,3-dihydrobenzofuran-5-carboxylate and (R*)-Ethyl-7-(methylcarbamoyl)-3-phenyl-2,3-dihydrobenzofuran-5-carboxylate

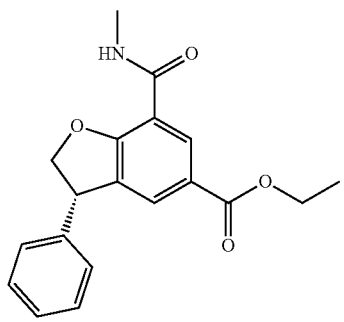

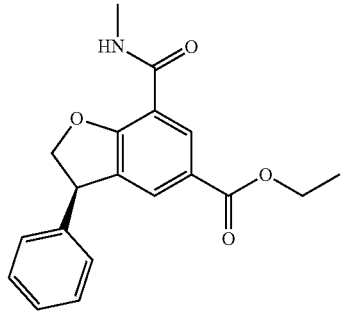

(+/−)-Ethyl 7-(methylcarbamoyl)-3-phenyl-2,3-dihydrobenzofuran-5-carboxylate (Intermediate 13) was purified by chiral HPLC using the following conditions:

Analytical method: Approximatively 0.5 mg of material was dissolved in 50% EtOH:Heptane (1 mL); 20 uL injected on column. Elution: 20% EtOH in heptane, f=1.0 mL/min, wavelength 215 nm. Column 4.6 mmid×25 cm Chiralcel OD-H.

Preparative method: Approximatively 100-150 mg of material was dissolved in EtOH (3 mL). Injections: 3 mL of the solution was injected onto the column. Elution: 15% EtOH in heptane, f=30 mL/min, wavelength, 215 nm. Column Chiralcel OD-H 250×30 mm (5 um). 21×injections.

Fractions from 11.5-13.5 mins gave (S*) Ethyl 7-(methylcarbamoyl)-3-phenyl-2,3-dihydrobenzofuran-5-carboxylate (1.00 g, 2.84 mmol, 42%) and fractions from 15-18 mins gave (R*) Ethyl 7-(methylcarbamoyl)-3-phenyl-2,3-dihydrobenzofuran-5-carboxylate (1.02 g, 0.036 mmol, 42%)

Intermediate 14: LCMS (HPH): Retention time 1.10, [MH]$^+$=326.2

Intermediate 15: LCMS (HPH): Retention time 1.10, [MH]$^+$=326.2

Intermediate 16: (S*)-7-(methylcarbamoyl)-3-phenyl-2,3-dihydrobenzofuran-5-carboxylic acid

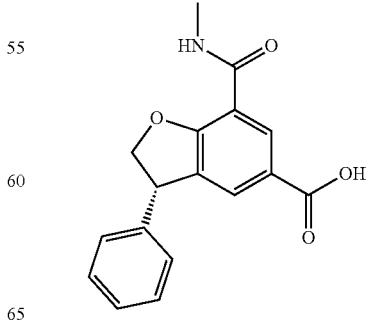

(S*) Ethyl 7-(methylcarbamoyl)-3-phenyl-2,3-dihydrobenzofuran-5-carboxylate (For a preparation see Intermediate 14, 1 g, 3.1 mmol) was taken up in THF (10 mL) and Water (10.00 mL). LiOH (0.442 g, 18.44 mmol) was added and the reaction left to stir at 50° C. overnight. The reaction was concentrated in vacuo and the residue was taken up in water and acidified to pH2 using 2 M aqueous HCl. The resulting precipitate was filtered off to afford (S*)-7-(methylcarbamoyl)-3-phenyl-2,3-dihydrobenzofuran-5-carboxylic acid (0.9 g, 3.03 mmol, 98% yield).

LCMS (Formic): Retention time 0.88, [MH]$^+$=298.2

$^1$H NMR (DMSO-d$_6$, 400 MHz): δ (ppm) 8.28 (d, J=1.7 Hz, 1H), 7.92 (d, J=4.6 Hz, 1H), 7.58-7.64 (m, 1H), 7.33-7.41 (m, 2H), 7.23-7.32 (m, 3H), 5.17 (t, J=9.4 Hz, 1H), 4.80-4.91 (m, 1H), 4.70 (dd, J=9.0, 6.8 Hz, 1H), 2.85 (d, J=4.6 Hz, 3H)

Intermediate 17: ethyl 3-(1-(tert-butyldimethylsilyl)-1H-indol-4-yl)-7-(methylcarbamoyl)benzofuran-5-carboxylate

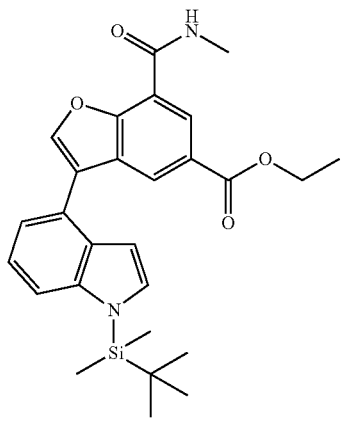 [SMILES: CCOC(=O)c1cc(C(=O)NC)c2occ(-c3cccc4c3ccn4[Si](C)(C)C(C)(C)C)c2c1]

(1-(tert-butyldimethylsilyl)-1H-indol-4-yl)boronic acid (1.031 g, 3.75 mmol), ethyl 3-bromo-7-(methylcarbamoyl)benzofuran-5-carboxylate (For a preparation see Intermediate 10, 0.940 g, 2.88 mmol), potassium carbonate (1.195 g, 8.65 mmol) and PEPPSI-iPr (0.059 g, 0.086 mmol) were dissolved in water (4.0 mL) and 1,4-dioxane (20 mL). The reaction mixture was stirred for 16 hours at 70° C. under Nitrogen, and then diluted with water (50 mL) and extracted with DCM (3×35 mL). The combined organics were passed through a hydrophobic frit and concentrated in vacuo to give the title compound (1.94 g, 2.85 mmol, 99% yield) as a white/brown solid.

LCMS (Formic): Rt: 1.58 min, [MH]$^+$=477.5

Intermediate 18: Ethyl 3-(1-(tert-butyldimethylsilyl)-1H-indol-4-yl)-7-(methylcarbamoyl)-2,3-dihydrobenzofuran-5-carboxylate

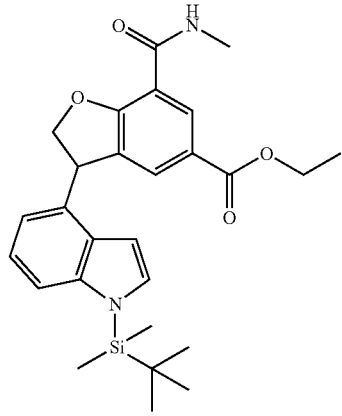 [SMILES: CCOC(=O)c1cc(C(=O)NC)c2c(c1)C(c1cccc3c1ccn3[Si](C)(C)C(C)(C)C)CO2]

Ethyl 3-(1-(tert-butyldimethylsilyl)-1H-indol-4-yl)-7-(methylcarbamoyl)benzofuran-5-carboxylate (For a preparation see Intermediate 17, 1.94 g, 4.07 mmol) and 5% w/w palladium on carbon (0.347 g, 3.26 mmol) were dissolved in ethanol (75 mL). The reaction mixture was stirred for 72 hours at 25° C. under a hydrogen atmosphere. The reaction mixture was filtered and a further batch of 5% palladium on carbon (0.347 g, 3.26 mmol) was added. The reaction mixture was stirred for a further 16 hours at 25° C. under a hydrogen atmosphere. The reaction mixture was filtered and a further batch of 5% palladium on carbon (0.347 g, 3.26 mmol) was added. The reaction mixture was once again stirred for 16 hours at 25° C. under a hydrogen atmosphere. The reaction mixture was filtered through a 10 g Celite cartridge. The filtrate was then concentrated in vacuo to give the title compound (1.24 g, 2.176 mmol, 53.5% yield) as a white solid.

LCMS (Formic): Rt: 1.53 min, [MH]$^+$=479.5

Intermediate 19: ethyl 3-(1H-indol-4-yl)-7-(methylcarbamoyl)-2,3-dihydrobenzofuran-5-carboxylate

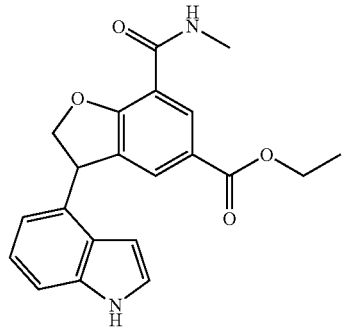 [SMILES: CCOC(=O)c1cc(C(=O)NC)c2c(c1)C(c1cccc3[nH]ccc13)CO2]

Ethyl 3-(1-(tert-butyldimethylsilyl)-1H-indol-4-yl)-7-(methylcarbamoyl)-2,3-dihydrobenzofuran-5-carboxylate (For a preparation see Intermediate 18, 1.24 g, 2.59 mmol) was dissolved in tetrahydrofuran (15 mL). To this solution TBAF (1M in THF, 3.89 mL, 3.89 mmol) was added dropwise. The reaction mixture was stirred for 30 min. The sample was then concentrated and was partitioned between EtOAc (25 mL) and water (30 mL). The organic layer was washed (1× water 20 mL, 2× sat. aq. NaHCO₃ 20 mL), passed through a hydrophobic frit and evaporated in vacuo. The sample was then purified by silica gel column chromatography, eluting with a gradient of cyclohexane:EtOAc (0-100%). The product containing fractions were combined and the solvent removed in vacuo to the title compound (682 mg, 1.872 mmol, 72.2% yield) as a white solid.

LCMS (Formic): Rt: 1.01 min, [MH]⁺=365.3

Intermediate 20: 3-(1H-indol-4-yl)-7-(methylcarbamoyl)-2,3-dihydrobenzofuran-5-carboxylic acid

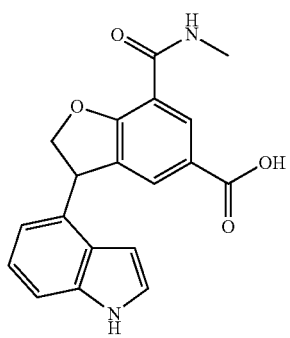 [SMILES: CNC(=O)c1cc(C(=O)O)cc2c1OCC2c1cccc2[nH]ccc12]

Ethyl 3-(1H-indol-4-yl)-7-(methylcarbamoyl)-2,3-dihydrobenzofuran-5-carboxylate (For a preparation, see Intermediate 19, 650 mg, 1.784 mmol) and LiOH (128 mg, 5.35 mmol) were dissolved in tetrahydrofuran (15 mL) and water (15 mL). The reaction mixture was stirred for 16 hours. The reaction mixture was concentrated in vacuo and was dissolved in 10 mL of water. 2M HCl was then added dropwise until a solid crashed out. The white solid was filtered off and was dried under a stream of nitrogen for 2 hours to give the title compound (582 mg, 1.64 mmol, 92% yield) as a white solid.

LCMS (High pH): Rt: 0.60 min, [MH]⁺=337.2

Intermediate 21: 3-bromo-N⁵-cyclopropyl-N⁷-methylbenzofuran-5,7-dicarboxamide

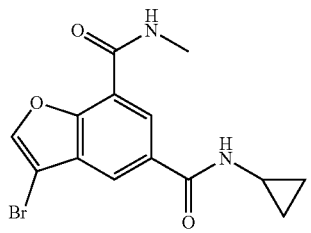

Cyclopropanamine (0.257 mL, 3.70 mmol), DIPEA (1.62 mL, 9.26 mmol) and HATU (1408 mg, 3.70 mmol) were dissolved in DMF (6 mL) with stirring at rt for 5 mins. 3-bromo-7-(methylcarbamoyl)benzofuran-5-carboxylic acid (For a preparation see Intermediate 9: 920 mg, 3.09 mmol) was added and the reaction mixture was stirred at rt for 1.5 hr. The reaction mixture was diluted with water and brine (~5 mL), and, extracted with DCM. The organics were washed with 10% LiCl solution, dried via a hydrophobic frit and concentrated in vacuo. The residue was triturated with DCM and the resulting precipitate was isolated via a scinter funnel to give the title compound (289 mg, 0.857 mmol, 27.8% yield) as a white solid.

LCMS (Formic): Rt: 0.77 min, [MH]⁺=337.1

Intermediate 22: N⁵-cyclopropyl-N⁷-methyl-3-(1-methyl-1H-indol-4-yl)benzofuran-5,7-dicarboxamide

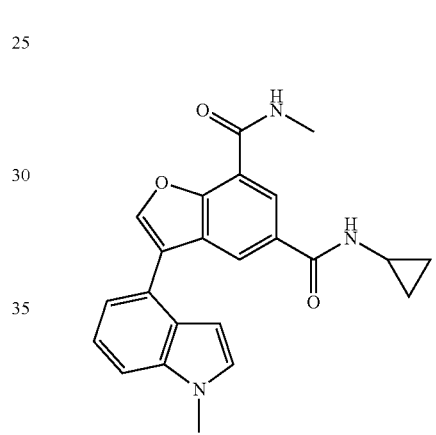

3-Bromo-N⁵-cyclopropyl-N⁷-methylbenzofuran-5,7-dicarboxamide (For a preparation see Intermediate 21, 139 mg, 0.41 mmol), (1-methyl-1H-indol-4-yl)boronic acid (216 mg, 1.24 mmol), iPr-PEPPSI (28.0 mg, 0.041 mmol) and tripotassium phosphate (263 mg, 1.24 mmol) were added to a flask with 1,4-dioxane (5 mL) and water (2.0 mL). The reaction mixture was stirred at 40° C. under nitrogen for 18 hr. The reaction mixture was eluted through a 10 g celite column with MeOH and EtOAc. The fractions were combined and concentrated in vacuo. The residue was diluted with water, extracted with EtOAc and brine (~5 mL) was added. The organics were washed with brine, dried via a hydrophobic frit and concentrated in vacuo. The residue was taken up in DCM (~5 mL), charged to a 25 g silica gel column and eluted with a gradient of 0-80% [25% EtOH in EtOAc]:cyclohexane. The relevant fractions were combined and concentrated in vacuo to give the title compound (98 mg, 0.25 mmol, 61.4% yield), an orange/brown oil.

LCMS (High pH): Rt: 1.01 min, [MH]⁺=388.4

Intermediate 23: ethyl 3-(1-methyl-1H-indol-4-yl)-7-(methylcarbamoyl)benzofuran-5-carboxylate

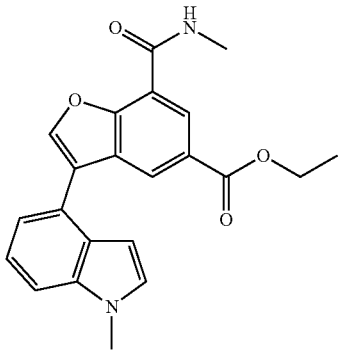 [SMILES: CCOC(=O)c1cc(C(=O)NC)c2occ(-c3cccc4c3ccn4C)c2c1]

4-(1,5-Dimethyl-2,4-dioxa-3-borabicyclo[3.1.0]hexan-3-yl)-1-methyl-1H-indole (0.996 g, 4.13 mmol), ethyl 3-bromo-7-(methylcarbamoyl)benzofuran-5-carboxylate (For a preparation see Intermediate 10, 0.9 g, 2.76 mmol), potassium carbonate (1.14 g, 8.28 mmol) and PEPPSI-iPr (0.094 g, 0.14 mmol) were degassed under nitrogen. 1,4-dioxane (15 mL) and water (3.0 mL) were added and the reaction left to stir at 50° C. overnight. The reaction was concentrated in vacuo. The residue was taken up in DCM (50 mL) and washed with water (3×50 mL). The organic phase was dried through a hydrophobic frit and concentrated in vacuo. The crude product was applied to a 50 g silica gel cartridge in the minimum of DCM and eluted with 0% Ethyl Acetate in cyclohexane for 2 CV then 0-30% Ethyl Acetate over 10 CV then held at 30% for 5 CV. The appropriate fractions were combined and concentrated in vacuo to give the title compound (280 mg, 0.744 mmol, 27.0% yield).
LCMS (High pH): Rt: 1.19 min, [MH]$^+$=248.3

Intermediate 24: 3-(1-methyl-1H-indol-4-yl)-7-(methylcarbamoyl)benzofuran-5-carboxylic acid

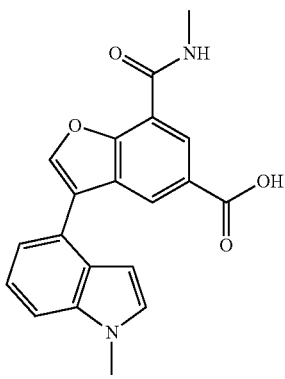 [SMILES: CNC(=O)c1cc(C(=O)O)cc2c(-c3cccc4c3ccn4C)coc12]

Ethyl 3-(1-methyl-1H-indol-4-yl)-7-(methylcarbamoyl)benzofuran-5-carboxylate (For a preparation see Intermediate 23, 280 mg, 0.744 mmol) was taken up in a mixture of ethanol (3.0 mL) and THF (3 mL). LiOH (107 mg, 4.46 mmol) was added and the reaction left to stir at 50° C. overnight. The reaction was concentrated in vacuo and the residue taken up in THF (3 mL) and water (3 mL) and the reaction left to stir at 50° C. overnight. The reaction was concentrated in vacuo. The residue was taken up in water (5 mL) and acidified with 2M aqueous HCl to pH 2. The precipitate was filtered off to give the title compound (184 mg, 0.528 mmol, 71.0% yield).
LCMS (High pH): Rt: 0.68 min, [MH]$^+$=349.3

Intermediate 25: $N^5$-((1R,5S,6r)-3-oxabicyclo[3.1.0]hexan-6-yl)-$N^7$-methyl-3-(1-methyl-1H-indol-4-yl)benzofuran-5,7-dicarboxamide

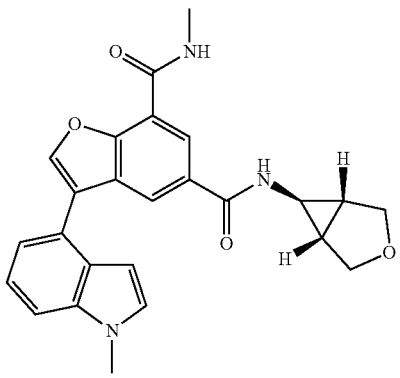 [SMILES: CNC(=O)c1cc(C(=O)N[C@H]2[C@@H]3COC[C@@H]32)cc2c(-c3cccc4c3ccn4C)coc12]

3-(1-Methyl-1H-indol-4-yl)-7-(methylcarbamoyl)benzofuran-5-carboxylic acid (For a preparation see Intermediate 24, 84 mg, 0.241 mmol) was taken up in DCM (3 mL). DIPEA (0.126 mL, 0.723 mmol), (1R,5S,6r)-3-oxabicyclo[3.1.0]hexan-6-amine, hydrochloride (39.2 mg, 0.289 mmol) and 2,4,6-tripropyl-1,3,5,2,4,6-trioxatriphosphinane 2,4,6-trioxide (0.086 mL, 0.289 mmol) was added and the reaction left to stir at room temperature overnight. Saturated aqueous sodium bicarbonate (5 mL) was added to the reaction. The reaction was extracted using DCM (3×5 mL) and the organic phase filtered through a hydrophobic frit and concentrated in vacuo to give the title compound (56 mg, 0.130 mmol, 54.1% yield).
LCMS (High pH): Rt: 0.95 min, [MH]$^+$=430.4

The following intermediates (26-30) were made by the same method as Example 3:

| Intermediate number | Structure | [MH+] | Rt (min) |
|---|---|---|---|
| 26 | (1R,5S,6s)-tert-butyl 6-(7-(methylcarbamoyl)-3-phenyl-2,3-dihydrobenzofuran-5-carboxamido)-3-azabicyclo[3.1.0]hexane-3-carboxylate | 422.4 | 1.10 (Formic) |
| 27 | (S)-N5-(4,4-diethoxybutyl)-N7-methyl-3-phenyl-2,3-dihydrobenzofuran-5,7-dicarboxamide | No ion | 1.05 (Formic) |
| 28 | (S)-N6-(2-((2r,5S)-5-(1,3-dioxoisoindolin-2-yl)-1,3-dioxan-2-yl)ethyl)-N7-methyl-3-phenyl-2,3-dihydrobenzofuran-5,7-dicarboxamide | 556 | 1.09 (formic) |

| Intermediate number | Structure | [MH+] | Rt (min) |
|---|---|---|---|
| 29 | (+/-) (2R)-tert-butyl 2-(2-(7-(methylcarbamoyl)-3-phenyl-2,3-dihydrobenzofuran-5-carboxamido)ethyl)morpholine-4-carboxylate | 510 | 1.12 (HpH) |
| 30 | (1R,5S,6s)-tert-Butyl 6-((S)-7-(methylcarbamoyl)-3-phenyl-2,3-dihydrobenzofuran-5-carboxamido)-3-azabicyclo[3.1.0]hexane-3-carboxylate | 478.4 | 1.10 (formic) |

Intermediate 31: (+/−)-tert-Butyl (2-(4-(5-(((1R,5S,6r)-3-oxabicyclo[3.1.0]hexan-6-yl)carbamoyl)-7-(methylcarbamoyl)-2,3-dihydrobenzofuran-3-yl)phenoxy)ethyl)carbamate

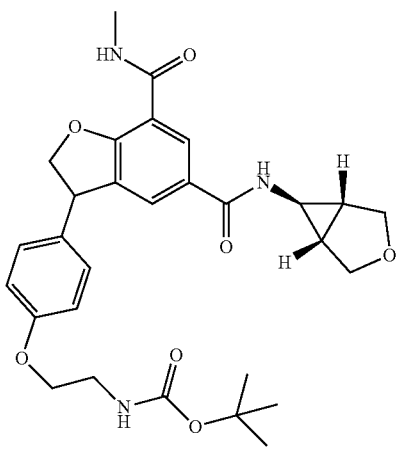 [SMILES: CNC(=O)c1cc(C(=O)N[C@H]2[C@@H]3COC[C@@H]32)cc2c1OCC2c1ccc(OCCNC(=O)OC(C)(C)C)cc1]

$N^5$-((1R,5S,6r)-3-oxabicyclo[3.1.0]hexan-6-yl)-3-(4-hydroxyphenyl)-$N^7$-methyl-2,3-dihydrobenzofuran-5,7-dicarboxamide (for a preparation, see Example 81, 140 mg, 0.36 mmol), tert-butyl (2-bromoethyl)carbamate (318 mg, 1.420 mmol) and potassium carbonate (98 mg, 0.710 mmol) were stirred in DMF (5 mL) at 50° C. for 24 h. The reaction was diluted with water and extracted with EtOAc, the organic layer was washed with 10% aq. LiCl, passed through a hydrophobic frit and concentrated in vacuo to give a colourless gum. The crude gum was purified by silica chromatography 0-6% (MeOH/DCM) to give tert-butyl (2-(4-(5-(((1R,5S,6r)-3-oxabicyclo[3.1.0]hexan-6-yl)carbamoyl)-7-(methylcarbamoyl)-2,3-dihydrobenzofuran-3-yl)phenoxy)ethyl)carbamate (100 mg, 0.186 mmol, 52% yield) as a colourless gum.

LCMS (Formic): Retention time 1.00, [MH]+=538.3

The following intermediates (32-33) were made by the same method as Example 65:

| Intermediate number | | [MH+] | Rt (min) |
|---|---|---|---|
| 32 | tert-butyl 3-(5-(((1R,5S,6r)-3-oxabicyclo[3.1.0]hexan-6-ylcarbamoyl)-7-(methylcarbamoyl)benzofuran-3-yl)-1H-indole-1-carboxylate | 516.3 | 1.23 (Formic) |
| 33 | (+/-)-N⁵-((1R,5S,6r)-3-Oxabicyclo[3.1.0]hexan-6-yl)-3-(3-hydroxyphenyl)-N⁷-methyl-2,3-dihydrobenzofuran-5,7-dicarboxamide | 395.3 | 0.74 (formic) |

Intermediate 34: tert-Butyl ((1S,2S)-2-methylcyclopropyl)carbamate

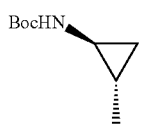

(1S,2S)-2-Methylcyclopropanecarboxylic acid (200 mg, 2.00 mmol, commercially available from, for example, Enamine) and triethylamine (0.9 mL, 6.5 mmol) were dissolved in tert-butanol (4 mL). Diphenyl phosphorylazide (0.47 mL, 2.181 mmol) was added and the reaction was heated at 90° C. for 3 days. The solution was partitioned between EtOAc (10 mL) and saturated aqueous sodium bicarbonate solution (10 mL), extracted with EtOAc (2×20 mL), dried over a hydrophobic frit and concentrated to give 1.08 g of a yellow solid. This was purified by chromatography on SiO₂ (Biotage® SNAP 25 g cartridge, eluting with 0-50% EtOAc/cyclohexane). The appropriate fractions were concentrated to give tert-butyl ((1S,2S)-2-methylcyclopropyl)carbamate (223 mg, 1.172 mmol, 58.7% yield) as a white crystalline solid.

$^1$H NMR (400 MHz, MeOH-d₄) δ ppm 2.05-2.14 (m, 1 H) 1.43 (br. s., 9 H) 1.04 (d, J=5.9 Hz, 3 H) 0.78 (m, J=8.9, 6.0, 6.0, 3.1 Hz, 1 H) 0.59 (dt, J=8.9, 4.3 Hz, 1 H) 0.39 (q, J=6.0 Hz, 1 H). Exchangeable proton not observed.

Intermediate 35: (1S,2S)-2-Methylcyclopropanamine hydrochloride

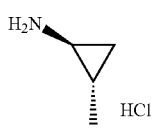

tert-Butyl ((1S,2S)-2-methylcyclopropyl)carbamate (215 mg, 1.26 mmol) was stirred at room temperature in 4 M HCl in dioxane (16 mL, 64.0 mmol). After 30 min, the solution was concentrated to give (1S,2S)-2-methylcyclopropanamine hydrochloride (151 mg, 1.123 mmol, 89% yield) as an off white solid.

$^1$H NMR (400 MHz, DMSO-d$_6$) δ ppm 8.27 (br. s., 3 H) 2.25 (br. s., 1 H) 1.06-1.18 (m, 1 H) 0.99 (d, J=6.1 Hz, 3 H) 0.85 (ddd, J=9.4, 5.6, 3.8 Hz, 1 H) 0.48 (dt, J=7.5, 5.9 Hz, 1 H).

Intermediate 36: (1R,5S,6R)-3-Oxabicyclo[3.1.0]hexane-6-carboxylic acid

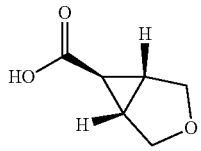

Lithium hydroxide (751 mg, 31.4 mmol) was added at rt to a solution of (1R,5S,6r)-ethyl 3-oxabicyclo[3.1.0]hexane-6-carboxylate (1.00 g, 6.27 mmol, commercially available from, for example, Pharmablock) in water (10 mL), THF (10 mL) and MeOH (10 mL). The resulting suspension was stirred 3 h at this temperature then was concentrated in vacuo. The residue was dissolved in a minimum amount of water, and treated with hydrochloric acid (5 mL, 25% w/w in water). The aqueous phase was extracted 4 times with MeOH/DCM and the combined organic phases were dried over a hydrophobic frit, concentrated in vacuo, to give (1R,5S,6r)-3-oxabicyclo[3.1.0]hexane-6-carboxylic acid (750 mg, 93%) which was used in the next step without further purification.

$^1$H NMR (400 MHz, DMSO-d$_6$) δ ppm 12.13 (s, 1 H) 3.80 (d, J=8.6 Hz, 2 H) 3.62 (d, J=8.6 Hz, 2 H) 2.00-2.15 (m, 2 H) 1.32 (t, J=3.1 Hz, 1 H)

Intermediate 37: Benzyl (1R,5S,6R)-3-oxabicyclo[3.1.0]hexan-6-ylcarbamate

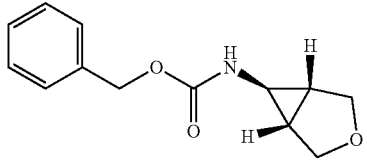 [SMILES: O=C(N[C@H]1[C@@H]2COC[C@@H]21)OCc1ccccc1]

A solution of (1R,5S,6r)-3-Oxabicyclo[3.1.0]hexane-6-carboxylic acid (340 mg, 2.65 mmol) in toluene (12 mL) at rt was treated with NEt$_3$ (1.11 mL, 7.96 mmol), diphenyl phosphorazidate (0.686 mL, 3.18 mmol) and benzyl alcohol (0.552 mL, 5.31 mmol) and the resulting mixture was heated at reflux for 2 h then was cooled to rt. The solution was diluted with EtOAc (10 mL) and washed with water (10 mL) and a sat. NaHCO$_3$ (aq) (10 mL). The organic phase was dried and evaporated and the residue purified by chomatography on a 25 g silica column eluting with 0-50% EtOAc:cyclohexane and the product-containing fractions were evaporated in vacuo to give benzyl (1R,5S,6r)-3-oxabicyclo[3.1.0]hexan-6-ylcarbamate (460 mg, 74%) as a white solid.

LCMS (Formic): Retention time 0.83 min, [M+H]$^+$=234.3.

Intermediate 38: (1R,5S,6R)-3-Oxabicyclo[3.1.0]hexan-6-amine, hydrochloride

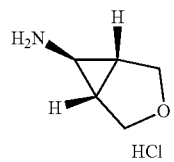

Benzyl (1R,5S,6r)-3-oxabicyclo[3.1.0]hexan-6-ylcarbamate (460 mg, 1.97 mmol) was dissolved in EtOH (20 mL) and the reaction was hydrogenated using an H-cube (settings: room temperature, 1 bar, 1 mL/min flow rate) and 10% Pd/C CatCart 30 as the catalyst. The reaction was cycled though the H-Cube for 1.5 h before acidifying the mixture with HCl (7M aqueous, 1.33 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 93%) as an off-white solid.

$^1$H NMR (400 MHz, DMSO-d6) δ ppm 8.48 (br. s., 3 H) 3.80 (d, J=8.8 Hz, 2 H) 3.59 (d, J=8.6 Hz, 2 H) 2.24 (t, J=2.3 Hz, 1 H) 2.07 (t, J=2.6 Hz, 2 H).

EXAMPLES

Example 1

N$^5$-cyclopropyl-3-(1H-indol-4-yl)-N$^7$-methyl-2,3-dihydrobenzofuran-5,7-dicarboxamide

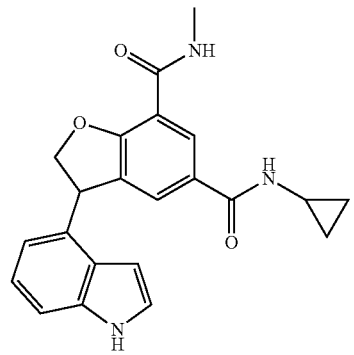 [SMILES: CNC(=O)c1cc(C(=O)NC2CC2)cc2c1OCC2c1cccc2[nH]ccc12]

3-(1H-indol-4-yl)-7-(methylcarbamoyl)-2,3-dihydrobenzofuran-5-carboxylic acid (For a preparation see Intermediate 20, 86 mg, 0.26 mmol) was taken up in dichloromethane (3 mL). DIPEA (0.134 mL, 0.767 mmol), cyclopropanamine (0.021 mL, 0.31 mmol) and 2,4,6-tripropyl-1,3,5,2,4,6-trioxatriphosphinane 2,4,6-trioxide (0.091 mL, 0.31 mmol) were added and the reaction left to stir at room temperature overnight. Saturated aqueous sodium bicarbonate (10 mL) was added to the reaction mixture before being extracted with DCM (3×5 mL). The organic phase was dried through a hydrophobic frit and concentrated in vacuo. the reaction was triturated in diethyl ether (10 mL) before being filtered to give the title compound (54 mg, 0.144 mmol, 56.3% yield).

LCMS (Formic): Rt: 0.86 min, [MH]$^+$=376.3

The following Example (Example 2) was prepared by a similar method to Example 1:

| Example number | Name and Structure | [MH+] | Rt (min) |
|---|---|---|---|
| 2 | 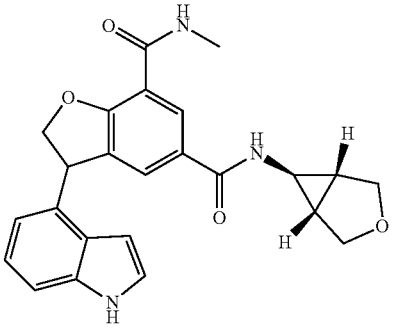<br>(+/-)-N⁵-((1R,5S,6r)-3-Oxabicyclo[3.1.0]hexan-6-yl)-3-(1H-indol-4-yl)-N⁷-methyl-2,3-dihydrobenzofuran-5,7-dicarboxamide | 418.3 | 0.83 (formic) |

Example 3

N⁵-(2-(1H-pyrazol-5-yl)ethyl)-N⁷-methyl-3-phenyl-2,3-dihydrobenzofuran-5,7-dicarboxamide

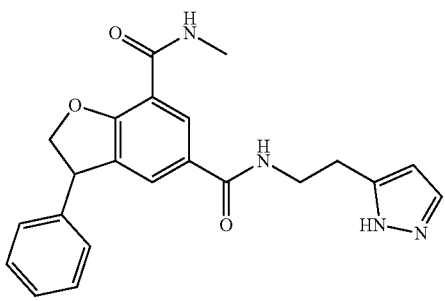 [SMILES: CNC(=O)c1cc(C(=O)NCCc2ccn[nH]2)cc2c1OCC2c1ccccc1]

HATU (77 mg, 0.202 mmol) was added to a solution of 7-(methylcarbamoyl)-3-phenyl-2,3-dihydrobenzofuran-5-carboxylic acid (For a preparation see Intermediate 7, 40 mg, 0.135 mmol), 2-(1H-pyrazol-5-yl)ethanamine (17.94 mg, 0.161 mmol) and DIPEA (0.047 mL, 0.269 mmol) in N,N-dimethylformamide (4 mL). The reaction mixture was stirred for 1 hour, then partitioned between EtOAc (25 mL) and water (30 mL). The organic layer was washed (1× water 20 mL, 2× sat. aq. NaHCO₃ 20 mL), passed through a hydrophobic frit and evaporated in vacuo. The sample was purified by silica gel column chromatography, eluting with a gradient of EtOAc:EtOH (0-10%). The product containing fractions were combined and the solvent removed in vacuo. The sample was then dried under a stream of Nitrogen for 1 hour to give the title compound (17 mg, 0.041 mmol, 30.7% yield) as a clear oil/white solid.

LCMS (Formic): Rt: 0.82 min, [MH]⁺=391.4

The following Examples (4-44) were made by a similar method to Example 3:

| Example number | Name and Structure | [MH+] | Rt (min) |
|---|---|---|---|
| 4 | 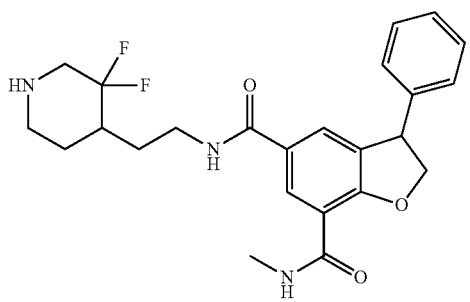<br>N⁵-(2-(3,3-difluoropiperidin-4-yl)ethyl)-N⁷-methyl-3-phenyl-2,3-dihydrobenzofuran-5,7-dicarboxamide | 444.2 | 0.61 (Formic) |

-continued

| Example number | Name and Structure | [MH+] | Rt (min) |
|---|---|---|---|
| 5 | 3-(4-fluorophenyl)-N⁷-methyl-N⁵-(2-(1-methyl-1H-pyrazol-4-yl)ethyl)-2,3-dihydrobenzofuran-5,7-dicarboxamide | 423.4 | 0.89 (High pH) |
| 6 | N⁷-methyl-3-phenyl-N⁵-(pyridin-4-yl)-2,3-dihydrobenzofuran-5,7-dicarboxamide formate | 374.1 | 0.62 (Formic) |
| 7 | N⁵-(1-(2-hydroxyethyl)-1H-pyrazol-4-yl)-N⁷-methyl-3-phenyl-2,3-dihydrobenzofuran-5,7-dicarboxamide | 407.1 | 0.81 (Formic) |

-continued
| Example number | Name and Structure | [MH+] | Rt (min) |
|---|---|---|---|
| 8 | 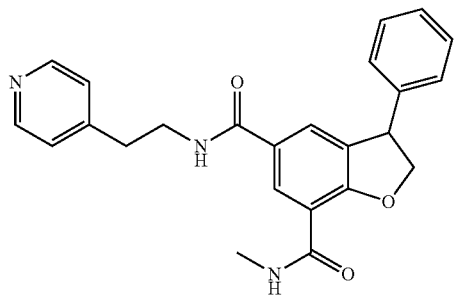<br>N7-methyl-3-phenyl-N5-(2-(pyridin-4-yl)ethyl)-2,3-dihydrobenzofuran-5,7-dicarboxamide | 402.1 | 0.59 (Formic) |
| 9 | 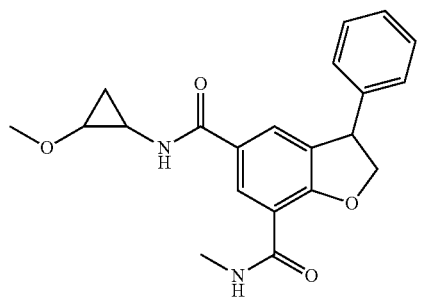<br>N5-(2-methoxycyclopropyl)-N7-methyl-3-phenyl-2,3-dihydrobenzofurna-5,7-dicarboxamide | 367.1 | 0.90 (Formic) |
| 10 | 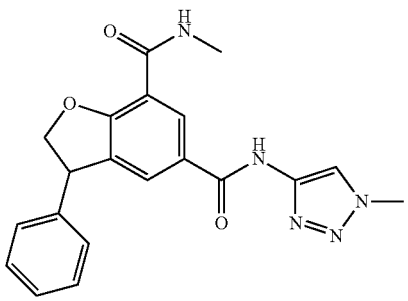<br>N7-methyl-N5-(1-methyl-1H-1,2,3-triazol-4-yl)-3-phenyl-2,3-dihydrobenzofuran-5,7-dicarboxamide | 378.1 | 0.86 (Formic) |

| Example number | Name and Structure | [MH+] | Rt (min) |
|---|---|---|---|
| 11 | 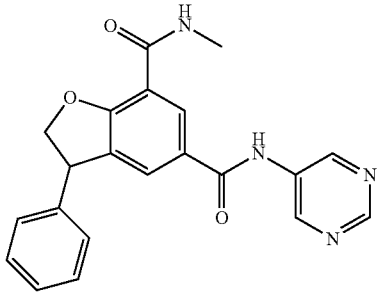<br>N7-methyl-3-phenyl-N5-(pyrimidin-5-yl)-2,3-dihydrobenzofuran-5,7-dicarboxamide | 375.1 | 0.87 (Formic) |
| 12 | 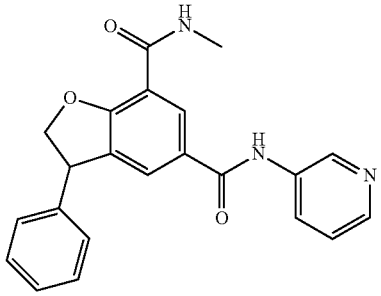<br>N7-methyl-3-phenyl-N5-(pyridin-3-yl)-2,3-dihydroxbenzofuran-5,7-dicarboxamide | 374.1 | 0.70 (Formic) |
| 13 | 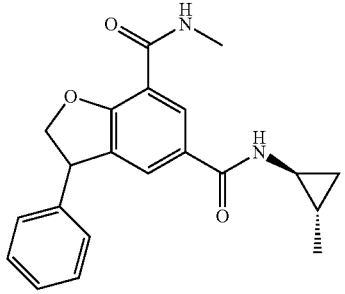<br>N7-methyl-N5-((1S,2S)-2-methylcyclopropyl)-3-phenyl-2,3-dihydrobenzofuran-5,7-dicarboxamide | 351.4 | 0.99 (Formic) |

| Example number | Name and Structure | [MH+] | Rt (min) |
|---|---|---|---|
| 14 | 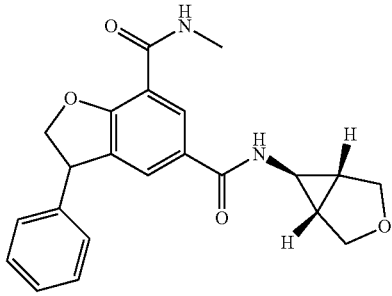<br>N5-((1R,5S,6r)-3-oxabicyclo[3.1.0]hexan-6-yl)-N7-methyl-3-phenyl-2,3-dihydrobenzofuran-5,7-dicarboxamide | 379.3 | 0.87 (Formic) |
| 15 | 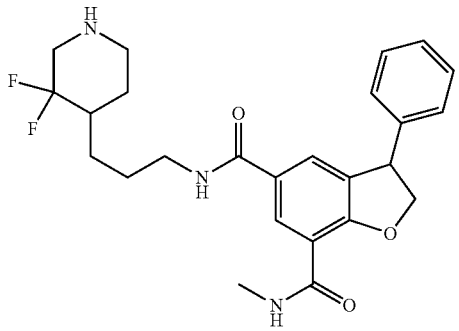<br>N5-(3-(3,3-difluoropiperidin-4-yl)propyl)-N7-methyl-3-phenyl-2,3-dihydrobenzofuran-5,7-dicarboxamide | 458.2 | 0.63 (Formic) |
| 16 | 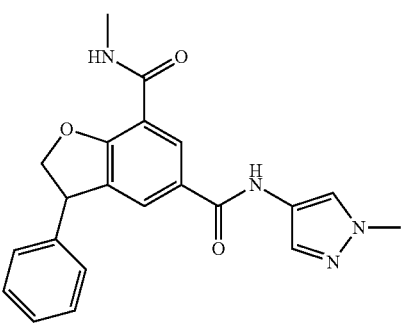<br>(+/-)-N7-methyl-N5-(1-methyl-1H-pyrazol-4-yl)-3-phenyl-2,3-dihydrobenzofuran-5,7-dicarboxamide | 377.1 | 0.87 (Formic) |

-continued
| Example number | Name and Structure | [MH+] | Rt (min) |
|---|---|---|---|
| 17 | 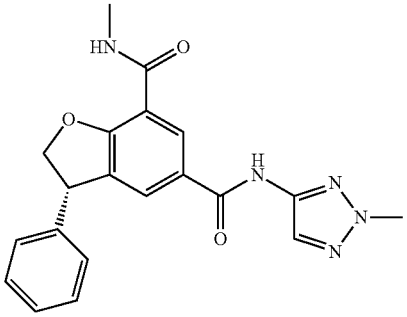 (S*)-N7-methyl-N5-(2-methyl-2H-1,2,3-triazol-4-yl)-3-phenyl-2,3-dihydrobenzofuran-5,7-dicarboxamide | 378.3 | 0.92 (Formic) |
| 18 | 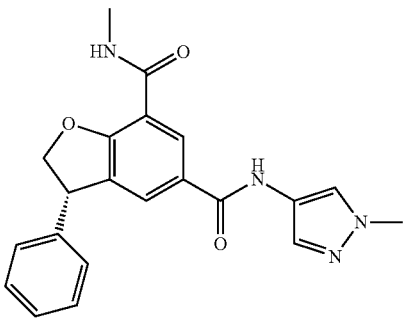 (S*)-N7-methyl-N5-(2-methyl-1H-pyrazol-4-yl)-3-phenyl-2,3-dihydrobenzofuran-5,7-dicarboxamide | 377.3 | 0.88 (Formic) |
| 19 | 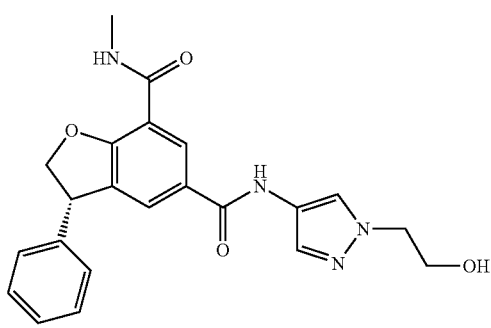 (S*)-N5-(1-(2-hydroxyethyl)-1H-pyrazol-4-yl)-N7-methyl-3-phenyl-2,3-dihydrobenzofuran-5,7-dicarboxamide | 407.3 | 0.82 (Formic) |

-continued
| Example number | Name and Structure | [MH⁺] | Rt (min) |
|---|---|---|---|
| 20 | 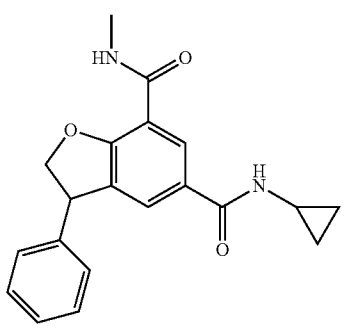<br>(+/-)-N⁵-cyclopropyl-N⁷-methyl-3-phenyl-2,3-dihydrobenzofuran-5,7-dicarboxamide | 337.1 | 0.91 (Formic) |
| 21 | 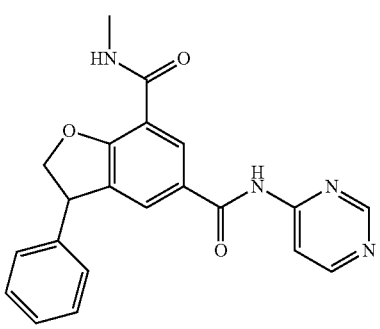<br>(+/-)-N⁷-methyl-3-phenyl-N⁵-(pyrimidin-4-yl)-2,3-dihydrobenzofuran-5,7-dicarboxamide | 375.1 | 0.90 (Formic) |
| 22 | 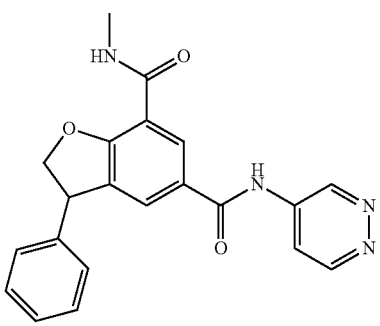<br>(+/-)-N⁷-methyl-3-phenyl-N⁵-(pyridazin-4-yl)-2,3-dihydrobenzofuran-5,7-dicarboxamide | 375.1 | 0.79 (Formic) |

| Example number | Name and Structure | [MH+] | Rt (min) |
|---|---|---|---|
| 23 | 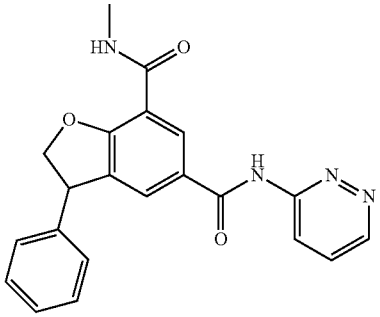
(+/-)-N⁷-methyl-3-phenyl-N⁵-(pyridazin-3-yl)-2,3-dihydrobenzofuran-5,7-dicarboxamide | 375.1 | 0.88 (Formic) |
| 24 | 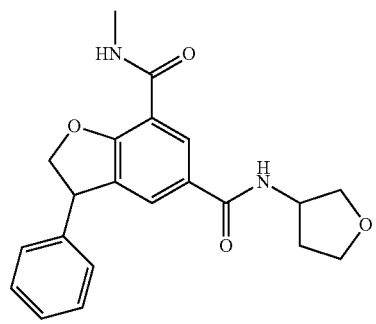
(+/-)-N⁷-methyl-3-phenyl-N⁵-(tetrahydrofuran-3-yl)-2,3-dihydrobenzofuran-5,7-dicarboxamide | 367.1 | 0.85 (Formic) |
| 25 | 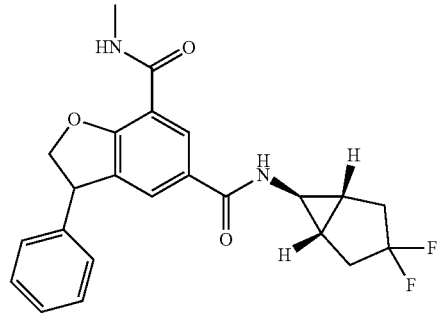
(+/-)-N⁵-((1R,5S,6r)-3,3-difluorobicyclo[3.1.0]hexan-6-yl)-N⁷-methyl-3-phenyl-2,3-dihydrobenzofuran-5,7-dicarboxamide | 413.1 | 1.03 (Formic) |

| Example number | Name and Structure | [MH+] | Rt (min) |
|---|---|---|---|
| 26 | 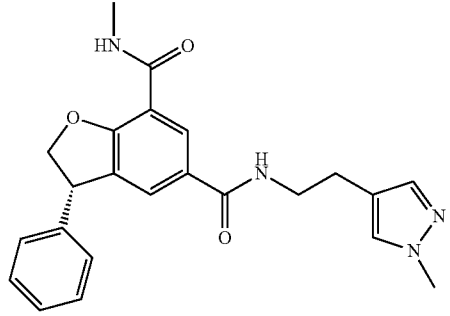(S*)-N7-methyl-N5-(2-(1-methyl-1H-pyrazol-4-yl)ethyl)-3-phenyl-2,3-dihydrobenzofuran-5,7-dicarboxamide | 405.4 | 0.87 (Formic) |
| 27 | 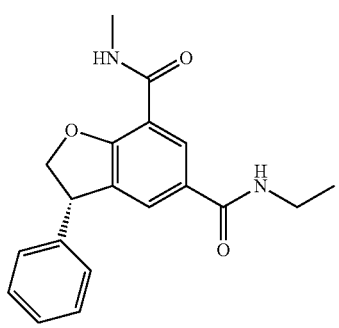(S*)-N5-ethyl-N7-methyl-3-phenyl-2,3-dihydrobenzofuran-5,7-dicarboxamide | 325.2 | 0.90 (Formic) |
| 28 | 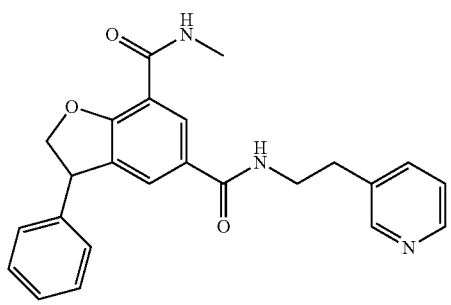(+/-)-N7-methyl-3-phenyl-N5-(2-(pyridin-3-yl)ethyl)-2,3-dihydrobenzofuran-5,7-dicarboxamide | 402 | 0.60 (formic) |

| Example number | Name and Structure | [MH+] | Rt (min) |
|---|---|---|---|
| 29 | (+/-)-N⁷-methyl-N⁵-(1-(methylsulfonyl)azetidin-3-yl)-3-phenyl-2,3-dihydrobenzofuran-5,7-dicarboxamide | 430 | 0.87 (formic) |
| 30 | (+/-) N⁵-(2-(1H-imidazol-4-yl)ethyl)-N⁷-methyl-3-phenyl-2,3-dihydrobenzofuran-5,7-dicarboxamide | 391 | 0.57 (formic) |
| 31 | (+/-) N⁷-methyl-3-phenyl-N⁵-((tetrahydrofuran-3-yl)methyl)-2,3-dihydrobenzofuran-5,7-dicarboxamide | 381 | 0.87 (formic) |

| Example number | Name and Structure | [MH+] | Rt (min) |
|---|---|---|---|
| 32 | (+/-) N7-methyl-N5-((1-methyl-1H-pyrazol-4-yl)methyl)-3-phenyl-2,3-dihydrobenzofuran-5,7-dicarboxamide | 391 | 0.83 (formic) |
| 33 | (+/-) N5-(3-methoxypropyl)-N7-methyl-3-phenyl-2,3-dihydrobenzofuran-5,7-dicarboxamide | 369 | 0.89 (formic) |
| 34 | (+/-) N7-methyl-3-phenyl-N5-(tetrahydro-2H-pyran-4-yl)-2,3-dihydrobenzofuran-5,7-dicarboxamide | 381 | 0.87 (formic) |

| Example number | Name and Structure | [MH+] | Rt (min) |
|---|---|---|---|
| 35 | (+/-) $N^5$-(2-methoxyethyl)-$N^7$-methyl-3-phenyl-2,3-dihydrobenzofuran-5,7-dicarboxamide | 355 | 0.85 (formic) |
| 36 | (+/-) $N^7$-methyl-$N^5$-(3-methyl-1H-pyrazol-4-yl)-3-phenyl-2,3-dihydrobenzofuran-5,7-dicarboxamide | 377 | 0.81 (formic) |
| 37 | (+/-) $N^7$-methyl-$N^5$-(1-methyl-1H-1,2,4-triazol-3-yl)-3-phenyl-2,3-dihydrobenzofuran-5,7-dicarboxamide | 378 | 0.76 (formic) |

| Example number | Name and Structure | [MH+] | Rt (min) |
|---|---|---|---|
| 38 | 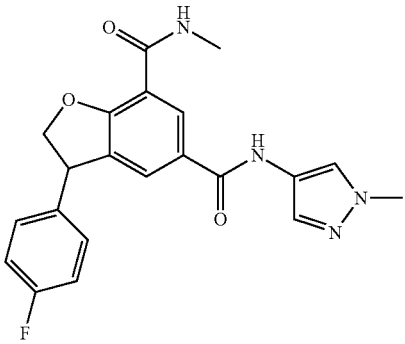<br>(+/-) 3-(4-Fluorophenyl)-N⁷-methyl-N⁵-(1-methyl-1H-pyrazol-4-yl)-2,3-dihydrobenzofuran-5,7-dicarboxamide | 395 | 0.89 (HpH) |
| 39 | 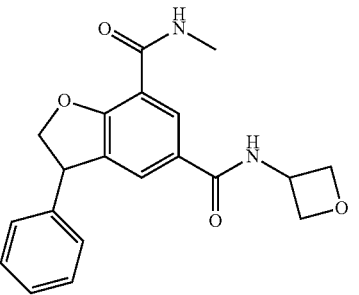<br>(+/-) N⁷-Methyl-N⁵-(oxetan-3-yl)-3-phenyl-2,3-dihydrobenzofuran-5,7-dicarboxamide | 353.1 | 0.82 (formic) |
| 40 | 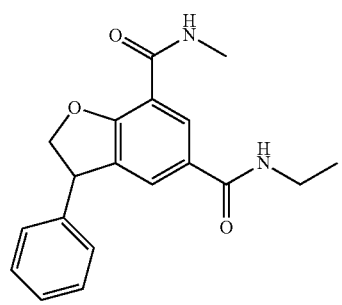<br>(+/-) N⁵-Ethyl-N⁷-methyl-3-phenyl-2,3-dihydrobenzofuran-5,7-dicarboxamide | 325.1 | 0.89 (formic) |

| Example number | Name and Structure | [MH+] | Rt (min) |
|---|---|---|---|
| 41 | 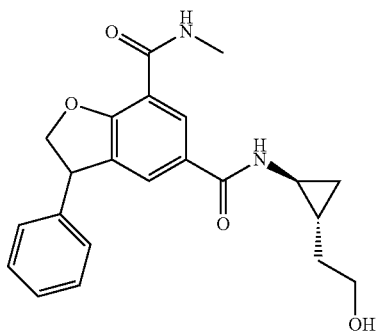<br>(+/-) N5-((trans)-2-(2-Hydroxyethyl)cyclopropyl)-N7-methyl-3-phenyl-2,3-dihydrobenzofuran-5,7-dicarboxamide | 381.1 | 0.88 (formic) |
| 42 | 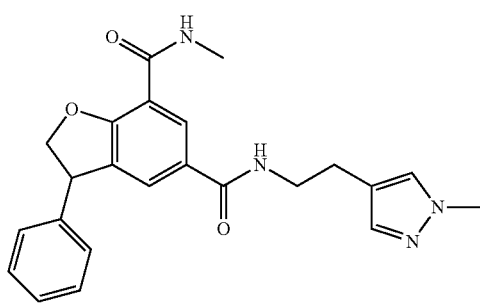<br>(+/-) N7-Methyl-N5-(2-(1-methyl-1H-pyrazol-4-yl)ethyl)-3-phenyl-2,3-dihydrobenzofuran-5,7-dicarboxamide | 405.1 | 0.85 (formic) |
| 43 | 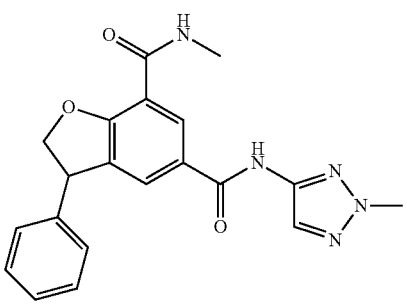<br>(+/-) N7-Methyl-N5-(2-methyl-2H-1,2,3-triazol-4-yl)-3-phenyl-2,3-dihydrobenzofuran-5,7-dicarboxamide | 378.1 | 0.92 (formic) |

| Example number | Name and Structure | [MH⁺] | Rt (min) |
|---|---|---|---|
| 44 | (S)-N⁷-methyl-3-phenyl-N⁵-(pyrimidin-5-yl)-2,3-dihydrobenzofuran-5,7-dicarboxamide | 375.3 | 0.88 (formic) |

Example 45

(S*)-3-(4-fluorophenyl)-N⁷-methyl-N⁵-(2-(1-methyl-1H-pyrazol-4-yl)ethyl)-2,3-dihydrobenzofuran-5,7-dicarboxamide

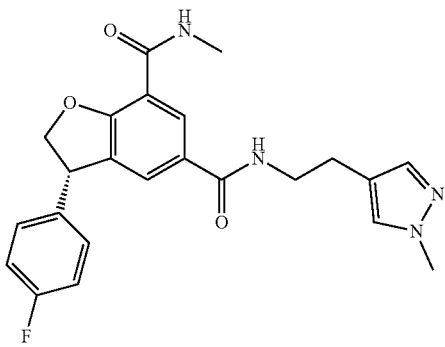 [SMILES: CNC(=O)c1cc(C(=O)NCCc2cnn(C)c2)cc2c1OC[C@H]2c1ccc(F)cc1]

A sample of 3-(4-fluorophenyl)-N⁷-methyl-N⁵-(2-(1-methyl-1H-pyrazol-4-yl)ethyl)-2,3-dihydrobenzofuran-5,7-dicarboxamide (for a preparation see Example 5, 81 mg) was purified by chiral chromatography using the following conditions:

Sample dissolved in 3 mL EtOH.

Injection; 1.5 mL of the solution was injected onto the column per run.

Solvents used: 60% EtOH/Heptane, flowrate=20 ml/min, detection wavelength, 215 nm Column: 21.1 mmid×25 cm (R-R) Whelk O-1 Lot No #49788

The fractions containing the first eluting isomer were collected and concentrated to dryness by rotary evaporation to give the title compound (34.8 mg)

LCMS (High ph): Rt: 0.89 min, [MH]⁺=423.4

The following Examples (46-64) were prepared by a similar method to Example 45:

| Example number | | [MH⁺] | Rt (min) |
|---|---|---|---|
| 46 | (S*)-3-(1H-indol-4-yl)-N⁷-methyl-N⁵-(2-(1-methyl-1H-pyrazol-4-ypethyl)-2,3-dihydrobenzofuran-5,7-dicarboxamide | 444.4 | 0.83 (Formic) |

| Example number | | [MH+] | Rt (min) |
|---|---|---|---|
| 47 | 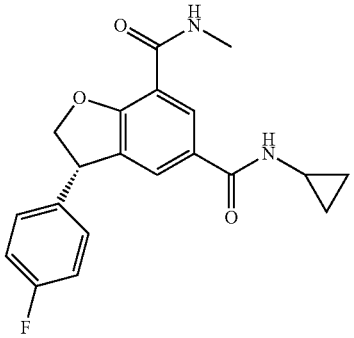 (S*)-N5-cyclopropyl-3-(4-fluorophenyl)-N7-methyl-2,3-dihydrobenzofuran-5,7-dicarboxamide | 355.3 | 0.92 (High pH) |
| 48 | 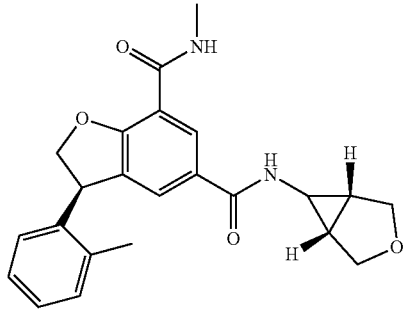 [SMILES: CNC(=O)c1cc(C(=O)NC2[C@H]3COC[C@@H]23)cc2c1OC[C@@H]2c1ccccc1C] (R*)-N5-((1R,5S,6r)-3-oxabicyclo[3.1.0]hexan-6-yl)-N7-methyl-3-(o-tolyl)-2,3-dihydrobenzofuran-5,7-dicarboxamide | 393.3 | 0.93 (Formic) |
| 49 | 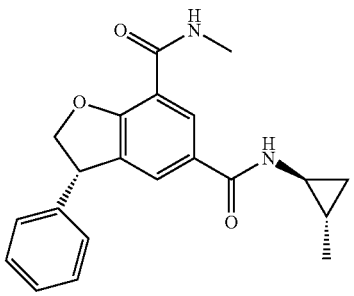 [SMILES: CNC(=O)c1cc(C(=O)N[C@H]2C[C@@H]2C)cc2c1OC[C@H]2c1ccccc1] (S*)-N7-methyl-N5-((1S,2S)-2-methylcyclopropyl)-3-phenyl-2,3-dihydrobenzofuran-5,7-dicarboxamide | 351.3 | 0.98 (Formic) |
| 50 | 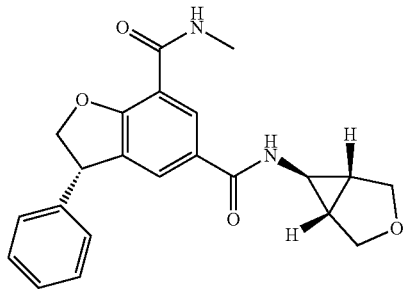 [SMILES: CNC(=O)c1cc(C(=O)N[C@H]2[C@@H]3COC[C@@H]32)cc2c1OC[C@H]2c1ccccc1] (S*)-N5-((1R,5S,6r)-3-oxabicyclo[3.1.0]hexan-6-yl)-N7- | 379.3 | 0.87 (Formic) |

| Example number | | [MH⁺] | Rt (min) |
|---|---|---|---|
| | methyl-3-phenyl-2,3-dihydrobenzofuran-5,7-dicarboxamide | | |
| 51 | 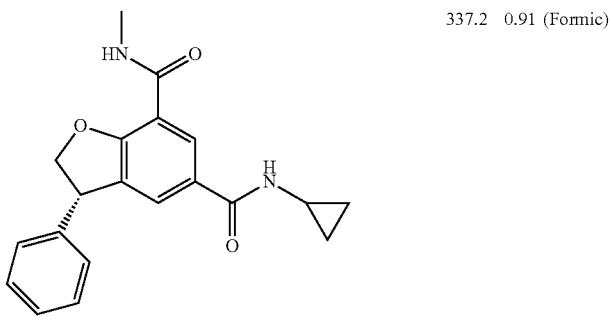<br>(S*)-N⁵-cyclopropyl-N⁷-methyl-3-phenyl-2,3-dihydrobenzofuran-5,7-dicarboxamide | 337.2 | 0.91 (Formic) |
| 52 | 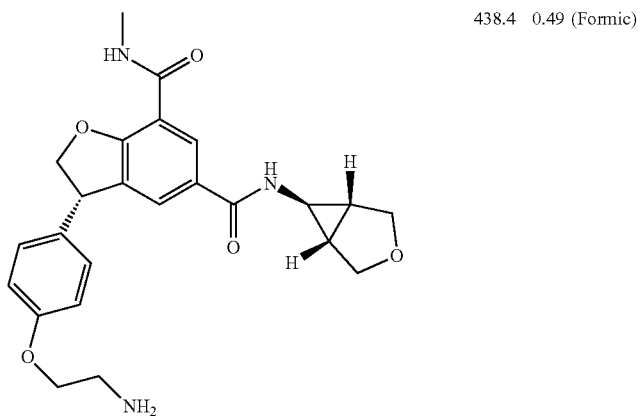<br>(S*)-3-(4-(2-aminoethoxy)phenyl)-N⁵-((1R,5S,6r)-3-oxabicyclo[3.1.0]hexan-6-yl)-N⁷-methyl-2,3-dihydrobenzofuran-5,7-dicarboxamide | 438.4 | 0.49 (Formic) |
| 53 | 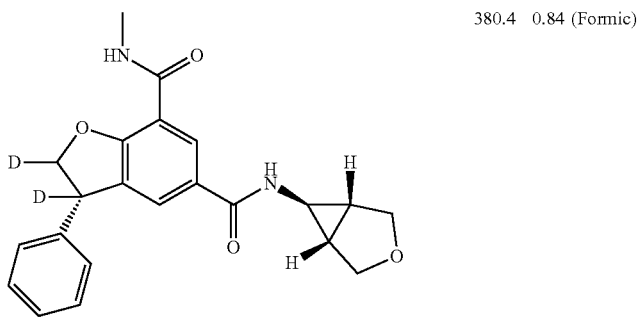<br>(S*)-N⁵-((1R,5S,6r)-3-oxabicyclo[3.1.0]hexan-6-yl)-N⁷-methyl-3-phenyl-2,3-dihydrobenzofuran-5,7-dicarboxamide | 380.4 | 0.84 (Formic) |

-continued
| Example number | | [MH+] | Rt (min) |
|---|---|---|---|
| 54 | 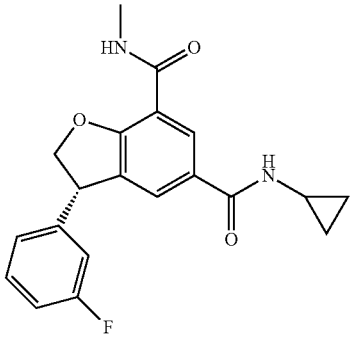 [SMILES: CNC(=O)c1cc(C(=O)NC2CC2)cc2c1OC[C@H]2c1cccc(F)c1] (S*)-N5-cyclopropyl-3-(3-fluorophenyl)-N7-methyl-2,3-dihydrobenzofuran-5,7-dicarboxamide | 355.2 | 0.93 (Formic) |
| 55 | 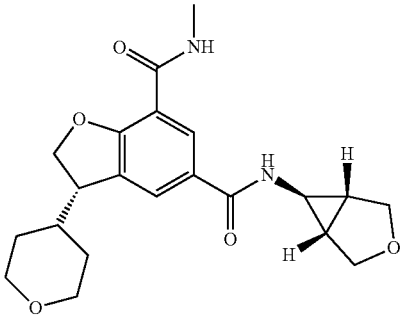 [SMILES: CNC(=O)c1cc(C(=O)N[C@H]2[C@@H]3COC[C@@H]32)cc2c1OC[C@H]2C1CCOCC1] (S*)-N5-((1R,5S,6r)-3-oxabicyclo[3.1.0]hexan-6-yl)-N7-methyl-3-(tetrahydro-2H-pyran-4-yl)-2,3-dihydrobenzofuran-5,7-dicarboxamide | 387 | 0.69 (formic) |
| 56 | 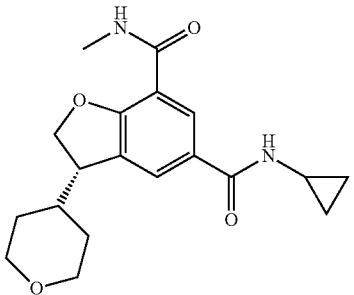 [SMILES: CNC(=O)c1cc(C(=O)NC2CC2)cc2c1OC[C@H]2C1CCOCC1] (S*)-N5-cyclopropyl-N7-methyl-3-(tetrahydro-2H-pyran-4-yl)-2,3-dihydrobenzofuran-5,7-dicarboxamide | 345 | 0.71 (formic) |
| 57 | 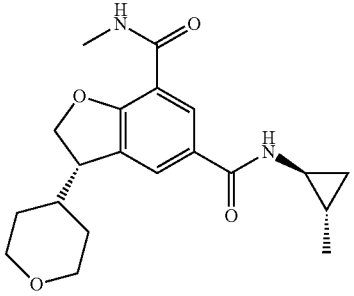 [SMILES: CNC(=O)c1cc(C(=O)N[C@H]2C[C@@H]2C)cc2c1OC[C@H]2C1CCOCC1] | 359 | 0.80 (formic) |

| Example number | | [MH+] | Rt (min) |
|---|---|---|---|
| | (S*)-N7-methyl-N5-((1S,2S)-2-methylcyclopropyl)-3-(tetrahydro-2H-pyran-4-yl)-2,3-dihydrobenzofuran-5,7-dicarboxamide | | |
| 58 | 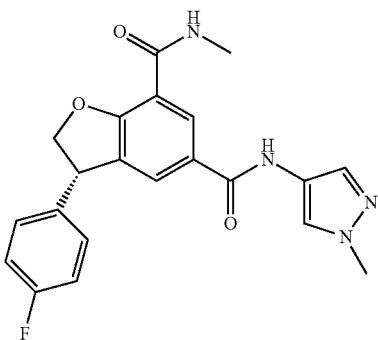 [SMILES: CNC(=O)c1cc(C(=O)Nc2cnn(C)c2)cc2c1OC[C@H]2c1ccc(F)cc1] (S*)-3-(4-fluorophenyl)-N7-methyl-N5-(1-methyl-1H-pyrazol-4-yl)-2,3-dihydrobenzofuran-5,7-dicarboxamide | 395 | 0.90 (HpH) |
| 59 | 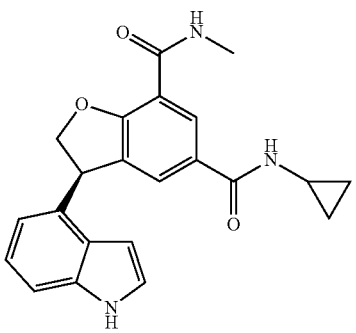 [SMILES: CNC(=O)c1cc(C(=O)NC2CC2)cc2c1OC[C@@H]2c1cccc2[nH]ccc12] (R*)-N5-Cyclopropyl-3-(1H-indol-4-yl)-N7-methyl-2,3-dihydrobenzofuran-5,7-dicarboxamide | 376.3 | 0.86 (formic) |
| 60 | 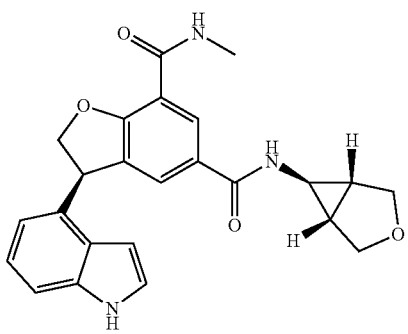 [SMILES: CNC(=O)c1cc(C(=O)N[C@H]2[C@@H]3COC[C@@H]32)cc2c1OC[C@@H]2c1cccc2[nH]ccc12] (R*)-N5-((1R,5S,6r)-3-Oxabicyclo[3.1.0]hexan-6-yl)-3-(1H-indol-4-yl)-N7-methyl-2,3-dihydrobenzofuran-5,7-dicarboxamide | 418.3 | 0.84 (formic) |

-continued
| Example number | | [MH+] | Rt (min) |
|---|---|---|---|
| 61 | 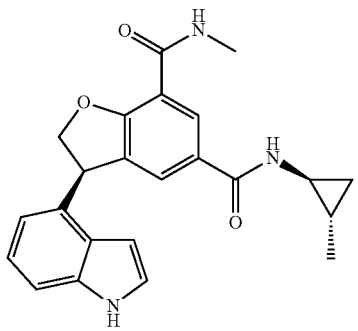 [SMILES: CNC(=O)c1cc(C(=O)N[C@H]2C[C@@H]2C)cc2c1OC[C@@H]2c1cccc2[nH]ccc12]<br>(R*)-3-(1H-Indol-4-yl)-N⁷-methyl-N⁵-((1S,2S)-2-methylcyclopropyl)-2,3-dihydrobenzofuran-5,7-dicarboxamide | 390.3 | 0.94 (formic) |
| 62 | 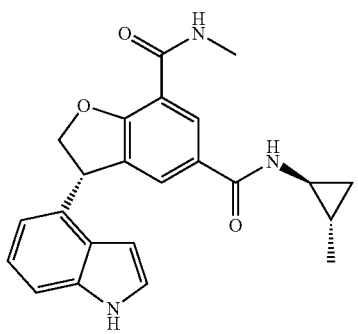 [SMILES: CNC(=O)c1cc(C(=O)N[C@H]2C[C@@H]2C)cc2c1OC[C@H]2c1cccc2[nH]ccc12]<br>(S*)-3-(1H-Indol-4-yl)-N⁷-methyl-N⁵-((1S,2S)-2-methylcyclopropyl)-2,3-dihydrobenzofuran-5,7-dicarboxamide | 390.4 | 0.94 (formic) |
| 63 | 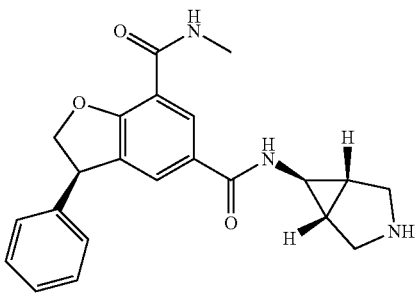 [SMILES: CNC(=O)c1cc(C(=O)N[C@H]2[C@@H]3CNC[C@@H]32)cc2c1OC[C@@H]2c1ccccc1]<br>(R*)-N⁵-((1R,5S,6s)-3-Azabicyclo[3.1.0]hexan-6-yl)-N⁷-methyl-3-phenyl-2,3-dihydrobenzofuran-5,7-dicarboxamide | 378.4 | 0.55 (formic) |

| Example number | | [MH+] | Rt (min) |
|---|---|---|---|
| 64 | 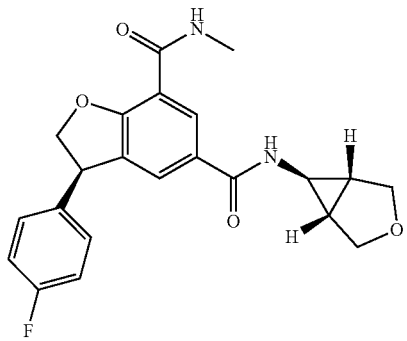 [SMILES: CNC(=O)c1cc(C(=O)N[C@H]2[C@@H]3COC[C@@H]32)cc2c1OC[C@@H]2c1ccc(F)cc1] (R*)-N5-((1R,5S,6r)-3-Oxabicyclo[3.1.0]hexan-6-yl)-3-(4-fluorophenyl)-N7-methyl-2,3-dihydrobenzofuran-5,7-dicarboxamide | 397.3 | 0.89 (formic) |

Example 65

$N^5$-cyclopropyl-$N^7$-methyl-3-(1-methyl-1H-indol-4-yl)-2,3-dihydrobenzofuran-5,7-dicarboxamide

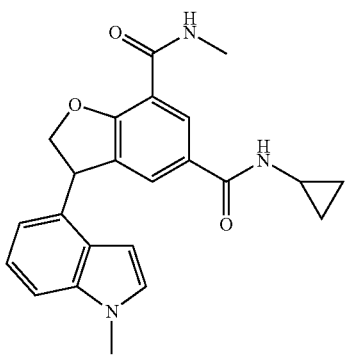 [SMILES: CNC(=O)c1cc(C(=O)NC2CC2)cc2c1OCC2c1cccc2c1ccn2C]

$N^5$-cyclopropyl-$N^7$-methyl-3-(1-methyl-1H-indol-4-yl)benzofuran-5,7-dicarboxamide (For a preparation see Intermediate 22, 98 mg, 0.253 mmol) was dissolved in Ethanol (25 mL) and added to a hydrogenation flask with 5% w/w palladium on activated carbon paste (100 mg, 0.047 mmol). The reaction mixture was stirred under an atmosphere of hydrogen for 16 hr. The reaction mixture was eluted through a 10 g celite column with EtOAc, MeOH and 2-MeTHF and concentrated in vacuo. The residue was dissolved in ethanol (20 ml) and added to a hydrogenation flask with 5% w/w palladium on activated carbon paste (100 mg, 0.047 mmol). The reaction mixture was stirred under an atmosphere of hydrogen at rt for a further 16 hr. The reaction mixture was eluted through a 10 g celite column with EtOAc, MeOH and 2-MeTHF and concentrated in vacuo. The residue was dissolved in ethanol (20 mL) and added to a hydrogenation flask with 5% w/w palladium on activated carbon paste (100 mg, 0.047 mmol). The reaction mixture was stirred under an atmosphere of hydrogen at rt for 16 hr. The reaction mixture was eluted through a 10 g celite column with EtOAc, MeOH and 2-MeTHF and concentrated in vacuo. The residue was diluted with water and extracted with EtOAc. The organics were dried via a hydrophobic frit and concentrated in vacuo. The residue was taken up in DCM (~5 ml), charged to 10 g silica gel column and eluted with a gradient of 0-70% [25% EtOH in EtOAc]:cyclohexane. The relevant fractions were combined and concentrated in vacuo. The residue was taken up in DMSO:MeOH (1 ml) and purified by MDAP (high pH method). The relevant fractions were combined and concentrated in vacuo to give the title compound (21 mg, 0.054 mmol, 21.32% yield) as a white solid.

LCMS (Formic): Rt: 0.97 min, [MH]+=390.4

The following Examples (66-79) were prepared by a similar method to Example 65:

| Example number | Name and Structure | [MH+] | Rt (min) |
|---|---|---|---|
| 66 | 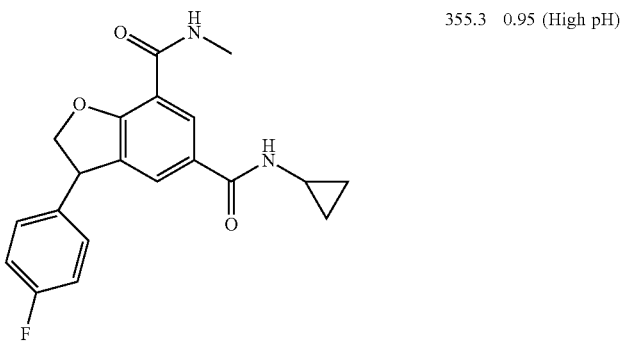<br>N5-cyclopropyl-3-(4-fluorophenyl)-N7-methyl-2,3-dihydrobenzofuran-5,7-dicarboxamide | 355.3 | 0.95 (High pH) |
| 67 | 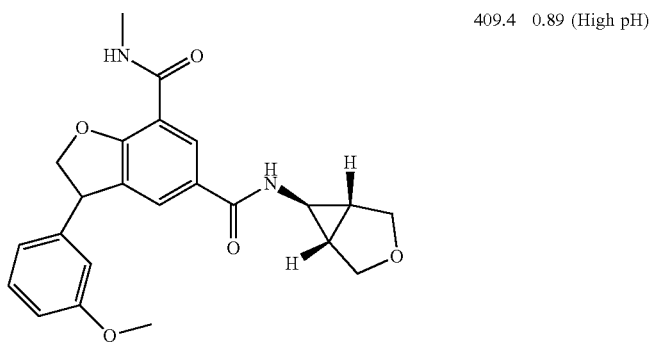<br>N5-((1R,5S,6r)-3-oxabicyclo[3.1.0]hexan-6-yl)-3-(3-methoxyphenyl)-N7-methyl-2,3-dihydrobenzofuran-5,7-dicarboxamide | 409.4 | 0.89 (High pH) |
| 68 | 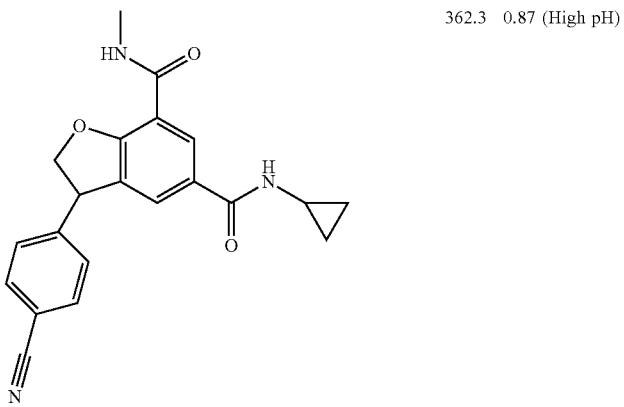<br>3-(4-cyanophenyl)-N5-cyclopropyl-N7-methyl-2,3-dihydrobenzofuran-5,7-dicarboxamide | 362.3 | 0.87 (High pH) |

-continued
| Example number | Name and Structure | [MH+] | Rt (min) |
|---|---|---|---|
| 69 | 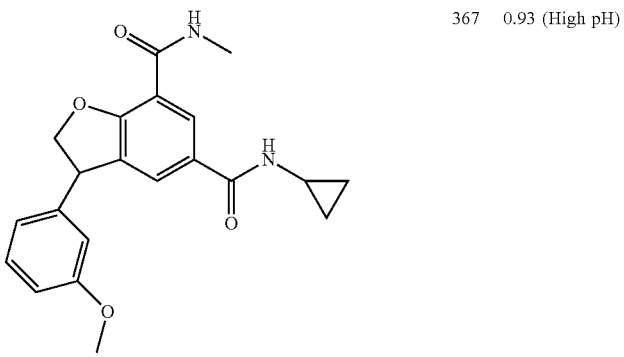<br>(+/−) N⁵-cyclopropyl-3-(3-methoxyphenyl)-N⁷-methyl-2,3-dihydrobenzofuran-5,7-dicarboxamide | 367 | 0.93 (High pH) |
| 70 | 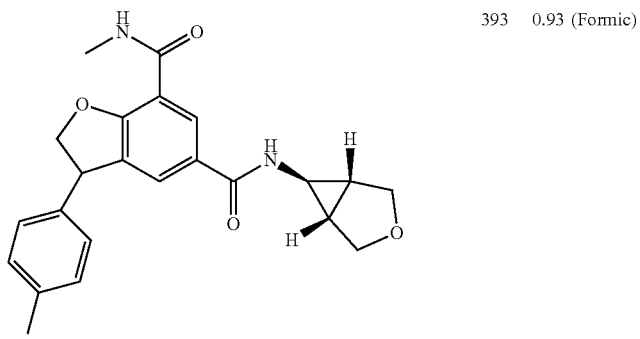<br>(+/−) N⁵-((1R,5S,6r)-3-oxabicyclo[3.1.0]hexan-6-yl)-N⁷-methyl-3-(p-tolyl)-2,3-dihydrobenzofuran-5,7-dicarboxamide | 393 | 0.93 (Formic) |
| 71 | 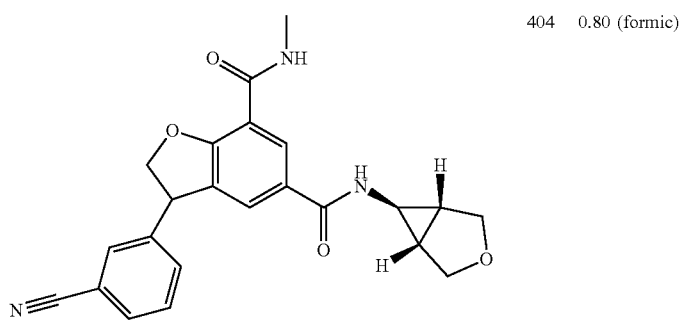<br>(+/−) N⁵-((1R,5S,6r)-3-oxabicyclo[3.1.0]hexan-6-yl)-3-(3-cyanophenyl)-N⁷-methyl-2,3-dihydrobenzofuran-5,7-dicarboxamide | 404 | 0.80 (formic) |

-continued
| Example number | Name and Structure | [MH+] | Rt (min) |
|---|---|---|---|
| 72 | 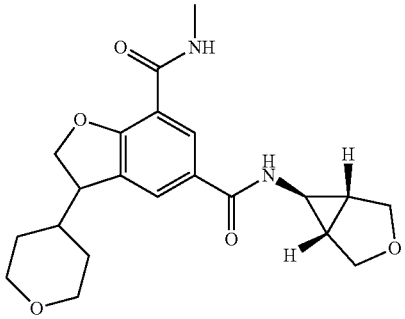 [SMILES: CNC(=O)c1cc(C(=O)N[C@H]2[C@@H]3COC[C@@H]32)cc2c1OCC2C1CCOCC1]
(+/−) N⁵-((1R,5S,6r)-3-oxabicyclo[3.1.0]hexan-6-yl)-N⁷-methyl-3-(tetrahydro-2H-pyran-4-yl)-2,3-dihydrobenzofuran-5,7-dicarboxamide | 387 | 0.68 (formic) |
| 73 | 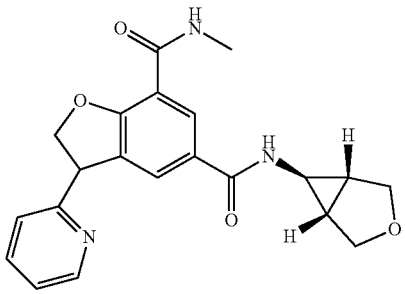 [SMILES: CNC(=O)c1cc(C(=O)N[C@H]2[C@@H]3COC[C@@H]32)cc2c1OCC2c1ccccn1]
(+/−)-N⁵-((1R,5S,6r)-3-Oxabicyclo[3.1.0]hexan-6-yl)-N⁷-methyl-3-(pyridin-2-yl)-2,3-dihydrobenzofuran-5,7-dicarboxamide | 380.3 | 0.70 (high pH) |
| 74 | 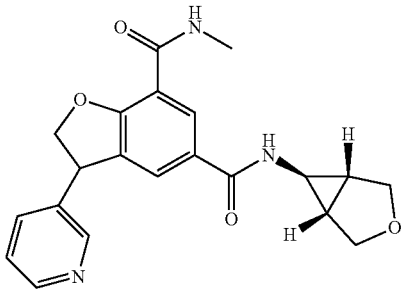 [SMILES: CNC(=O)c1cc(C(=O)N[C@H]2[C@@H]3COC[C@@H]32)cc2c1OCC2c1cccnc1]
(+/−)-N⁵-((1R,5S,6r)-3-Oxabicyclo[3.1.0]hexan-6-yl)-N⁷-methyl-3-(pyridin-3-yl)-2,3-dihydrobenzofuran-5,7-dicarboxamide | 380.3 | 0.43 (formic) |

| Example number | Name and Structure | [MH+] | Rt (min) |
|---|---|---|---|
| 75 | 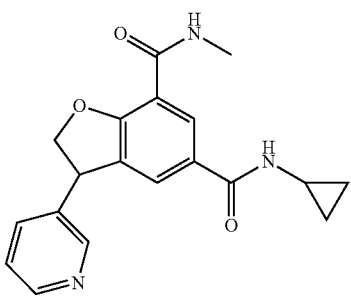 [SMILES: CNC(=O)c1cc(C(=O)NC2CC2)cc2c1OCC2c1cccnc1]<br>(+/−)-N⁵-Cyclopropyl-N⁷-methyl-3-(pyridin-3-yl)-2,3-dihydrobenzofuran-5,7-dicarboxamide | 338.3 | 0.68 (high pH) |
| 76 | 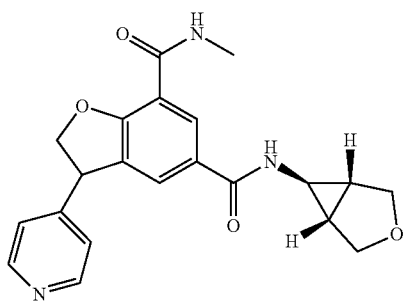 [SMILES: CNC(=O)c1cc(C(=O)N[C@H]2[C@@H]3COC[C@@H]32)cc2c1OCC2c1ccncc1]<br>(+/−)-N⁵-((1R,5S,6r)-3-Oxabicyclo[3.1.0]hexan-6-yl)-N⁷-methyl-3-(pyridin-4-yl)-2,3-dihydrobenzofuran-5,7-dicarboxamide | 380.4 | 0.65 (high pH) |
| 77 | 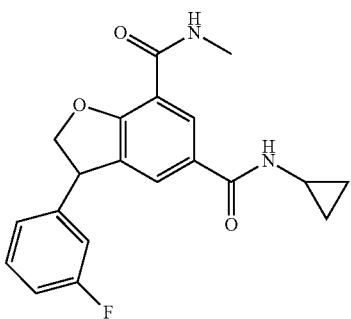 [SMILES: CNC(=O)c1cc(C(=O)NC2CC2)cc2c1OCC2c1cccc(F)c1]<br>(+/−)-N⁵-cyclopropyl-3-(3-fluorophenyl)-N⁷-methyl-2,3-dihydrobenzofuran-5,7-dicarboxamide | 355.3 | 0.92 (high pH) |

-continued

| Example number | Name and Structure | [MH+] | Rt (min) |
|---|---|---|---|
| 78 | 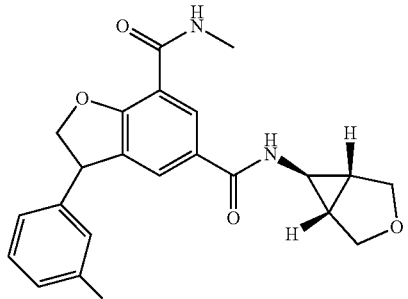<br>(+/−)-N⁵-((1S,5S,6r)-3-Oxabicyclo[3.1.0]hexan-6-yl)-3-(3-fluorophenyl)-N⁷-methyl-2,3-dihydrobenzofuran-5,7-dicarboxamide | 397.3 | 0.88 (formic) |
| 79 | 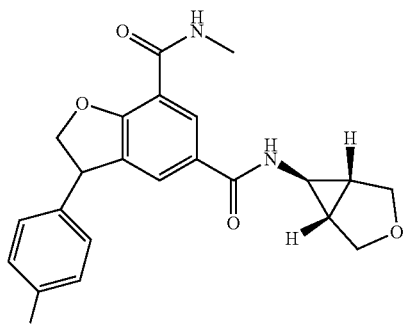<br>(+/−)-N⁵-((1R,5S,6r)-3-Oxabicyclo[3.1.0]hexan-6-yl)-3-(4-fluorophenyl)-N⁷-methyl-2,3-dihydrobenzofuran-5,7-dicarboxamide | 397.3 | 0.88 (formic) |

Example 80 rac-N⁵-((1R,5S)-3-oxabicyclo[3.1.0]hexan-6-yl)-N⁷-methyl-3-(1-methyl-1H-indol-4-yl)-2,3-dihydrobenzofuran-5,7-dicarboxamide

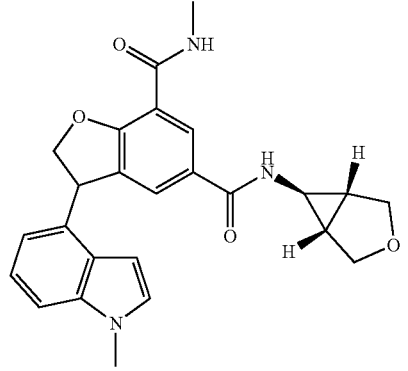 [SMILES: CNC(=O)c1cc(C(=O)N[C@H]2[C@@H]3COC[C@@H]32)cc2c1OCC2c1cccc2c1ccn2C]

Rac-N⁵-((1R,5S,6r)-3-oxabicyclo[3.1.0]hexan-6-yl)-N⁷-methyl-3-(1-methyl-1H-indol-4-yl)benzofuran-5,7-dicarboxamide (For a preparation see Intermediate 25, 53 mg, 0.123 mmol) and 5% w/w palladium on carbon (40 mg, 0.38 mmol) were stirred in ethanol (10 mL) under an atmosphere of hydrogen at rt for 16 h. A further portion of 5% w/w palladium on carbon (40 mg, 0.38 mmol) was added and the mixture stirred under a atmosphere of hydrogen at rt for 24 h. The reaction was filtered through celite to remove the catalyst and concentrated and dried to give the crude product. The crude product was further purified using MDAP (Formic method) to give the title compound (9 mg, 0.021 mmol, 16.90% yield) as a yellow solid.

LCMS (Formic): Rt: 0.93 min, [MH]⁺=432.4

The following examples (81-83) were prepared in a similar method to example 80:

| Example number | Name and structure | Rt [MH+] (min) |
|---|---|---|
| 81 | 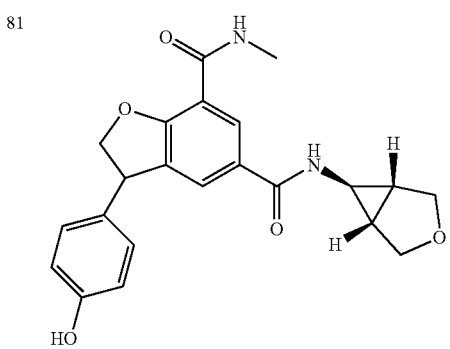<br>N⁵-((1R,5S,6r)-3-oxabicyclo[3.1.0]hexan-6-yl)-3-(4-hydroxyphenyl)-N⁷-methyl-2,3-dihydrobenzofuran-5,7-dicarboxamide | 395.3 0.72 (Formic) |
| 82 | 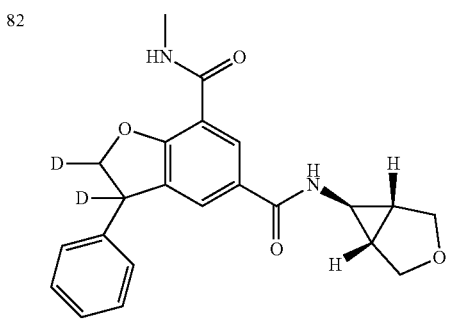<br>(+/−)-N⁵-((1R,5S,6r)-3-oxabicyclo[3.1.0]hexan-6-yl)-N⁷-methyl-3-phenyl-2,3-dihydrobenzofuran-5,7-dicarboxamide | 381.4 0.85 (Formic) |
| 83 | 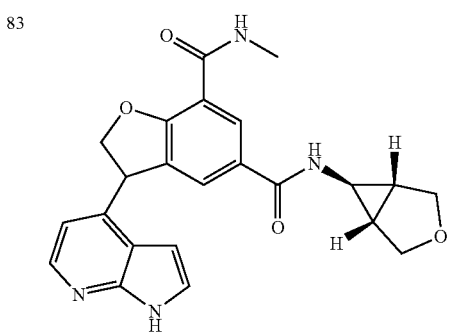<br>(+/−)-N⁵-((1R,5S,6r)-3-Oxabicyclo[3.1.0]hexan-6-yl)-N⁷-methyl-3-(1H-pyrrolo[2,3-b]pyridin-4-yl)-2,3-dihydrobenzofuran-5,7-dicarboxamide | 419.3 0.56 (formic) |

Example 84

N⁵-cyclopropyl-3-(1-(2-hydroxyethyl)-1H-indol-4-yl)-N⁷-methyl-2,3-dihydrobenzofuran-5,7-dicarboxamide

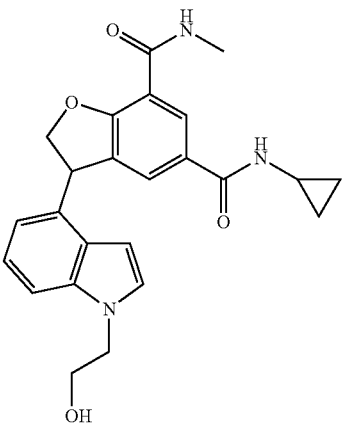 [SMILES: CNC(=O)c1cc(C(=O)NC2CC2)cc2c1OCC2c1cccc2c1ccn2CCO]

N⁵-cyclopropyl-3-(1H-indol-4-yl)-N⁷-methyl-2,3-dihydrobenzofuran-5,7-dicarboxamide (for a preparation, see Example 1, 21 mg, 0.056 mmol), 1,3-dioxolan-2-one (14.8 mg, 0.168 mmol) and K₂CO₃ (15.5 mg, 0.112 mmol) were added to a flask with N,N-dimethylformamide (3 mL). The reaction mixture was stirred at 90° C. for 2 h. Further portions of 1,3-dioxolan-2-one (14.78 mg, 0.168 mmol) and K₂CO₃ (15.5 mg, 0.112 mmol) were added and the reaction mixture was stirred at 90° C. for 16 h. Further portions of 1,3-dioxolan-2-one (14.78 mg, 0.168 mmol) and K₂CO₃ (15.5 mg, 0.112 mmol) were added and the reaction mixture was stirred at 90° C. for a further 4 h. The reaction mixture was diluted with water and extracted with DCM. The organics were washed with a 10% LiCl solution, dried via a hydrophobic frit and concentrated in vacuo. The residue was taken up in 1:1 MeOH:DMSO (1 mL), purified by MDAP (high pH extended method) and concentrated in vacuo to give the product N⁵-cyclopropyl-3-(1-(2-hydroxyethyl)-1H-indol-4-yl)-N⁷-methyl-2,3-dihydrobenzofuran-5,7-dicarboxamide (5.6 mg, 0.013 mmol, 23.9% yield), as a white solid. LC/MS (2 min High pH): Rt=0.82 min, [MH]⁺=420.4.

Example 85

N⁵-((1R,5S,6s)-3-azabicyclo[3.1.0]hexan-6-yl)-N⁷-methyl-3-phenyl-2,3-dihydrobenzofuran-5,7-dicarboxamide

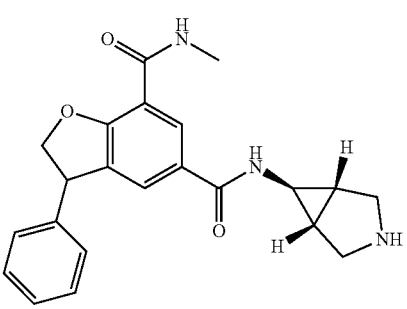 [SMILES: CNC(=O)c1cc(C(=O)N[C@H]2[C@@H]3CNC[C@@H]32)cc2c1OCC2c1ccccc1]

TFA (0.166 mL, 2.158 mmol) was added to a solution of (1R,5S,6s)-tert-butyl 6-(7-(methylcarbamoyl)-3-phenyl-2,3-dihydrobenzofuran-5-carboxamido)-3-azabicyclo[3.1.0]hexane-3-carboxylate (For a preparation, see Intermediate 30, 229 mg, 0.432 mmol) in DCM (4 mL). The reaction mixture was stirred for 1 h. The reaction mixture was then concentrated in vacuo. The sample was then dissolved in 5 mL of DCM and was loaded onto a 25 g Biotage SNAP column using a gradient of DCM:Methanolic ammonia (0-16%). The product containing fractions were combined and the solvent removed in vacuo. The sample was then dried under a stream of nitrogen for 2 hours to give $N^5$-((1R,5S,6s)-3-azabicyclo[3.1.0]hexan-6-yl)-$N^7$-methyl-3-phenyl-2,3-dihydrobenzofuran-5,7-dicarboxamide (107 mg, 0.255 mmol, 59.1% yield) as a white solid.

LC/MS (2 min Formic): Rt=0.54 min, $[MH]^+$=378.4.

Example 86

(S)-$N^5$-(3-((2s,5R)-5-amino-1,3-dioxan-2-yl)propyl)-$N^7$-methyl-3-phenyl-2,3-dihydrobenzofuran-5,7-dicarboxamide

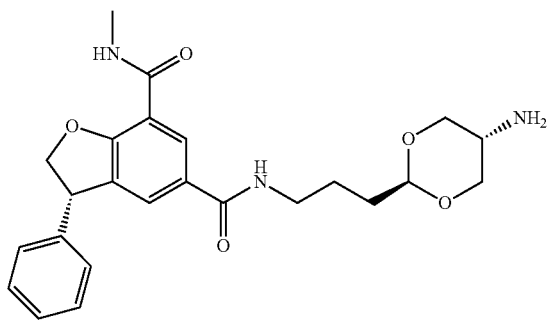 [SMILES: CNC(=O)c1cc(C(=O)NCCC[C@H]2OC[C@H](N)CO2)cc2c1OC[C@H]2c1ccccc1]

A suspension of p-toluenesulfonic acid monohydrate (38.6 mg, 0.203 mmol), (S)-$N^5$-(4,4-diethoxybutyl)-$N^7$-methyl-3-phenyl-2,3-dihydrobenzofuran-5,7-dicarboxamide (For a preparation see Intermediate 27, 116 mg, 0.184 mmol) and 2-(1,3-dihydroxypropan-2-yl)isoindoline-1,3-dione (44.9 mg, 0.203 mmol) in toluene (2 mL) was stirred at 70° C. under nitrogen overnight. The reaction mixture was allowed to cool to room temperature and was diluted with EtOAc and then washed with saturated aqueous $Na_2CO_3$ and the layers separated. The aqueous phase was extracted with further ethyl acetate and the organic layers combined and filtered through a hydrophobic frit. The filtrate was evaporated in vacuo to afford a brown solid. The solid was dissolved in Ethanol (2.0 mL) and hydrazine hydrate (0.090 mL, 1.843 mmol) was added and the reaction mixture left to stir at 50° C. overnight. The reaction was left to cool to room temperature, concentrated in vacuo and purified by MDAP (HPH) to give (S)-$N^5$-(3-((2s,5R)-5-amino-1,3-dioxan-2-yl)propyl)-$N^7$-methyl-3-phenyl-2,3-dihydrobenzofuran-5,7-dicarboxamide (15 mg, 0.034 mmol, 19% yield) as a yellow solid.

LCMS (method Formic): Retention time 0.81, $[M+H]^+$=440.4

Example 87

(+/−)-3-(4-(2-aminoethoxy)phenyl)-$N^5$-((1R,5S,6r)-3-oxabicyclo[3.1.0]hexan-6-yl)-$N^7$-methyl-2,3-dihydrobenzofuran-5,7-dicarboxamide

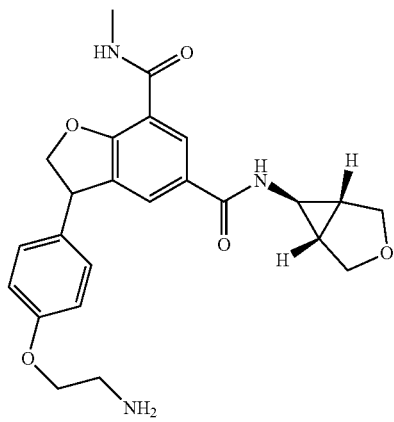 [SMILES: CNC(=O)c1cc(C(=O)N[C@H]2[C@@H]3COC[C@@H]32)cc2c1OCC2c1ccc(OCCN)cc1]

tert-Butyl (2-(4-(5-(((1R,5S,6r)-3-oxabicyclo[3.1.0]hexan-6-yl)carbamoyl)-7-(methylcarbamoyl)-2,3-dihydrobenzofuran-3-yl)phenoxy)ethyl)carbamate (for a preparation see Intermediate 31, 100 mg, 0.186 mmol) was taken up in DCM (5 mL), treated with TFA (200 µL, 2.60 mmol) and stirred at rt for 1 h. The reaction was concentrated in vacuo and eluted through an $NH_2$ SPE (1 g) with MeOH, the eluent was concentrated and dried to give 3-(4-(2-aminoethoxy)phenyl)-$N^5$-((1R,5S,6r)-3-oxabicyclo[3.1.0]hexan-6-yl)-$N^7$-methyl-2,3-dihydrobenzofuran-5,7-dicarboxamide (89 mg, 0.203 mmol, 109% yield) as a colourless gum.

LCMS (method Formic): Retention time 0.49, $[M+H]^+$=438.4

Example 88

(+/−)-$N^5$-((1R,5S,6s)-3-acetyl-3-azabicyclo[3.1.0]hexan-6-yl)-$N^7$-methyl-3-phenyl-2,3-dihydrobenzofuran-5,7-dicarboxamide

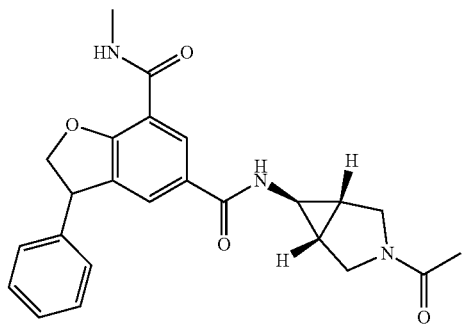 [SMILES: CNC(=O)c1cc(C(=O)N[C@H]2[C@@H]3CN(C(C)=O)C[C@@H]32)cc2c1OCC2c1ccccc1]

Acetyl chloride (0.037 mL, 0.525 mmol) was added to a solution of $N^5$-((1R,5S,6s)-3-azabicyclo[3.1.0]hexan-6-yl)-$N^7$-methyl-3-phenyl-2,3-dihydrobenzofuran-5,7-dicarboxamide (for a preparation see Example 85, 66 mg, 0.175 mmol) and DIPEA (0.031 mL, 0.175 mmol). The reaction mixture was stirred for 30 mins at 50° C. The reaction mixture was allowed to cool and partitioned between EtOAc and water. The organic layer washed with water and sat. aq. NaHCO$_3$, passed through a hydrophobic frit and evaporated in vacuo to afford the crude product. The crude product was purified by silica chromatography eluting with 20-80% cyclohexane:EtOAc to afford N$^5$-((1R,5S,6s)-3-acetyl-3-azabicyclo[3.1.0]hexan-6-yl)-N$^7$-methyl-3-phenyl-2,3-dihydrobenzofuran-5,7-dicarboxamide (5.6 mg, 0.013 mmol, 7% yield) as a white solid.

LCMS (method Formic): Retention time 0.80, [M+H]$^+$=420.4

Example 89

(+/−)N$^5$-((1R,5S,6r)-3-oxabicyclo[3.1.0]hexan-6-yl)-3-(1H-indol-3-yl)-N$^7$-methyl-2,3-dihydrobenzofuran-5,7-dicarboxamide

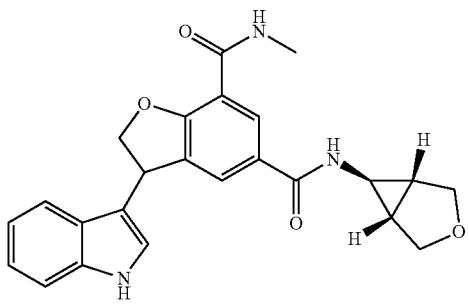 [SMILES: CNC(=O)c1cc(C(=O)N[C@H]2[C@@H]3COC[C@@H]32)cc2c1OCC2c1c[nH]c2ccccc12]

(+/−)Tert-butyl 3-(5-(((1R,5S,6r)-3-oxabicyclo[3.1.0]hexan-6-ylcarbamoyl)-7-(methylcarbamoyl)-2,3-dihydrobenzofuran-3-yl)-1H-indole-1-carboxylate (For a preparation see Intermediate 32, 155 mg, 0.299 mmol), was dissolved in DCM (6 mL) and TFA (0.5 mL, 6.49 mmol) was added. The reaction mixture was stirred at rt for 16 h. The reaction was quenched with sat. NaHCO$_3$ (aq,15 mL) and stirred for 30 min. The reaction mixture was diluted with water (10 mL) and extracted with DCM (3×30 mL). The organics were passed through a hydrophobic frit and concentrated in vacuo.

The residue was taken up in 1:1 MeOH:DMSO (3 mL) and purified by MDAP (high pH). The relevant fractions were combined and concentrated in vacuo.

The residue was taken up in 1:1 MeOH:DMSO (1 mL) and purified by MDAP (formic). The relevant fractions were combined and concentrated in vacuo to give the product (+/−)N5-((1R,5S,6r)-3-oxabicyclo[3.1.0]hexan-6-yl)-3-(1H-indol-3-yl)-N7-methyl-2,3-dihydrobenzofuran-5,7-dicarboxamide (4 mg, 9.58 μmol, 3.20% yield) as a white solid.

LCMS (method formic): Retention time 0.86 min, [M+H]$^+$=418

Example 90

(+/−)-N$^5$-((1R,5S,6r)-3-Oxabicyclo[3.1.0]hexan-6-yl)-3-(3-(2-hydroxyethoxy)phenyl)-N$^7$-methyl-2,3-dihydrobenzofuran-5,7-dicarboxamide

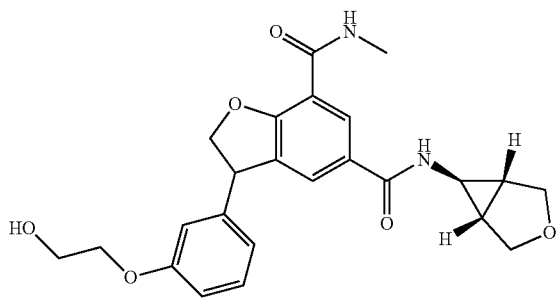 [SMILES: CNC(=O)c1cc(C(=O)N[C@H]2[C@@H]3COC[C@@H]32)cc2c1OCC2c1cccc(OCCO)c1]

(+/−)-N$^5$-((1R,5S,6r)-3-Oxabicyclo[3.1.0]hexan-6-yl)-3-(3-hydroxyphenyl)-N$^7$-methyl-2,3-dihydrofuro[3,2-b]pyridine-5,7-dicarboxamide (For a preparation see Intermediate 33, 116 mg, 0.29 mmol) was dissolved in DMF (6 mL) with 1,3-dioxolan-2-one (78 mg, 0.88 mmol) and K$_2$CO$_3$ (81 mg, 0.59 mmol). The reaction mixture was stirred at 80° C. under nitrogen for 16 h. Further 1,3-dioxolan-2-one (78 mg, 0.880 mmol) and K$_2$CO$_3$ (81 mg, 0.59 mmol) were added and the reaction mixture was stirred at 90° C. under nitrogen for 16 h. The reaction mixture was left to cool. The mixture was then diluted with water (20 mL), extracted with EtOAc (3×50 mL). The organics were washed with brine (~5 mL) and a 10% w/w aqueous LiCl solution, dried via a hydrophobic frit and concentrated in vacuo. The residue was taken up in DCM (6 mL), charged to a 10 g SNAP column and eluted with 0-100% (25% EtOH in EtOAc):cyclohexane. The relevant fractions were combined and concentrated in vacuo. The residue was taken up in 1:1 MeOH:DMSO (1 mL) and purified by MDAP (high pH). The relevant fractions were combined and concentrated in vacuo to give (+/−)-N$^5$-((1R,5S,6r)-3-oxabicyclo[3.1.0]hexan-6-yl)-3-(3-(2-hydroxyethoxy)phenyl)-N$^7$-methyl-2,3-dihydrobenzofuran-5,7-dicarboxamide (6.5 mg, 0.015 mmol, 5% yield).

LCMS (High pH): Rt=0.76 min, MH$^+$=439.4

Example 91

(S)-N$^7$-Methyl-3-phenyl-N$^5$-((1R,5S,6s)-3-propionyl-3-azabicyclo[3.1.0]hexan-6-yl)-2,3-dihydrobenzofuran-5,7-dicarboxamide

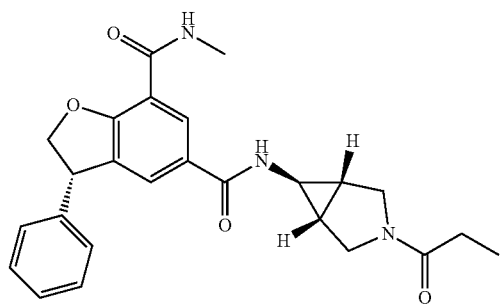 [SMILES: CCC(=O)N1C[C@@H]2[C@H](C1)[C@H]2NC(=O)c1cc(C(=O)NC)c2c(c1)[C@H](c1ccccc1)CO2]

(S)-N⁵-((1R,5S,6s)-3-Azabicyclo[3.1.0]hexan-6-yl)-N⁷-methyl-3-phenyl-2,3-dihydrobenzofuran-5,7-dicarboxamide (For a preparation see Intermediate 34, 80 mg, 0.21 mmol) and propionic anhydride (500 μL, 0.21 mmol) were stirred at rt for 1 h. The reaction was diluted with water and extracted with EtOAc, the organic layer was washed with brine and dried using a hydrophobic frit and concentrated to give a colourless oil. This oil was purified using a flash silica SP4 chromatography, using a SNAP 10 g silica column and eluting with a gradient of 0-50% (25% EtOH in EtOAc):EtOAc to give (S)-N⁷-methyl-3-phenyl-N⁵-((1R,5S,6s)-3-propionyl-3-azabicyclo[3.1.0]hexan-6-yl)-2,3-dihydrobenzofuran-5,7-dicarboxamide (75 mg, 0.17 mmol, 82% yield) as a white solid.

LCMS (Formic): Rt=0.87 min, MH⁺=434.4

Example 92

(+/−)-N⁵-((1R,5S,6r)-3-Oxabicyclo[3.1.0]hexan-6-yl)-3-(1-(2-hydroxyethyl)-1H-indol-4-yl)-N⁷-methyl-2,3-dihydrobenzofuran-5,7-dicarboxamide

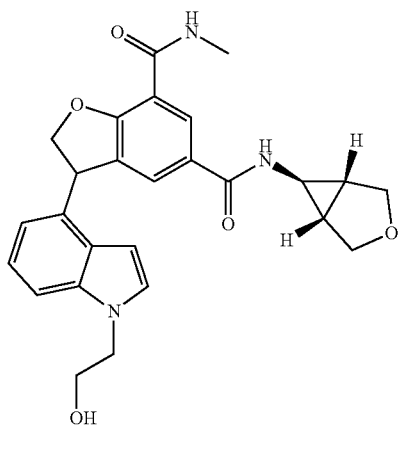 [SMILES: CNC(=O)c1cc(C(=O)N[C@H]2[C@@H]3COC[C@@H]32)cc2c1OCC2c1cccc2c1ccn2CCO]

(+/−)-N⁵-((1R,5S,6r)-3-Oxabicyclo[3.1.0]hexan-6-yl)-3-(1H-indol-4-yl)-N⁷-methyl-2,3-dihydrobenzofuran-5,7-dicarboxamide (For a preparation see example 2, 19 mg, 0.046 mmol), 1,3-dioxolan-2-one (12.0 mg, 0.137 mmol) and K₂CO₃ (12.58 mg, 0.091 mmol) were added to a flask with DMF (3 mL). The reaction mixture was stirred at 90° C. under nitrogen for 3 h. Further 1,3-dioxolan-2-one (12.0 mg, 0.137 mmol) and K₂CO₃ (12.6 mg, 0.091 mmol) were added and the reaction mixture was stirred at 90° C. for 16 h. Further 1,3-dioxolan-2-one (30 mg, 0.34 mmol) and K₂CO₃ (30 mg, 0.217 mmol) were added and the reaction mixture was stirred at 90° C. for 3 h. Further K₂CO₃ (12.6 mg, 0.091 mmol) and 1,3-dioxolan-2-one (12.0 mg, 0.137 mmol) were added and the reaction mixture was stirred at 90° C. for 1 h. The reaction mixture was then placed in a microwave vial and irradiated in a Biotage microwave at 90° C. for 30 min. Further 1,3-dioxolan-2-one (12.0 mg, 0.137 mmol) and K₂CO₃ (12.6 mg, 0.091 mmol) were added and the reaction mixture was irradiated in a Biotage microwave at 100° C. for 30 min. Further 1,3-dioxolan-2-one (30 mg, 0.341 mmol) was added and the reaction mixture was irradiated at 110° C. for 30 min. Further 1,3-dioxolan-2-one (30 mg, 0.341 mmol) was added and the reaction mixture was stirred at 120° C. for 30 min. Further 1,3-dioxolan-2-one (70 mg, 0.795 mmol) and K₂CO₃ (50 mg, 0.362 mmol) were added and the reaction mixture was irradiated in a biotage microwave at 130° C. for 1 h. The reaction mixture was diluted with water and extracted with DCM. The organics were washed with 10% LiCl solution, dried via a hydrophobic frit and concentrated in vacuo. The residue was taken up in 1:1 MeOH:DMSO (1 ml), purified by MDAP (high pH) and concentrated in vacuo to give the product (+/−)-N⁵-((1R,5S,6r)-3-oxabicyclo[3.1.0]hexan-6-yl)-3-(1-(2-hydroxyethyl)-1H-indol-4-yl)-N⁷-methyl-2,3-dihydrobenzofuran-5,7-dicarboxamide (4 mg, 8.7 μmol, 19% yield) as a white solid.

LCMS (Formic): Rt=0.79 min, MH⁺=462.4

Example 93

(S)-N⁵-(2-((2r,5S)-5-amino-1,3-dioxan-2-yl)ethyl)-N⁷-methyl-3-phenyl-2,3-dihydrobenzofuran-5,7-dicarboxamide

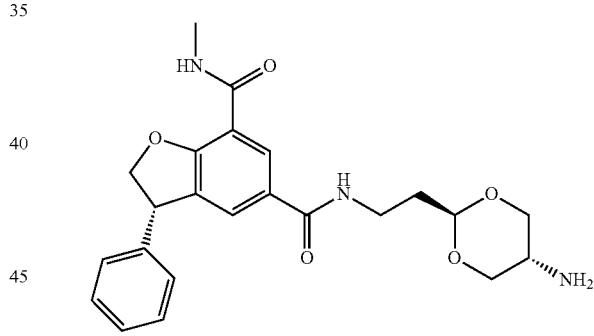

To a suspension of (S)-N⁵-(2-((2r,5S)-5-(1,3-dioxoisoindolin-2-yl)-1,3-dioxan-2-yl)ethyl)-N⁷-methyl-3-phenyl-2,3-dihydrobenzofuran-5,7-dicarboxamide (For a preparation see Intermediate 28, 641.5 mg, 0.855 mmol) in EtOH (20 mL) was added hydrazine hydrate (0.415 mL, 8.55 mmol) and the solution was stirred at 50° C. overnight. The reaction was cooled to rt and concentrated under a stream of N₂ to give a sticky yellow solid. This was directly purified by silica gel column chromatography eluting with a gradient of 0-40% (20% (2M NH3 in MeOH) in DCM): DCM to give (S)-N⁵-(2-((2r,5S)-5-amino-1,3-dioxan-2-yl)ethyl)-N⁷-methyl-3-phenyl-2,3-dihydrobenzofuran-5, 7-dicarboxamidedicarboxamide (351.2 mg, 0.825 mmol, 97% yield) as a colourless gum.

LCMS (method formic): Retention time 0.60 min, [M+H]⁺=426

Example 94

(+/−)$N^7$-methyl-$N^5$-(2-((R)-morpholin-2-yl)ethyl)-3-phenyl-2,3-dihydrobenzofuran-5,7-dicarboxamide

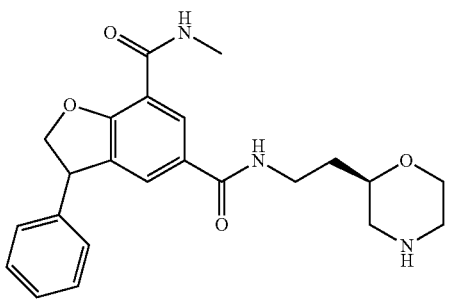 [SMILES: CNC(=O)c1cc(C(=O)NCC[C@@H]2CNCCO2)cc2c1OCC2c1ccccc1]

TFA (0.5 ml, 6.49 mmol) was added to (+/−)(2R)-tert-butyl 2-(2-(7-(methylcarbamoyl)-3-phenyl-2,3-dihydrobenzofuran-5-carboxamido)ethyl)morpholine-4-carboxylate (For a preparation see Intermediate 29, 50 mg, 0.098 mmol) in DCM (3 mL) at rt under $N_2$. The resulting solution was stirred at rt for 2 h. The reaction was loaded onto a 2 g SCX column and flushed with MeOH (20 mL). The column was then flushed with ammonia (2M in MeOH) (20 mL). Pure fractions were concentrated in vacuo to afford (+/−)$N^7$-methyl-$N^5$-(2-((R)-morpholin-2-yl)ethyl)-3-phenyl-2,3-dihydrobenzofuran-5,7-dicarboxamide (18 mg, 0.044 mmol, 44.8% yield) as a cream solid.

LCMS (method formic): Retention time 0.58 min, $[M+H]^+$=410

The following examples were also prepared according to the outlined methods

| Example number | Name and Structure | [MH⁺] | Rt (min) |
|---|---|---|---|
| 95 | $N^5$-isopropyl-$N^7$-methyl-3-phenyl-2,3-dihydrobenzofuran-5,7-dicarboxamide | 339.1 | 0.95 (Formic) |
| 96 | $N^5$-(2-(dimethylamino)ethyl)-$N^7$-methyl-3-phenyl-2,3-dihydrobenzofuran-5,7-dicarboxamide | 368.1 | 0.55 (Formic) |
| 97 | (S*)-$N^5$-((1R,5S,6s)-3-azabicyclo[3.1.0]hexan-6-yl)-$N^7$- | 378.4 | 0.55 (Formic) |

| Example number | Name and Structure | [MH+] | Rt (min) |
|---|---|---|---|
| | methyl-3-phenyl-2,3-dihydrobenzofuran-5,7-dicarboxamide | | |
| 98 | 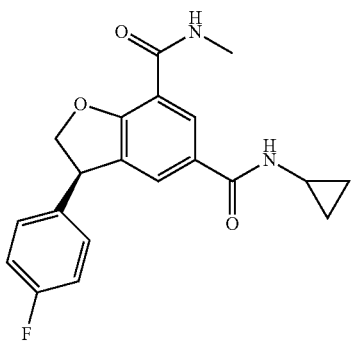 [SMILES: CNC(=O)c1cc(C(=O)NC2CC2)cc2c1OC[C@@H]2c1ccc(F)cc1]<br>(R*)-N⁵-cyclopropyl-3-(4-fluorophenyl)-N⁷-methyl-2,3-dihydrobenzofuran-5,7-dicarboxamide | 355.3 | 0.92 (High pH) |
| 99 | 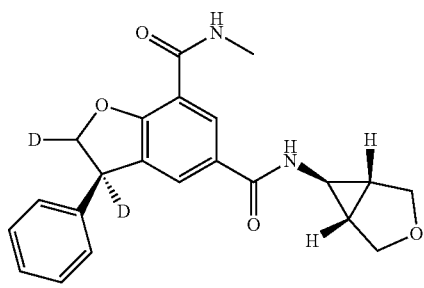 [SMILES: [2H]C1Oc2c(C(=O)NC)cc(C(=O)N[C@H]3[C@@H]4COC[C@@H]43)cc2[C@@]1([2H])c1ccccc1]<br>(R)-N⁵-((1R,5S,6r)-3-oxabicyclo[3.1.0]hexan-6-yl)-N⁷-methyl-3-phenyl-2,3-dihydrobenzofuran-5,7-dicarboxamide, deuterated at positions shown | 380.4 | 0.84 (Formic) |
| 100 | 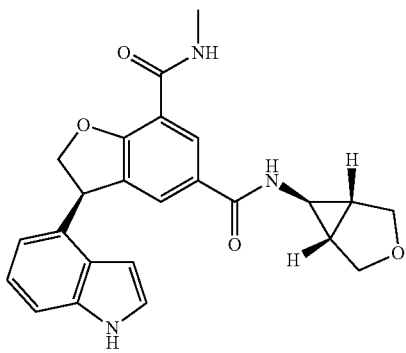 [SMILES: CNC(=O)c1cc(C(=O)N[C@H]2[C@@H]3COC[C@@H]32)cc2c1OC[C@@H]2c1cccc2[nH]ccc12]<br>(R)-N⁵-((1R,5S,6r)-3-oxabicyclo[3.1.0]hexan-6-yl)-3-(1H-indol-4-yl)-N⁷-methyl-2,3-dihydrobenzofuran-5,7-dicarboxamide | 418.4 | 0.84 (Formic) |

-continued
| Example number | Name and Structure | [MH+] | Rt (min) |
|---|---|---|---|
| 101 | 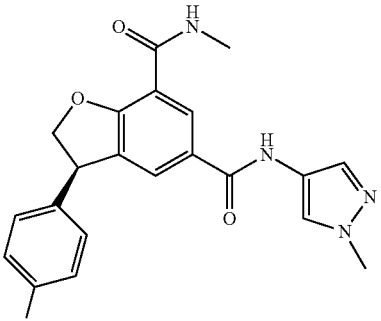<br>(R*)-3-(4-fluorophenyl)-N⁷-methyl-N⁵-(1-methyl-1H-pyrazol-4-yl)-2,3-dihydrobenzofuran-5,7-dicarboxamide | 395.4 | 0.90 (High pH) |
| 102 | 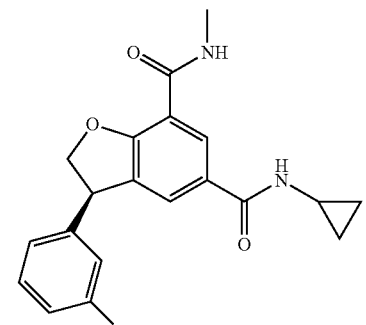<br>(R*)-N⁵-cyclopropyl-3-(3-fluorophenyl)-N⁷-methyl-2,3-dihydrobenzofuran-5,7-dicarboxamide | 355.2 | 0.92 (Formic) |
| 103 | 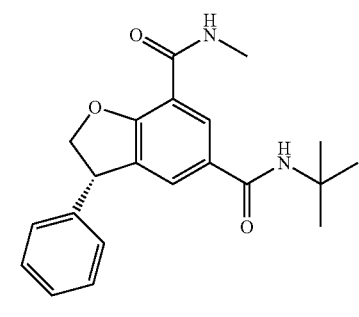 [SMILES: CNC(=O)c1cc(C(=O)NC(C)(C)C)cc2c1OC[C@H]2c1ccccc1]<br>(S)-N⁵-(tert-butyl)-N⁷-methyl-3-phenyl-2,3-dihydrobenzofuran-5,7-dicarboxamide | 353.3 | 1.06 (Formic) |
| 104 | 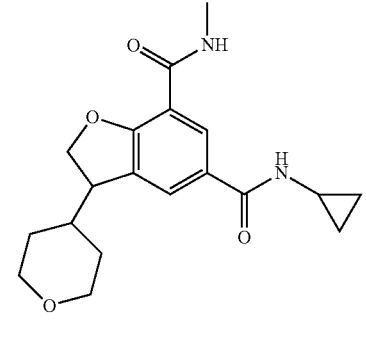 [SMILES: CNC(=O)c1cc(C(=O)NC2CC2)cc2c1OCC2C1CCOCC1]<br> | 345.3 | 0.70 (Formic) |

| Example number | Name and Structure | [MH⁺] | Rt (min) |
|---|---|---|---|
| | $N^5$-cyclopropyl-$N^7$-methyl-3-(tetrahydro-2H-pyran-4-yl)-2,3-dihydrobenzofuran-5,7-dicarboxamide | | |
| 105 | 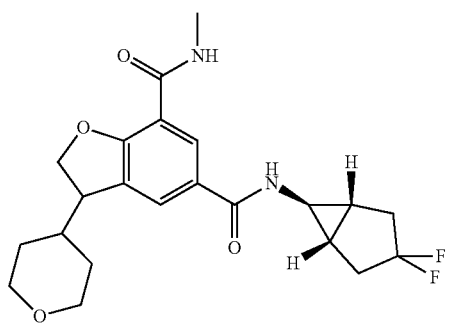 [SMILES: CNC(=O)c1cc(C(=O)N[C@H]2[C@@H]3CC(F)(F)C[C@@H]32)cc2c1OCC2C1CCOCC1]<br>$N^5$-((1R,5S,6r)-3,3-difluorobicyclo[3.1.0]hexan-6-yl)-$N^7$-methyl-3-(tetrahydro-2H-pyran-4-yl)-2,3-dihydrobenzofuran-5,7-dicarboxamide | 421.3 | 0.87 (Formic) |
| 106 | 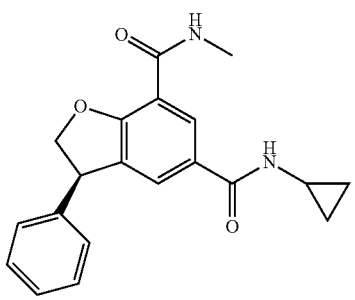 [SMILES: CNC(=O)c1cc(C(=O)NC2CC2)cc2c1OC[C@@H]2c1ccccc1]<br>(R)-$N^5$-cyclopropyl-$N^7$-methyl-3-phenyl-2,3-dihydrobenzofuran-5,7-dicarboxamide | 337.2 | 0.91 (Formic) |
| 107 | 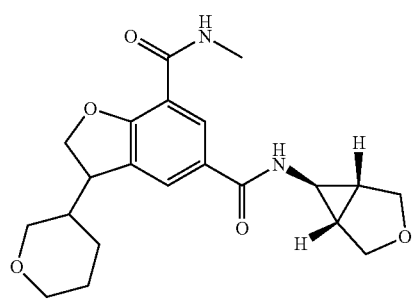 [SMILES: CNC(=O)c1cc(C(=O)N[C@H]2[C@@H]3COC[C@@H]32)cc2c1OCC2C1CCCOC1]<br>$N^5$-((1R,5S,6r)-3-oxabicyclo[3.1.0]hexan-6-yl)-$N^7$-methyl-3-(tetrahydro-2H-pyran-3-yl)-2,3-dihydrobenzofuran-5,7-dicarboxamide | 387.4 | 0.73 (High pH) |

| Example number | Name and Structure | [MH+] | Rt (min) |
|---|---|---|---|
| 108 | 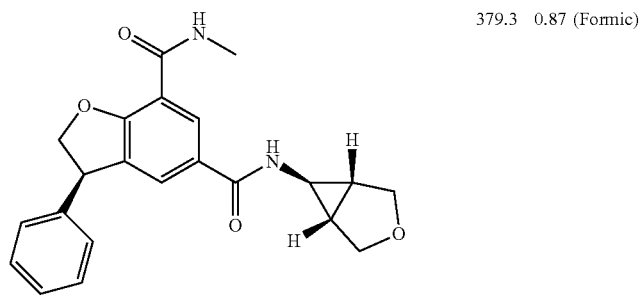<br>(R*)-$N^5$-((1R,5S,6r)-3-oxabicyclo[3.1.0]hexan-6-yl)-$N^7$-methyl-3-phenyl-2,3-dihydrobenzofuran-5,7-dicarboxamide | 379.3 | 0.87 (Formic) |
| 109 | 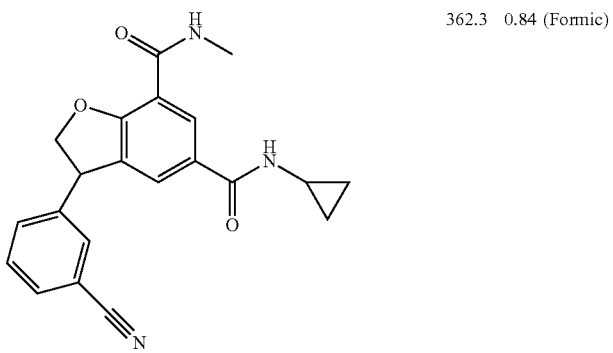<br>3-(3-cyanophenyl)-$N^5$-cyclopropyl-$N^7$-methyl-2,3-dihydrobenzofuran-5,7-dicarboxamide | 362.3 | 0.84 (Formic) |
| 110 | 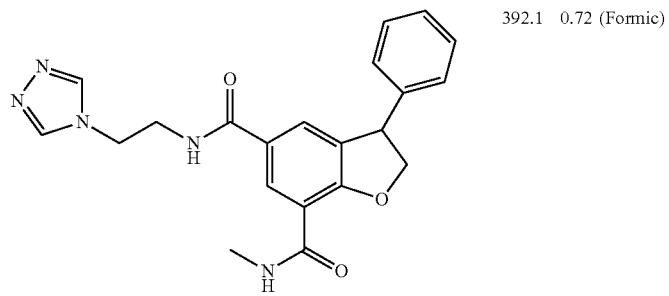<br>$N^5$-(2-(4H-1,2,4-triazol-4-yl)ethyl)-$N^7$-methyl-3-phenyl-2,3-dihydrobenzofuran-5,7-dicarboxamide | 392.1 | 0.72 (Formic) |

| Example number | Name and Structure | [MH+] | Rt (min) |
|---|---|---|---|
| 111 | 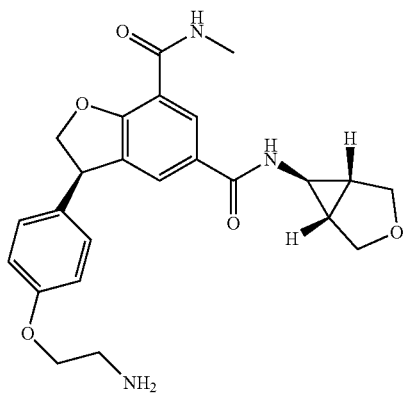 [SMILES: CNC(=O)c1cc(C(=O)N[C@H]2[C@@H]3COC[C@@H]32)cc2c1OC[C@@H]2c1ccc(OCCN)cc1]<br>(R*)-3-(4-(2-aminoethoxy)phenyl)-N$^5$-((1R,5S,6r)-3-oxabicyclo[3.1.0]hexan-6-yl)-N$^7$-methyl-2,3-dihydrobenzofuran-5,7-dicarboxamide | 438.4 | 0.49 (Formic) |
| 112 | 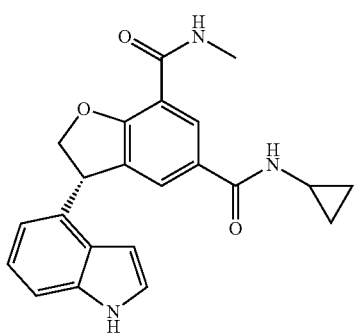 [SMILES: CNC(=O)c1cc(C(=O)NC2CC2)cc2c1OC[C@H]2c1cccc2[nH]ccc12]<br>(S*)-N$^5$-cydopropyl-3-(1H-indol-4-yl)-N$^7$-methyl-2,3-dihydrobenzofuran-5,7-dicarboxamide | 376.3 | 0.87 (Formic) |
| 113 | 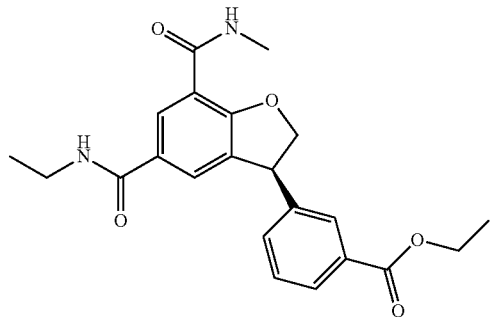 [SMILES: CCNC(=O)c1cc(C(=O)NC)c2c(c1)[C@H](c1cccc(C(=O)OCC)c1)CO2]<br>(R*)-ethyl 3-(5-(ethylcarbamoyl)-7-(methylcarbamoyl)-2,3-dihydrobenzofuran-3-yl)benzoate | 397.2 | 1.96 (Formic) |

| Example number | Name and Structure | [MH+] | Rt (min) |
|---|---|---|---|
| 114 | 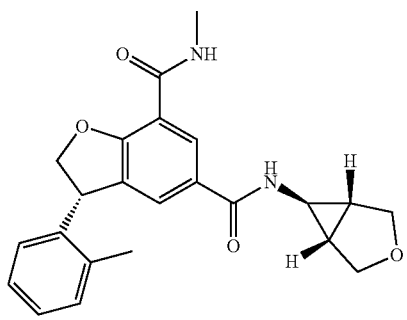 [SMILES: CNC(=O)c1cc(C(=O)N[C@H]2[C@@H]3COC[C@@H]32)cc2c1OC[C@H]2c1ccccc1C]
(S*)-N⁵-((1R,5S,6r)-3-oxabicyclo[3.1.0]hexan-6-yl)-N⁷-methyl-3-(o-tolyl)-2,3-dihydrobenzofuran-5,7-dicarboxamide | 393.4 | 0.93 (Formic) |
| 115 | 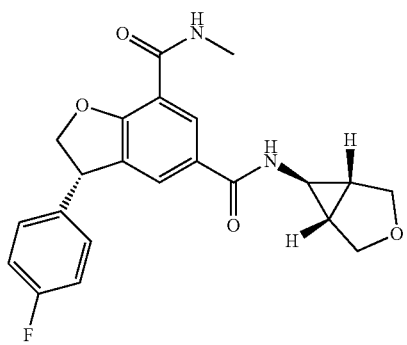 [SMILES: CNC(=O)c1cc(C(=O)N[C@H]2[C@@H]3COC[C@@H]32)cc2c1OC[C@H]2c1ccc(F)cc1]
(S*)-N⁵-((1R,5S,6r)-3-oxabicyclo[3.1.0]hexan-6-yl)-3-(4-fluorophenyl)-N⁷-methyl-2,3-dihydrobenzofuran-5,7-dicarboxamide | 397.4 | 0.88 (Formic) |
| 116 | 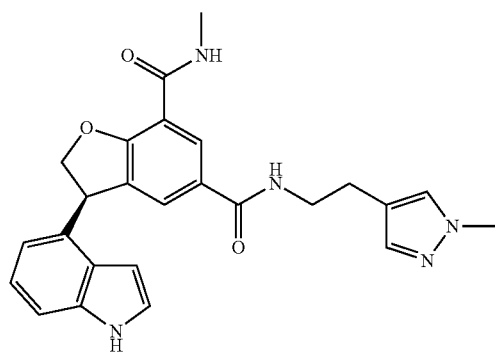 [SMILES: CNC(=O)c1cc(C(=O)NCCc2cnn(C)c2)cc2c1OC[C@@H]2c1cccc2[nH]ccc12]
(R*)-3-(1H-indol-4-yl)-N⁷-methyl-N⁵-(2-(1-methyl-1H-pyrazol-4-yl)ethyl)-2,3-dihydrobenzofuran-5,7-dicarboxamide | 444.4 | 0.83 (Formic) |

-continued

| Example number | Name and Structure | [MH+] | Rt (min) |
|---|---|---|---|
| 117 | 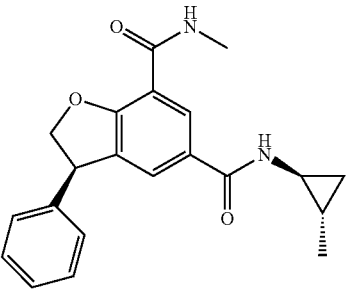 [SMILES: CNC(=O)c1cc(C(=O)N[C@H]2C[C@@H]2C)cc2c1OC[C@@H]2c1ccccc1]<br>(R*)-N⁷-methyl-N⁵-((1S,2S)-2-methylcyclopropyl)-3-phenyl-2,3-dihydrobenzofuran-5,7-dicarboxamide | 351.3 | 0.99 (Formic) |
| 118 | 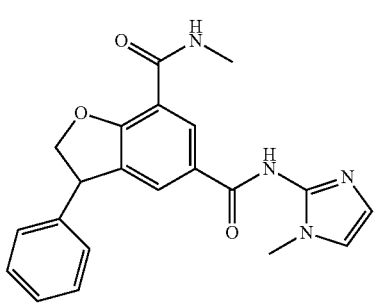 [SMILES: CNC(=O)c1cc(C(=O)Nc2nccn2C)cc2c1OCC2c1ccccc1]<br>N⁷-methyl-N⁵-(1-methyl-1H-imidazol-2-yl)-3-phenyl-2,3-dihydrobenzofuran-5,7-dicarboxamide | 377.1 | 0.61 (Formic) |
| 119 | 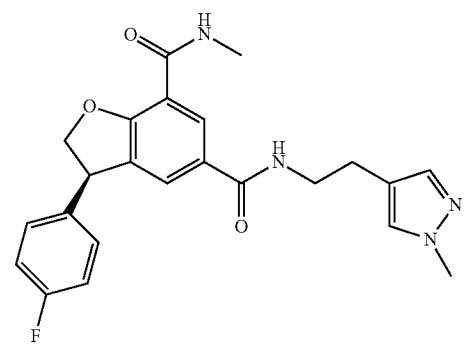 [SMILES: CNC(=O)c1cc(C(=O)NCCc2cnn(C)c2)cc2c1OC[C@@H]2c1ccc(F)cc1]<br>(R*)-3-(4-fluorophenyl)-N⁷-methyl-N⁵-(2-(1-methyl-1H-pyrazol-4-yl)ethyl)-2,3-dihydrobenzofuran-5,7-dicarboxamide | 423.4 | 0.89 (High pH) |
| 120 | 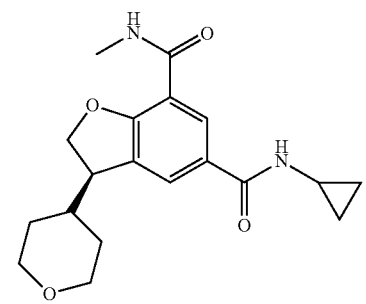 [SMILES: CNC(=O)c1cc(C(=O)NC2CC2)cc2c1OC[C@@H]2C1CCOCC1]<br>(R*)-N⁵-cyclopropyl-N⁷-methyl-3-(tetrahydro-2H-pyran-4-yl)-2,3-dihydrobenzofuran-5,7-dicarboxamide | 345.3 | 0.71 (Formic) |

| Example number | Name and Structure | [MH+] | Rt (min) |
|---|---|---|---|
| 121 | 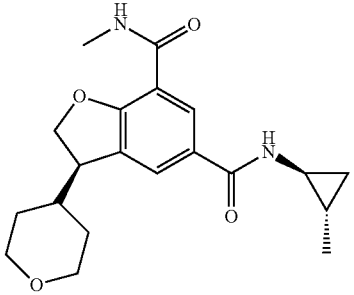 [SMILES: CNC(=O)c1cc(C(=O)N[C@H]2C[C@@H]2C)cc2c1OC[C@@H]2C1CCOCC1]<br>(R*)-N⁷-methyl-N⁵-((1S,2S)-2-methylcyclopropyl)-3-(tetrahydro-2H-pyran-4-yl)-2,3-dihydrobenzofuran-5,7-dicarboxamide | 359.3 | 0.79 (Formic) |
| 122 | 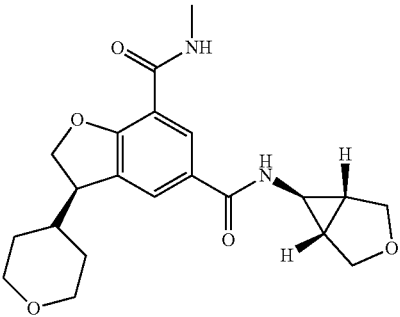 [SMILES: CNC(=O)c1cc(C(=O)N[C@H]2[C@@H]3COC[C@@H]32)cc2c1OC[C@@H]2C1CCOCC1]<br>(R*)-N⁵-((1R,5S,6r)-3-oxabicyclo[3.1.0]hexan-6-yl)-N⁷-methyl-3-(tetrahydro-2H-pyran-4-yl)-2,3-dihydrobenzofuran-5,7-dicarboxamide | 387.4 | 0.69 (Formic) |
| 123 | 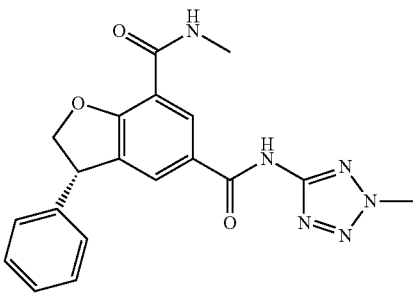 [SMILES: CNC(=O)c1cc(C(=O)Nc2nnn(C)n2)cc2c1OC[C@H]2c1ccccc1]<br>(S)-N⁷-methyl-N⁵-(2-methyl-2H-tetrazol-5-yl)-3-phenyl-2,3-dihydrobenzofuran-5,7-dicarboxamide | 379.3 | 0.71 (Formic) |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

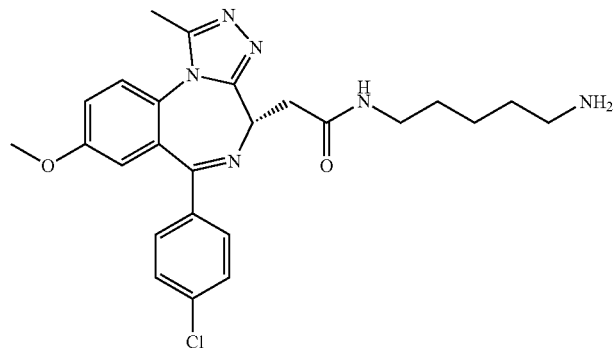

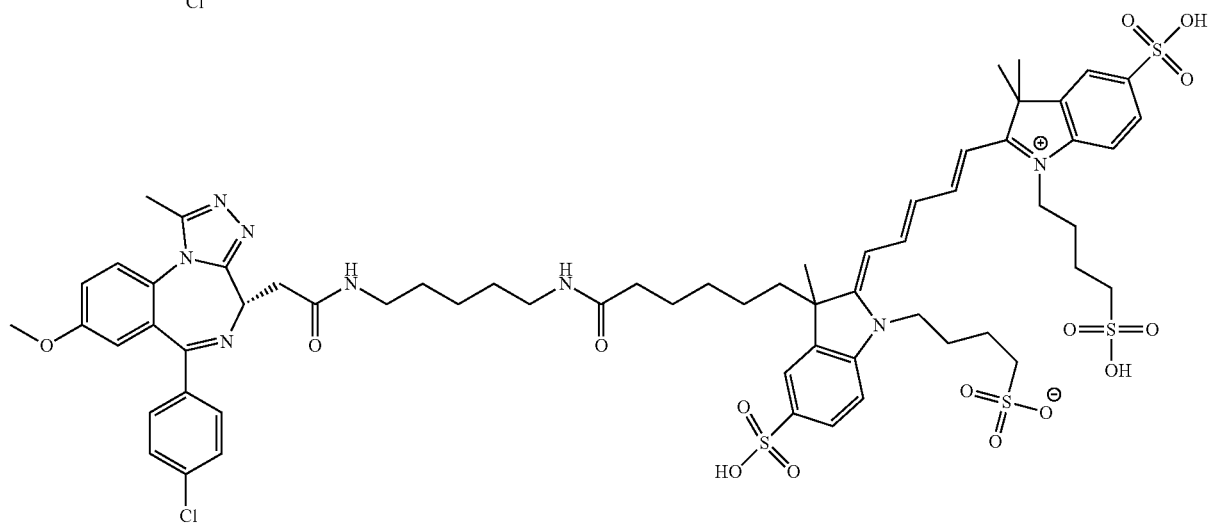

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μl) was added a solution of AlexaFluor647-ONSu (2.16 mg, 1.97 μmol) also in DMF (100 μl). The mixture was basified with DIPEA (1 μl, 5.73 μmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transfered with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/– corresponding with M-29. This equates to $[(M+2H)/2]^+$ for a calculated mass of 1320.984 which is M-29. This is a standard occurence with the Alexa Fluor 647 dye and represents a theoretical loss of two methylene groups under the conditions of the mass spectrometer.

Assay Principle: In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 mutant TR-FRET competition assays: All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 µsecs, measuring emission of the donor and acceptor fluorophores at λ615 nm and λ665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10\hat{\ }x/10\hat{\ }c)\hat{\ }d)$$

Where 'a' is the minimum, 'b' is the Hill slope, 'c' is the pIC$_{50}$ and 'd' is the maximum.

Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All tested compounds were found to have a pIC$_{50}$≥4.0 in at least one assay described above.

Examples 104, 108, 110-123 were found to have a pIC$_{50}$≥4.0 and <6.0 in the BRD4 BD2 assay.

All other compounds were found to have a pIC$_{50}$ ≥6.0 in the BRD4 BD2 assay.

Calculation of Selectivity for BRD4 BD2 Over BRD4 BD1

Selectivity for BRD4 BD2 over BRD4 BD1 was calculated as follows:

Selectivity=BRD4 BD2 pIC$_{50}$−BRD4 BD1 pIC$_{50}$

With the exception of Examples 117-123 all tested compounds were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1-94 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Examples 1, 13, 14, 15, 16, 17, 18, 19, 25, 45, 46, 49, 50, 53, 59, 77, 82, 91 and 94 were found to have selectivity for BRD4 BD2 over BRD4 BD1 of ? 3 log unit in at least one of the TR-FRET assays described above, and hence are at least 1000 fold selective for BRD4 BD2 over BRD4 BD1.

The invention claimed is:

1. A compound of formula (I)

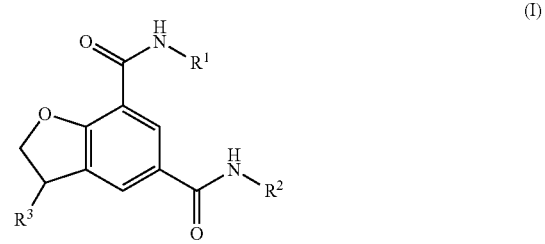

or a pharmaceutically acceptable salt thereof,
wherein:
R$^1$ is —C$_{1-3}$ alkyl or cyclopropyl;
R$^2$ is —C$_{0-3}$ alkyl-cycloalkyl, wherein the cycloalkyl group is optionally substituted with one, two or three R$^5$ groups which may be the same or different;
R$^2$ is —C$_{0-4}$alkyl-heterocyclyl or —(CH$_2$)$_p$O-heterocyclyl wherein each heterocyclyl is optionally substituted by one or two R$^9$ groups which may be the same or different; or
R$^2$ is H, —CH$_3$, —C$_{2-6}$alkyl optionally substituted by up to five fluoro, —C$_{2-6}$alkylOR$^{13}$, —C$_{2-6}$alkylNR$^{11}$R$^{12}$, —(CH$_2$)mSO$_2$C$_{1-3}$alkyl, —(CH$_2$)mSO$_2$NR$^{11}$R$^{12}$, —(CH$_2$)$_m$C(O)NR$^{11}$R$^{12}$, —(CH$_2$)$_m$CN, —(CH$_2$)$_m$CO$_2$R$^{13}$, —(CH$_2$)$_m$NHCO$_2$C$_{1-4}$alkyl —(CH$_2$)$_m$NHC(O)C$_{1-4}$alkyl or —(CH$_2$)$_m$heteroaryl wherein heteroaryl is optionally substituted by one or two R$^7$ groups which may be the same or different;
R$^3$ is phenyl optionally substituted with one, two or three R$^7$ groups which may be the same or different; or
R$^3$ is heteroaryl optionally substituted with one, two or three R$^7$ groups which may be the same or different; or
R$^3$ is heterocyclyl optionally substituted with one, two or three R$^9$ groups which may be the same or different;

each R⁵ is independently halo, —C₀₋₆alkyl-R⁸, —CN or —SO₂C₁₋₃alkyl;

R⁶ is —H or —C₁₋₃ alkyl;

each R⁷ is independently -halo, —C₁₋₄alkyl, —C₀₋₃alkyl-OR¹⁰, —C₀₋₃alkyl-NR¹⁵R¹⁶, —C₀₋₃alkyl-CONR¹⁵R¹⁶, —CO₂C₁₋₃alkyl, CN or —SO₂R¹⁷;

R⁸ is —H, —OR¹⁰ᵃ, —NR¹⁸R¹⁹ or heteroaryl;

each R⁹ is independently halo, —C₁₋₄alkyl, cyclopropyl, cyclobutyl, —CH₂CF₃, —CH₂CHF₂, —CH₂CH₂F, —OCH₂CH₂OR¹³, —C₀₋₃alkylOR¹³, —C₀₋₃alkylNR¹¹R¹², —NHCH₂CH₂OR¹³, —NHCO₂R¹³, oxo, —C(O)R¹³, —C(O)OR¹³ or —C(O)NR¹¹R¹²;

R¹⁰ᵃ is —H, —C₁₋₃alkyl, —C₂₋₃alkylNR¹¹R¹² or —C₂₋₃alkylOH;

R¹⁰ is —H, —C₁₋₃alkyl, —C₂₋₃alkylNR¹⁵R¹⁶ or —C₂₋₃alkylOH;

R¹¹ and R¹² are each independently selected from —H and —C₁₋₃alkyl; or R¹¹ and R¹² may join together with the nitrogen to which they are attached, to form a 4 to 7-membered heterocyclyl group optionally substituted by one or two substituents independently selected from —C₁₋₃alkyl, —OH and F;

R¹³ is —H or C₁₋₄alkyl;

R¹⁵ and R¹⁶ are each independently selected from —H and —C₁₋₃alkyl;

R¹⁷ is —C₁₋₃alkyl or —NR¹⁵R¹⁶;

R¹⁸ and R¹⁹ are each independently selected from —H, —C(O)OC(CH₃)₃, —C₁₋₆alkyl, cycloalkyl, heterocyclyl, —C₂₋₃alkylNR¹³COC₁₋₃alkyl, —C₂₋₃alkylNR¹⁵R¹⁶ and —C₂₋₃alkyl-O—C₁₋₃alkyl wherein the —C₁₋₆alkyl and cycloalkyl may be optionally substituted by one, two or three fluoro; or R¹⁸ and R¹⁹ may join together with the nitrogen to which they are attached, to form a 4 to 7-membered heterocyclyl group optionally substituted by one or two substituents independently selected from —C₁₋₃alkyl, —OH and F;

m is an integer selected from 2, 3 and 4;

p is an integer selected from 2, 3 and 4; and n is an integer selected from 0, 1, 2, 3 and 4.

2. The compound or pharmaceutically acceptable salt thereof according to claim 1, wherein R¹ is methyl.

3. The compound or pharmaceutically acceptable salt thereof according to claim 1, wherein R² is —C₀₋₃alkyl-C₃₋₇cycloalkyl and the C₃₋₇cycloalkyl group is optionally substituted with one, two or three R⁵ groups which may be the same or different.

4. The compound or pharmaceutically acceptable salt thereof according to claim 3, wherein R² is cyclopropyl, cyclobutyl or cyclohexyl optionally substituted with one, two or three R⁵ groups which may be the same or different.

5. The compound or pharmaceutically acceptable salt thereof according to claim 4, wherein R⁵ is —C₀₋₆alkyl-R⁸.

6. The compound or pharmaceutically acceptable salt thereof according to claim 5, wherein R⁵ is selected from methyl, —CH₂OH, —CH₂CH₂OH, —OH, —OMe and —CH₂CH₂morpholinyl.

7. The compound or pharmaceutically acceptable salt thereof according to claim 1, wherein R² is —C₀₋₄alkyl heterocyclyl or —(CH₂)ₚO-heterocyclyl, wherein each heterocyclyl is optionally substituted by one or two R⁹ groups which may be the same or different.

8. The compound or pharmaceutically acceptable salt thereof according to claim 7, wherein R² is —C₀₋₄alkyl-heterocyclyl, wherein the heterocyclyl is optionally substituted by one or two R⁹ groups which may be the same or different.

9. The compound or pharmaceutically acceptable salt thereof according to claim 8, wherein —C₀₋₄alkyl-heterocyclyl is selected from heterocyclyl, —CH₂CH₂-heterocyclyl and —CH₂CH₂CH₂-heterocyclyl.

10. The compound or pharmaceutically acceptable salt thereof according to claim 7, wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two R⁹ groups which may be the same or different.

11. The compound or pharmaceutically acceptable salt thereof according to claim 10, wherein the heterocyclyl is optionally substituted by one or two R⁹ groups selected from methyl —C(O)CH₃ and fluoro.

12. The compound or pharmaceutically acceptable salt thereof according to claim 7, wherein the heterocyclyl optionally substituted by one or two R⁹ groups is selected from:

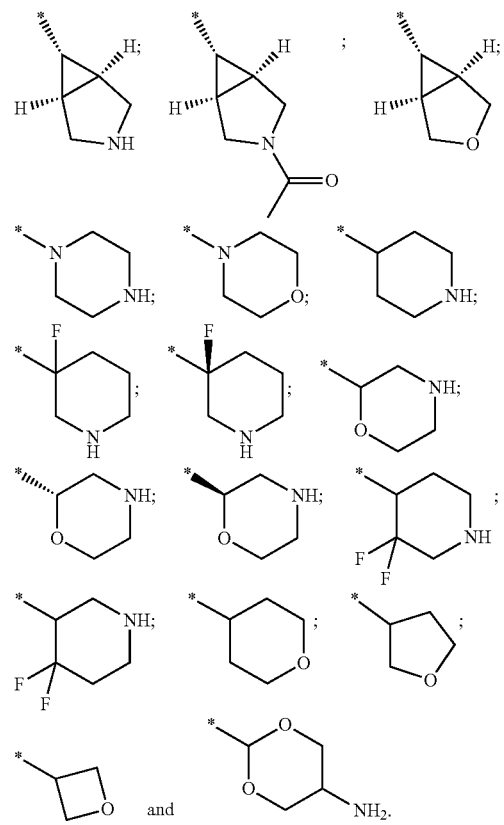

*denotes point of attachment

13. The compound or pharmaceutically acceptable salt thereof according to claim 1, wherein R² is —H, —CH₃, C₂₋₆alkyl optionally substituted by up to five fluoro, —C₂₋₆alkylOR¹³, —C₂₋₆alkylNR¹¹R¹², —(CH₂)ₘSO₂C₁₋₃alkyl, —(CH₂)ₘC(O)NR¹¹R¹², —(CH₂)ₘCN, —(CH₂)ₘCO₂R¹³, —(CH₂)ₘNHCO₂C(CH₃)₃ or —(CH₂)ₙC₅₋₆heteroaryl, wherein C₅₋₆heteroaryl is optionally substituted by one or two R⁷ groups which may be the same or different.

14. The compound or pharmaceutically acceptable salt thereof according to claim 13, wherein R² is —H, —CH₃, C₂₋₆alkyl, —C₂₋₆alkylOR¹³, —C₂₋₆alkylNR¹¹R¹² or —(CH₂)ₙC₅₋₆heteroaryl.

15. The compound or a pharmaceutically acceptable salt thereof according to claim 14, wherein $R^2$ is —H, methyl, ethyl, propyl, —CH$_2$CH$_2$OH, —CH$_2$CH$_2$CH$_2$OH, —CH$_2$CH(CH$_3$)OH, —CH$_2$CH$_2$OCH$_3$, —CH$_2$CH$_2$CH$_2$OCH$_3$, —CH$_2$CH$_2$N(CH$_3$)$_2$, —CH$_2$CH$_2$CH$_2$N(CH$_3$)$_2$, —CH$_2$CHF$_2$ or —CH$_2$CH$_2$pyridinyl.

16. The compound or pharmaceutically acceptable salt thereof according to claim 1, wherein $R^3$ is phenyl optionally substituted by one -halo, —CH$_3$, —OCH$_3$ or —CN.

17. The compound or pharmaceutically acceptable salt thereof according to claim 1, wherein $R^3$ is pyridyl optionally substituted with one $R^7$ group.

18. The compound or pharmaceutically acceptable salt thereof according to claim 1, wherein $R^3$ is indolyl optionally substituted with one or two $R^7$ groups which may be the same or different.

19. The compound or pharmaceutically acceptable salt thereof according to claim 1, wherein $R^3$ is tetrahydropyranyl optionally substituted with one or two $R^9$ groups which may be the same or different.

20. The compound or pharmaceutically acceptable salt thereof according to claim 1, wherein the compound is selected from:

$N^5$-cyclopropyl-3-(1H-indol-4-yl)-$N^7$-methyl-2,3-dihydrobenzofuran-5,7-dicarboxamide;
(+/−)-$N^5$-((1R,5S,6r)-3-Oxabicyclo[3.1.0]hexan-6-yl)-3-(1H-indol-4-yl)-$N^7$-methyl-2,3-dihydrobenzofuran-5,7-dicarboxamide;
$N^5$-(2-(1H-pyrazol-5-yl)ethyl)-$N^7$-methyl-3-phenyl-2,3-dihydrobenzofuran-5,7-dicarboxamide;
$N^5$-(2-(3,3-difluoropiperidin-4-yl)ethyl)-$N^7$-methyl-3-phenyl-2,3-dihydrobenzofuran-5,7-dicarboxamide;
3-(4-fluorophenyl)-M-methyl-$N^5$-(2-(1-methyl-1H-pyrazol-4-yl)ethyl)-2,3-dihydrobenzofuran-5,7-dicarboxamide;
$N^7$-methyl-3-phenyl-$N^5$-(pyridin-4-yl)-2,3-dihydrobenzofuran-5,7-dicarboxamide;
$N^5$-(1-(2-hydroxyethyl)-1H-pyrazol-4-yl)-$N^7$-methyl-3-phenyl-2,3-dihydrobenzofuran-5,7-dicarboxamide;
$N^7$-methyl-3-phenyl-$N^5$-(2-(pyridin-4-ethyl)-2,3-dihydrobenzofuran-5,7-dicarboxamide;
$N^5$-(2-methoxycyclopropyl)-$N^7$-methyl-3-phenyl-2,3-dihydrobenzofuran-5,7-dicarboxamide;
$N^7$-methyl-$N^5$-(1-methyl-1H-1,2,3-triazol-4-yl)-3-phenyl-2,3-dihydrobenzofuran-5,7-dicarboxamide;
$N^7$-methyl-3-phenyl-$N^5$-(pyrimidin-5-yl)-2,3-dihydrobenzofuran-5,7-dicarboxamide;
$N^7$-methyl-3-phenyl-$N^5$-(pyridin-3-yl)-2,3-dihydrobenzofuran-5,7-dicarboxamide;
$N^7$-methyl-$N^5$-((1S,2S)-2-methylcyclopropyl)-3-phenyl-2,3-dihydrobenzofuran-5,7-dicarboxamide;
$N^5$-((1R,5 S,6r)-3-oxabicyclo[3.1.0]hexan-6-yl)-$N^7$-methyl-3-phenyl-2,3-dihydrobenzofuran-5,7-dicarboxamide;
$N^5$-(3-(3,3-difluoropiperidin-4-yl)propyl)-$N^7$-methyl-3-phenyl-2,3-dihydrobenzofuran-5,7-dicarboxamide;
(+/−)-$N^7$-methyl-$N^5$-(1-methyl-1H-pyrazol-4-yl)-3-phenyl-2,3-dihydrobenzofuran-5,7-dicarboxamide;
(S*)-$N^7$-methyl-$N^5$-(2-methyl-2H-1,2,3-triazol-4-yl)-3-phenyl-2,3-dihydrobenzofuran-5,7-dicarboxamide;
(S*)-$N^7$-methyl-$N^5$-(1-methyl-1H-pyrazol-4-yl)-3-phenyl-2,3-dihydrobenzofuran-5,7-dicarboxamide;
(S*)-$N^5$-(1-(2-hydroxyethyl)-1H-pyrazol-4-yl)-$N^7$-methyl-3-phenyl-2,3-dihydrobenzofuran-5,7-dicarboxamide;
(+/−)-$N^5$-cyclopropyl-$N^7$-methyl-3-phenyl-2,3-dihydrobenzofuran-5,7-dicarboxamide;
(+/−)-$N^7$-methyl-3-phenyl-$N^5$-(pyrimidin-4-yl)-2,3-dihydrobenzofuran-5,7-dicarboxamide;
(+/−)-$N^7$-methyl-3-phenyl-$N^5$-(pyridazin-4-yl)-2,3-dihydrobenzofuran-5,7-dicarboxamide;
(+/−)-$N^7$-methyl-3-phenyl-$N^5$-(pyridazin-3-yl)-2,3-dihydrobenzofuran-5,7-dicarboxamide;
(+/−)-$N^7$-methyl-3-phenyl-$N^5$-(tetrahydrofuran-3-yl)-2,3-dihydrobenzofuran-5,7-dicarboxamide;
(+/−)-$N^5$-((1R,5S,6r)-3,3-difluorobicyclo[3.1.0]hexan-6-yl)-$N^7$-methyl-3-phenyl-2,3-dihydrobenzofuran-5,7-dicarboxamide;
(S*)-$N^7$-methyl-$N^5$-(2-(1-methyl-1H-pyrazol-4-yl)ethyl)-3-phenyl-2,3-dihydrobenzofuran-5,7-dicarboxamide;
(S*)-$N^5$-ethyl-$N^7$-methyl-3-phenyl-2,3-dihydrobenzofuran-5,7-dicarboxamide;
(+/−) $N^7$-methyl-3-phenyl-$N^5$-(2-(pyridin-3-ypethyl)-2,3-dihydrobenzofuran-5,7-dicarboxamide;
(+/−) $N^7$-methyl-$N^5$-(1-(methylsulfonyl)azetidin-3-yl)-3-phenyl-2,3-dihydrobenzofuran-5,7-dicarboxamide;
(+/−) $N^5$-(2-(1H-imidazol-4-yl)ethyl)-$N^7$-methyl-3-phenyl-2,3-dihydrobenzofuran-5,7-dicarboxamide;
(+/−)$N^7$-methyl-3-phenyl-$N^5$-((tetrahydrofuran-3-yl)methyl)-2,3-dihydrobenzofuran-5,7-dicarboxamide;
(+/−) $N^7$-methyl-$N^5$-((1-methyl-1H-pyrazol-4-yl)methyl)-3-phenyl-2,3-dihydrobenzofuran-5,7-dicarboxamide;
(+/−) $N^5$-(3-methoxypropyl)-$N^7$-methyl-3-phenyl-2,3-dihydrobenzofuran-5,7-dicarboxamide;
(+/−) $N^7$-methyl-3-phenyl-$N^5$-(tetrahydro-2H-pyran-4-yl)-2,3-dihydrobenzofuran-5,7-dicarboxamide;
(+/−) $N^5$-(2-methoxyethyl)-$N^7$-methyl-3-phenyl-2,3-dihydrobenzofuran-5,7-dicarboxamide;
(+/−) $N^7$-methyl-$N^5$-(3-methyl-1H-pyrazol-4-yl)-3-phenyl-2,3-dihydrobenzofuran-5,7-dicarboxamide;
(+/−) $N^7$-methyl-$N^5$-(1-methyl-1H-1,2,4-triazol-3-yl)-3-phenyl-2,3-dihydrobenzofuran-5,7-dicarboxamide;
(+/−) 3-(4-Fluorophenyl)-$N^7$-methyl-$N^5$-(1-methyl-1H-pyrazol-4-yl)-2,3-dihydrobenzofuran-5,7-dicarboxamide;
(+/−)-$N^7$-Methyl-$N^5$-(oxetan-3-yl)-3-phenyl-2,3-dihydrobenzofuran-5,7-dicarboxamide;
(+/−)-$N^5$-Ethyl-$N^7$-methyl-3-phenyl-2,3-dihydrobenzofuran-5,7-dicarboxamide;
(+/−)-$N^5$-((trans)-2-(2-Hydroxyethypcyclopropyl)-$N^7$-methyl-3-phenyl-2,3-dihydrobenzofuran-5,7-dicarboxamide;
(+/−)-$N^7$-Methyl-$N^5$-(2-(1-methyl-1H-pyrazol-4-yl)ethyl)-3-phenyl-2,3-dihydrobenzofuran-5,7-dicarboxamide;
(+/−)-$N^7$-Methyl-$N^5$-(2-methyl-2H-1,2,3-triazol-4-yl)-phenyl-2,3-dihydrobenzofuran-5,7-dicarboxamide;
(S)-$N^7$-methyl-3-phenyl-$N^5$-(pyrimidin-5-yl)-2,3-dihydrobenzofuran-5,7-dicarboxamide;
(S*)-3-(4-fluorophenyl)-$N^7$-methyl-$N^5$-(2-(1-methyl-1H-pyrazol-4-yl)ethyl)-2,3-dihydrobenzofuran-5,7-dicarboxamide;
(S*)-3-(1H-indol-4-yl)-$N^7$-methyl-$N^5$-(2-(1-methyl-1H-pyrazol-4-yl)ethyl)-2,3-dihydrobenzofuran-5,7-dicarboxamide;
(S*)-$N^5$-cyclopropyl-3-(4-fluorophenyl)-$N^7$-methyl-2,3-dihydrobenzofuran-5,7-dicarboxamide;
(R*)$N^5$-((1R,5S,6r)-3-oxabicyclo[3.1.0]hexan-6-yl)-$N^7$-methyl-3-(o-tolyl)-2,3-dihydrobenzofuran-5,7-dicarboxamide;

(S*)-N⁷-methyl-N⁵-((1S,2S)-2-methylcyclopropyl)-3-phenyl-2,3-dihydrobenzofuran-5,7-dicarboxamide;
(S*)-N⁵-((1R,5S,6R)-3-oxabicyclo [3.1.0] hexan-6-yl)-N⁷-methyl-3-phenyl-2,3-dihydrobenzofuran-5,7-dicarboxamide;
(S*)-N⁵-cyclopropyl-N⁷-methyl-3-phenyl-2,3-dihydrobenzofuran-5,7-dicarboxamide;
(S*)-3-(4-(2-aminoethoxy)phenyl)-N⁵-((1R,5S,6r)-3-oxabicyclo [3.1.0]hexan-6-yl)-N⁷-methyl-2,3-dihydrobenzofuran-5,7-dicarboxamide;
(S*)-N⁵-((1R,5S,6r)-3-oxabicyclo [3.1.0] hexan-6-yl)-N⁷-methyl-3-phenyl-2,3-dihydrobenzofuran-5,7-dicarboxamide;
(S*)-cyclopropyl-3-(3-fluorophenyl)-N⁷-methyl-2,3-dihydrobenzofuran-5,7-dicarboxamide;
(S*)-N⁵-(1R,5S,6r)-3-oxabicyclo [3.1.0] hexan-6-yl)-N⁷-methyl-3-(tetrahydro-2H-pyran-4-yl)-2,3-dihydrobenzofuran-5,7-dicarboxamide;
(S*)-N⁵-cyclopropyl-N⁷-methyl-3-(tetrahydro-2H-pyran-4-yl)-2,3-dihydrobenzofuran-5,7-dicarboxamide;
(S*)-N⁷-methyl-N⁵-((1S,2S)-2-methylcyclopropyl)-3-(tetrahydro-2H-pyran-4-yl)-2,3-dihydrobenzofuran-5,7-dicarboxamide;
(S*)-3-(4-fluorophenyl)-N⁷-methyl-N⁵-(1-methyl-1H-pyrazol-4-yl)-2,3-dihydrobenzofuran-5,7-dicarboxamide;
(R*)-N⁵-Cyclopropyl-3-(1H-indol-4-yl)-N⁷-methyl-2,3-dihydrobenzofuran-5,7-dicarboxamide;
(R*)-N⁵-((1R,5S,6r)-3-Oxabicyclo[3.1.0]hexan-6-yl)-3-(1H-indol-4-yl)-N⁷-methyl-2,3-dihydrobenzofuran-5,7-dicarboxamide;
(R*)-3-(1H-Indol-4-yl)-N⁷-methyl-N⁵-((1S,2S)-2-methylcyclopropyl)-2,3-dihydrobenzofuran-5,7-dicarboxamide;
(S*)-3-(1H-Indol-4-yl)-N⁷-methyl-N⁵-((1S,2S)-2-methylcyclopropyl)-2,3-dihydrobenzofuran-5,7-dicarboxamide;
(R*)-N⁵-((1R,5S,6s)-3-Azabicyclo[3.1.0]hexan-6-yl)-N⁷-methyl-3-phenyl-2,3-dihydrobenzofuran-5,7-dicarboxamide;
(R*)-N⁵-(1R,5S,6r)-3-Oxabicyclo[3.1.0]hexan-6-yl)-3-(4-fluorophenyl)-N⁷-methyl-2,3-dihydrobenzofuran-5,7-dicarboxamide;
N⁵-cyclopropyl-N⁷-methyl-3-(1-methyl-1H-indol-4-yl)-2,3-dihydrobenzofuran-5,7-dicarboxamide;
N⁵-cyclopropyl-3-(4-fluorophenyl)-N⁷-methyl-2,3-dihydrobenzofuran-5,7-dicarboxamide;
N⁵-((1 R,5 S,6r)-3-oxabicyclo[3.1.0]hexan-6-yl)-3-(3-methoxyphenyl)-M-methyl-2,3-dihydrobenzofuran-5,7-dicarboxamide;
3-(4-cyanophenyl)-N⁵-cyclopropyl-N⁷-methyl-2,3-dihydrobenzofuran-5,7-dicarboxamide;
(+/−)N⁵-cyclopropyl-3-(3-methoxyphenyl)-N⁷-methyl-2,3-dihydrobenzofuran-5,7-dicarboxamide;
(+/−)N⁵-(1R,5S,6r)-3-oxabicyclo[3.1.0]hexan-6-yl)-N⁷-methyl-3-(p-tolyl)-2,3-dihydrobenzofuran-5,7-dicarboxamide;
(+/−) N⁵-(1R,5S,6r)-3-oxabicyclo [3.1.0]hexan-6-yl)-3-(3-cyanophenyl)-N⁷-methyl-2,3-dihydrobenzofuran-5,7-dicarboxamide;
(+/−) N⁵-(1R,5S,6r)-3-oxabicyclo[3.1.0]hexan-6-yl)-N⁷-methyl-3-(tetrahydro-2H-pyran-4-yl)-2,3-dihydrobenzofuran-5,7-dicarboxamide;
(+/−)-N⁵-(1R,5S,6r)-3-Oxabicyclo[3.1.0]hexan-6-yl)-N⁷-methyl-3-(pyridin-2-yl)-2,3-dihydrobenzofuran-5,7-dicarboxamide;
(+/−)-N⁵-(1R,5S,6r)-3-Oxabicyclo[3.1.0]hexan-6-yl)-N⁷-methyl-3-(pyridin-3-yl)-2,3-dihydrobenzofuran-5,7-dicarboxamide;
(+/−)N⁵-Cyclopropyl-N⁷-methyl-3-(pyridin-3-yl)-2,3-dihydrobenzofuran-5,7-dicarboxamide;
(+/−)-N⁵-(1R,5S,6r)-3-Oxabicyclo[3.1.0]hexan-6-yl)-N⁷-methyl-3-(pyridin-4-yl)-2,3-dihydrobenzofuran-5,7-dicarboxamide;
(+/−)-N⁵-cyclopropyl-3-(3-fluorophenyl)-N⁷-methyl-2,3-dihydrobenzofuran-5,7-dicarboxamide;
(+/−)-N⁵-(1R,5S,6r)-3-Oxabicyclo[3.1.0]hexan-6-yl)-3-(3-fluorophenyl)-N⁷-methyl-2,3-dihydrobenzofuran-5,7-dicarboxamide;
(+/−)-N⁵-(1R,5S,6r-3-Oxabicyclo[3.1.0]hexan-6-yl)-3-(4-fluorophenyl)-N⁷-methyl-2,3-dihydrobenzofuran-5,7-dicarboxamide;
rac-N⁵-((1 R,5S)-3-oxabicyclo[3.1.0]hexan-6-yl)-N⁷-methyl-3-(1-methyl-1H-indol-4-yl)-2,3-dihydrobenzofuran-5,7-dicarboxamide;
N⁵-(1 R,5 S,6r)-3-oxabicyclo[3.1.0]hexan-6-yl)-3-(4-hydroxyphenyl)-N⁷-methyl-2,3-dihydrobenzofuran-5,7-dicarboxamide;
(+/−)-N⁵-(1R,5S,6r)-3-oxabicyclo[3.1.0]hexan-6-yl)-N⁷-methyl-3-phenyl-2,3-dihydrobenzofuran-5,7-dicarboxamide;
(+/−)-N⁵-(1R,5S,6r)-3-Oxabicyclo[3.1.0]hexan-6-yl)-N⁷-methyl-3-(1H-pyrrolo[2,3-b]pyridin-4-yl)-2,3-dihydrobenzofuran-5,7-dicarboxamide;
N⁵-cyclopropyl-3-(1-(2-hydroxyethyl)-1H-indol-4-yl)-N₇-methyl-2,3-dihydrobenzofuran-5,7-dicarboxamide;
N⁵-(1R,5S,6s)-3-azabicyclo[3.1.0]hexan-6-yl)-N₇-methyl-3-phenyl-2,3-dihydrobenzofuran-5,7-dicarboxamide;
(S)-N⁵-(3-((2s,5R)-5-amino-1,3-dioxan-2-yl)propyl)-N⁷-methyl-3-phenyl-2,3-dihydrobenzofuran-5,7-dicarboxamide;
(+/−)-3-(4-(2-aminoethoxy)phenyl)-N⁵-(1R,5S,6r)-3-oxabicyclo[3.1.0]hexan-6-yl)-N⁷-methyl-2,3-dihydrobenzofuran-5,7-dicarboxamide;
(+/−)-N⁵-(1R,5S,6s)-3-acetyl-3-azabicyclo[3.1.0]hexan-6-yl)-N₇-methyl-3-phenyl-2,3-dihydrobenzofuran-5,7-dicarboxamide;
(+/−)N⁵-(1R,5S,6r)-3-oxabicyclo[3.1.0]hexan-6-yl)-3-(1H-indol-3-yl)-N₇-methyl-2,3-dihydrobenzofuran-5,7-dicarboxamide;
(+/−)N⁵-(1R,5S,6r)-3-Oxabicyclo[3.1.0]hexan-6-yl)-3-(3-(2-hydroxyethoxy)phenyl)-N⁷-methyl-2,3-dihydrobenzofuran-5,7-dicarboxamide;
(S)-N⁷-Methyl-3-phenyl-N⁵-(1R,5S,6s)-3-propionyl-3-azabicyclo[3.1.0]hexan-6-yl)-2,3-dihydrobenzofuran-5,7-dicarboxamide;
(+/−)-N⁵-(1R,5S,6r)-3-Oxabicyclo[3.1.0]hexan-6-yl)-3-(1-(2-hydroxyethyl)-1H-indol-4-yl)-N⁷-methyl-2,3-dihydrobenzofuran-5,7-dicarboxamide;
(S)-N⁵-(2r,5S)-5-amino-1,3-dioxan-2-ypethyl)-N⁷-methyl-3-phenyl-2,3-dihydrobenzofuran-5,7-dicarboxamide; and
(+/−) N⁷-methyl-N⁵-(2-((R)-morpholin-2-yl)ethyl)-3-phenyl-2,3-dihydrobenzofuran-5,7-dicarboxamide;
or a pharmaceutically acceptable salt thereof.

21. A pharmaceutical composition comprising the compound or a pharmaceutically acceptable salt thereof according to claim 1 and one or more pharmaceutically acceptable excipients.

* * * * *